(12) United States Patent
Zimmerman et al.

(10) Patent No.: US 12,364,601 B2
(45) Date of Patent: Jul. 22, 2025

(54) DELIVERY SYSTEMS FOR CARDIAC VALVE DEVICES, AND ASSOCIATED METHODS OF OPERATION

(71) Applicant: Half Moon Medical, Inc., Menlo Park, CA (US)

(72) Inventors: Neil Zimmerman, Menlo Park, CA (US); Jeffrey Martin, San Lorenzo, CA (US); Jean-Pierre Dueri, Palo Alto, CA (US); Erik Thai, San Jose, CA (US); Andrew Johnston, Redwood City, CA (US); Douglas Sutton, Menlo Park, CA (US); Cassandra Orth, Santa Clara, CA (US); Robert O'Grady, San Francisco, CA (US); Jose Gonzalez, Fremont, CA (US); Matthew McLean, San Francisco, CA (US); Gaurav Krishnamurthy, Mountain View, CA (US)

(73) Assignee: Half Moon Medical, Inc., Menlo Park, CA (US)

( * ) Notice: Subject to any disclaimer, the term of this patent is extended or adjusted under 35 U.S.C. 154(b) by 1245 days.

(21) Appl. No.: 17/024,667

(22) Filed: Sep. 17, 2020

(65) Prior Publication Data

US 2022/0079755 A1    Mar. 17, 2022

(51) Int. Cl.
*A61F 2/24* (2006.01)
*A61F 2/95* (2013.01)
*A61M 25/00* (2006.01)

(52) U.S. Cl.
CPC .......... *A61F 2/2436* (2013.01); *A61F 2/9517* (2020.05); *A61M 25/0097* (2013.01)

(58) Field of Classification Search
CPC .. A61F 2/2436; A61F 2/9517; A61M 25/0097
See application file for complete search history.

(56) References Cited

U.S. PATENT DOCUMENTS

| 9,750,606 B2 | 9/2017 | Ganesan et al. |
| 10,653,521 B2 | 5/2020 | Dienno et al. |

(Continued)

FOREIGN PATENT DOCUMENTS

| EP | 2702965 A1 | 3/2014 |
| WO | WO2012009006 A1 | 1/2012 |

(Continued)

OTHER PUBLICATIONS

International Search Report and Written Opinion mailed Jul. 24, 2020 in International Patent Application No. PCT/US2020/033478, 11 pages.

(Continued)

*Primary Examiner* — Jing Rui Ou
(74) *Attorney, Agent, or Firm* — Perkins Coie LLP

(57) ABSTRACT

Delivery systems for implanting cardiac valve repair devices are disclosed herein. In some embodiments, a delivery system includes a delivery catheter, a hub shaft extending through the delivery catheter, and a core shaft extending through the hub shaft. The delivery catheter is configured to hold a valve repair device in a compressed configuration. The hub shaft includes a hub configured to releasably engage a first portion of the valve repair device, and the core shaft includes a plug configured to releasably engage a second portion of the valve repair device. When the valve repair device is unsheathed from the delivery catheter, the hub shaft and the core shaft are independently movable to axially elongate/compress the valve repair device. When the valve repair device is properly positioned, the hub can be actuated to release the first portion of the valve repair device, and the plug can be actuated to release the second portion of the valve repair device.

14 Claims, 30 Drawing Sheets

(56) References Cited

U.S. PATENT DOCUMENTS

| | | | |
|---|---|---|---|
| 10,799,361 B2 | 10/2020 | Hauser et al. | |
| 2004/0093063 A1* | 5/2004 | Wright | A61F 2/95 623/1.12 |
| 2007/0112355 A1* | 5/2007 | Salahieh | A61F 2/2418 623/2.11 |
| 2010/0049313 A1 | 2/2010 | Alon et al. | |
| 2010/0286768 A1* | 11/2010 | Alkhatib | A61F 2/2439 623/2.11 |
| 2013/0274855 A1* | 10/2013 | Stante | A61F 2/2436 623/1.11 |
| 2015/0112430 A1* | 4/2015 | Creaven | A61F 2/2436 623/2.11 |
| 2015/0238315 A1* | 8/2015 | Rabito | A61F 2/2436 623/2.11 |
| 2017/0056169 A1* | 3/2017 | Johnson | A61F 2/2433 |
| 2017/0325954 A1* | 11/2017 | Perszyk | A61F 2/2436 |
| 2021/0015608 A1 | 1/2021 | Hauser et al. | |

FOREIGN PATENT DOCUMENTS

| | | |
|---|---|---|
| WO | WO2013175468 A2 | 11/2013 |
| WO | WO2017035381 A1 | 3/2017 |
| WO | WO2017196914 A1 | 11/2017 |

OTHER PUBLICATIONS

International Search Report and Written Opinion mailed Feb. 18, 2022 in International Patent Application No. PCT/US2021/050538, 13 pages.

International Preliminary Report on Patentatbility for International Application No. PCT/US2021/050538 mailed Mar. 30, 2023, 9 pages.

* cited by examiner

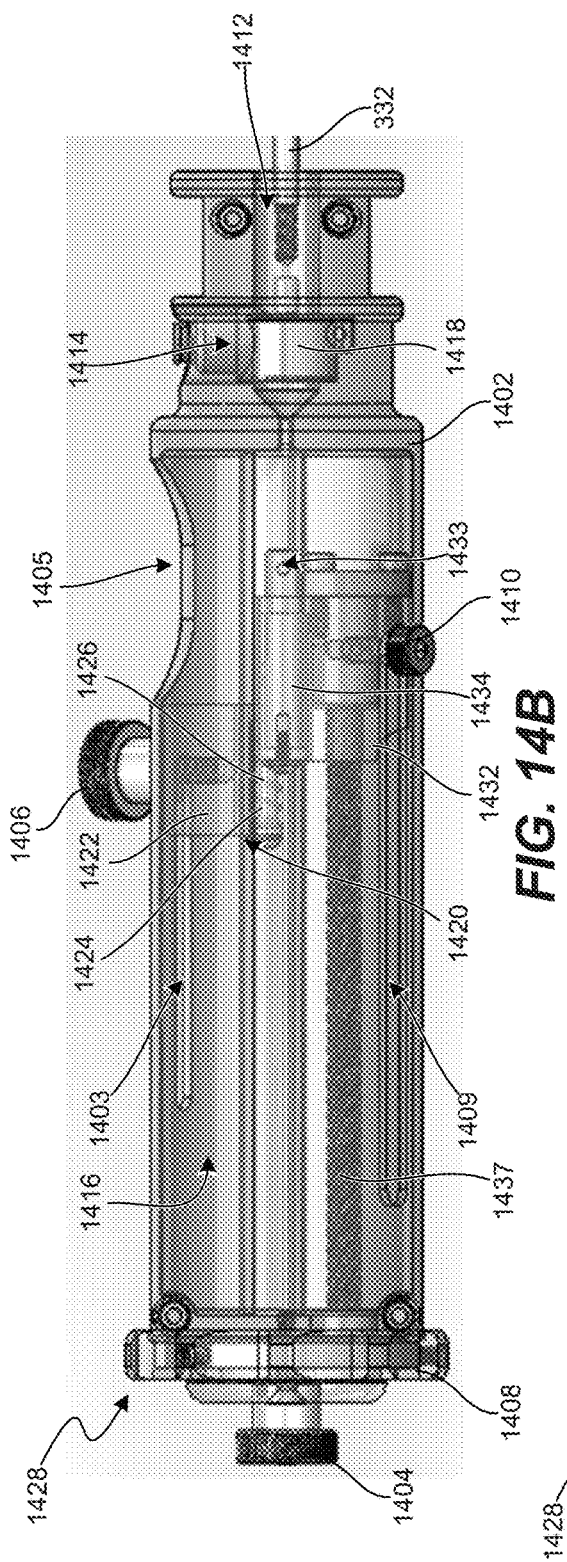
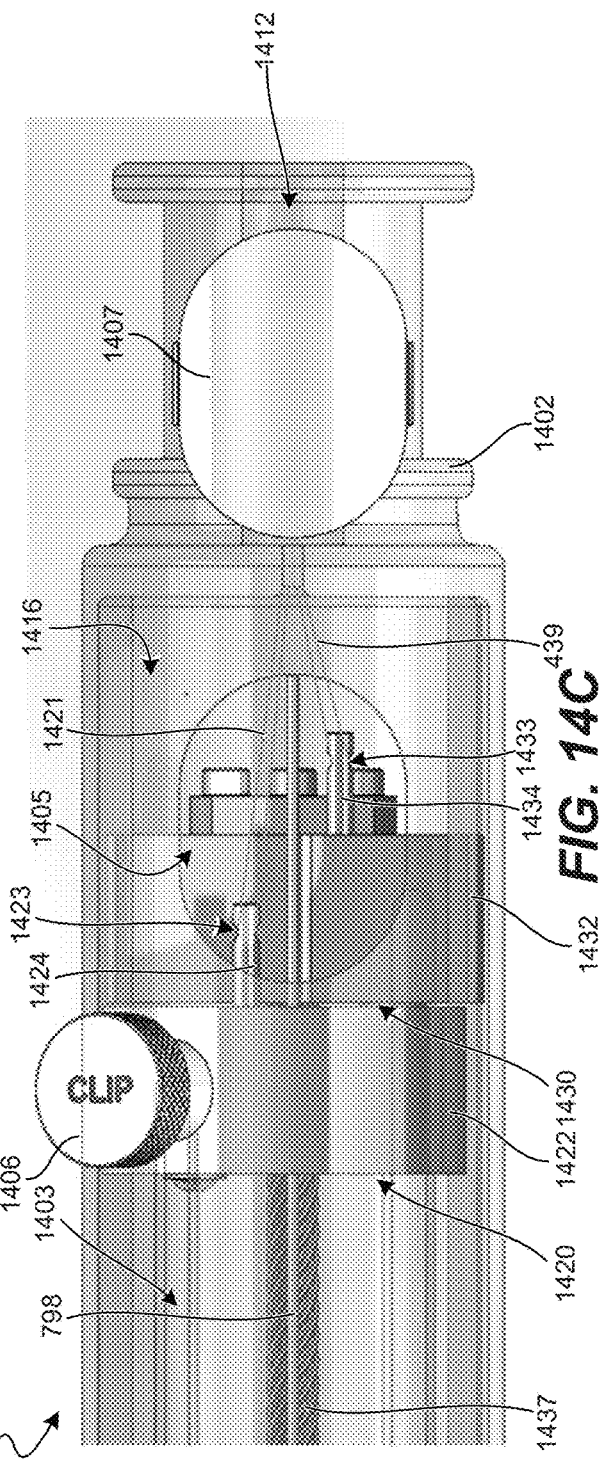
FIG. 14B
FIG. 14C

DELIVERY SYSTEMS FOR CARDIAC VALVE DEVICES, AND ASSOCIATED METHODS OF OPERATION

TECHNICAL FIELD

The present technology generally relates to delivery systems for implanting cardiac valve devices via a minimally invasive procedure, such as an endovascular approach.

BACKGROUND

Proper functioning of the mitral valve can be affected by mitral valve regurgitation, mitral valve prolapse, and/or mitral valve stenosis. Mitral valve regurgitation can occur when the leaflets of the mitral valve fail to coapt into apposition at peak contraction pressures such that blood leaks from the left ventricle into the left atrium. Several structural factors may affect the proper closure of the mitral valve leaflets. For example, an enlarged mitral annulus caused by dilation of heart muscle may prevent proper coaptation of the leaflets during systole. Other conditions involve a stretch or tear in the chordae tendineae—the tendons connecting the papillary muscles to the inferior side of the mitral valve leaflets—which may also affect proper closure of the mitral annulus. A ruptured chordae tendineae, for example, may cause a valve leaflet to prolapse into the left atrium due to inadequate tension on the leaflet. Abnormal backflow can also occur when the papillary muscles are compromised (e.g., due to ischemia) such that the affected papillary muscles do not contract sufficiently to effect proper closure during systole.

Mitral valve prolapse can occur when the mitral leaflets abnormally bulge up in to the left atrium, which can also lead to mitral valve regurgitation. Normal functioning of the mitral valve may also be affected by mitral valve stenosis, or a narrowing of the mitral valve orifice, which impedes of filling of the left ventricle during diastole.

Mitral valve regurgitation is often treated using diuretics and/or vasodilators to reduce the amount of blood flowing back into the left atrium. Other treatment methods, such as surgical approaches (open and intravascular), have also been used to either repair or replace the native mitral valve. For example, cinching or resecting portions of the dilated annulus are typical repair approaches. Cinching of the annulus has been accomplished by implanting annular or peri-annular rings which are generally secured to the annulus or surrounding tissue. Other repair procedures have also involved suturing or clipping of the valve leaflets into partial apposition with one another. Alternatively, more invasive procedures replace the entire valve with mechanical valves or biological tissue. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may cause complications. Moreover, many of the repair procedures depend upon the skill of the cardiac surgeon since poorly or inaccurately placed sutures may affect the success of procedures.

Compared to other cardiac valves, the mitral valve presents unique challenges because portions of the mitral valve annulus have limited radial support from surrounding tissue and the mitral valve has an irregular, unpredictable shape. For example, the anterior wall of the mitral valve is bound by only a thin wall separating the mitral valve annulus from the inferior portion of the aortic outflow tract. As a result, significant radial forces on the mitral valve annulus are not acceptable as they could lead to collapse of the inferior portion of the aortic tract with potentially fatal consequences. Another challenge of the mitral valve anatomy is that the maze of chordae tendineae in the left ventricle makes navigating and positioning a deployment catheter much more difficult compared to other heart valves. Given the difficulties associated with current procedures, there remains the need for simple, effective, and less invasive devices and methods for treating dysfunctional heart valves. Additionally, since it is also difficult to deliver devices to the mitral valve, there also remains the need for effective and less invasive delivery systems to deliver the implantable cardiac devices to the mitral valve.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIGS. 14A-14D are a distally-facing isometric view, a partially transparent side view, a partially transparent enlarged top view, and a partially transparent proximally-facing isometric view, respectively, of a core shaft handle configured in accordance with additional embodiments of the present technology.

DETAILED DESCRIPTION

Figure 1:
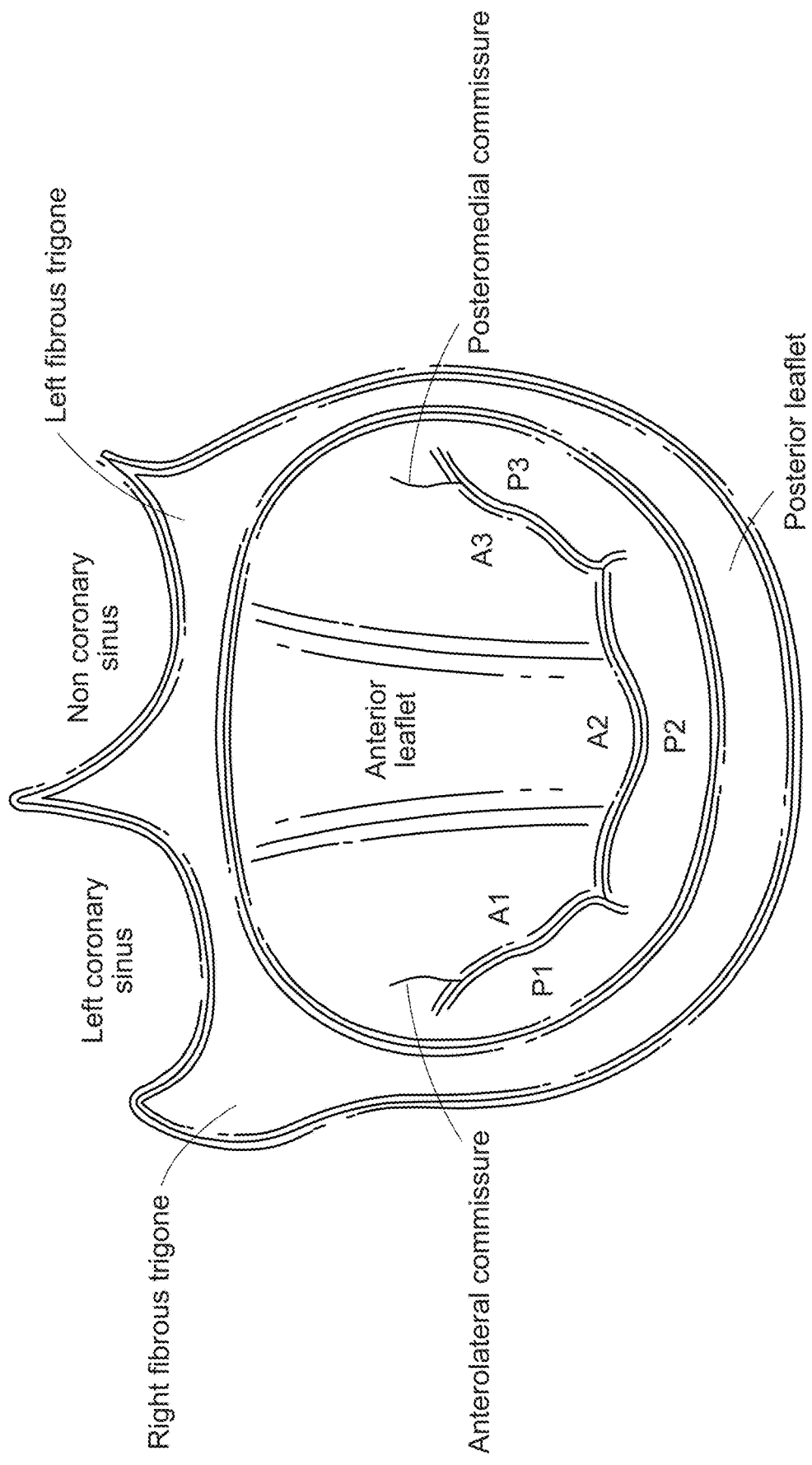
FIG. 1 is a diagram of a mitral valve that may be accessed by a delivery system in accordance with embodiments of the present technology.

Aspects of the present disclosure are directed generally to delivery systems for implanting a medical device, such as a valve repair device or a prosthetic heart valve, in a heart of a subject (e.g., a human patient). In several of the embodiments described below, for example, a delivery system includes a delivery catheter that holds an implantable medical device in a compressed configuration, a hub shaft extending through the delivery catheter, and a core shaft extending through the hub shaft. The hub shaft includes a hub that releasably engages a first portion of the medical device, and the core shaft includes a plug that releasably engages a second portion of the medical device. When the medical device is unsheathed from the delivery catheter, the hub shaft and the core shaft are independently movable (e.g., translatable) relative to one another to axially elongate or axially compress the medical device. When the medical device is properly positioned in the heart, the hub can be actuated to release the first portion of the medical device, and the plug can be actuated to release the second portion of the medical device.

In some embodiments, the medical device is configured to be implanted at a mitral valve of the heart of the subject. In such embodiments, the medical device can be implanted at the mitral valve by at least partially unsheathing the medical device from the delivery catheter in the left atrium above the mitral valve. The medical device is then longitudinally compressed to improve ease of steering by moving one or both of the hub shaft and the core shaft relative to one another. Next, the guide catheter, the delivery catheter, the hub shaft, and/or the core shaft can be used to steer the medical device toward and across the mitral valve annulus such that a portion of the medical device extends into the left ventricle to capture a portion of one or more native leaflets of the mitral valve and anchor the medical device in the sub-annular space behind the leaflet. After determining that the medical device is positioned and functioning properly, the hub and the plug can be actuated to disengage the medical device, leaving the medical device anchored to tissue surrounding the mitral valve.

Specific details of several embodiments of the present technology are described herein with reference to FIGS. 1-12D. The present technology, however, can be practiced without some of these specific details. In some instances, well-known structures and techniques often associated with catheter-based delivery systems, prosthetic heart valves, etc., have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," etc., are not meant to limit the referenced component to use in a specific orientation. It will be appreciated that such designations refer to the orientation of the referenced component as illustrated in the Figures; the systems of the present technology can be used in any orientation suitable to the user.

The headings provided herein are for convenience only and should not be construed as limiting the subject matter disclosed.

I. Selected embodiments of Implantable Devices and Associated Valve Anatomy

FIG. 1 is a diagram of a mitral valve that may be accessed by a delivery system in accordance with embodiments of the present technology. The anterior leaflet has a semi-circular shape and attaches to approximately two-fifths of the annular circumference. The motion of the anterior leaflet defines an important boundary between the inflow (diastole) and outflow (systole) tracts of the left ventricle. The posterior leaflet of the mitral valve has a crescent shape and is attached to approximately three-fifths of the annular circumference. The posterior leaflet typically has two well-defined indentations which divide the leaflet into three individual scallops identified as P1 (lateral scallop), P2 (middle scallop), and P3 (medial scallop). The three corresponding segments of the anterior leaflet are identified as A1 (lateral segment), A2 (middle segment), and A3 (medial segment). The leaflet indentations aid in opening the posterior leaflet during diastole.

As shown in FIG. 1, the mitral valve has anterolateral and posteromedial commissures which define a distinct area where the anterior and posterior leaflets come together at their insertion into the annulus. Sometimes the commissures exist as well-defined leaflet segments, but often this area is a subtle structure that can be identified using the following two anatomic landmarks: (a) the axis of corresponding papillary muscles, and (b) the commissural chordae, which have a specific fan-like configuration. Several millimeters of valvular tissue separate the free edge of the commissures from the annulus.

The mitral valve is an atrio-ventricular valve separating the left atrium from the left ventricle. The mitral annulus constitutes the anatomical junction between the left ventricle and the left atrium. The fixed ends of the leaflets are attached to the annulus. The anterior portion of the mitral annulus is attached to the fibrous trigones and is generally more developed than the posterior annulus. The right fibrous trigone is a dense junctional area between the mitral valve, tricuspid valve, non-coronary cusp of the aortic valve, and the membranous septum. The left fibrous trigone is situated at the junction of both left fibrous borders of the aortic valve and the mitral valve.

The mitral annulus is less well developed at the insertion site of the posterior leaflet. This segment is not attached to any fibrous structures, and the fibrous skeleton in this region is discontinuous. This posterior portion of the annulus is prone to increase its circumference when mitral regurgitation occurs in association with left atrial or left ventricular dilation. The mitral annulus is saddle-shaped, and during systole the commissural areas move proximally—that is, towards the roof of the atrium—while annular contraction also narrows the circumference. Both processes aid in achieving leaflet coaptation, which may be adversely affected by annular dilatation and calcification. The mitral annulus is surrounded by several important anatomic structures, including the aortic valve, the coronary sinus, and the circumflex artery. As a result, implanted cardiac devices at the mitral valve need to be positioned to accommodate the asymmetrical anatomy of the mitral valve without impacting the surrounding cardiac structures.

Figure 2A:
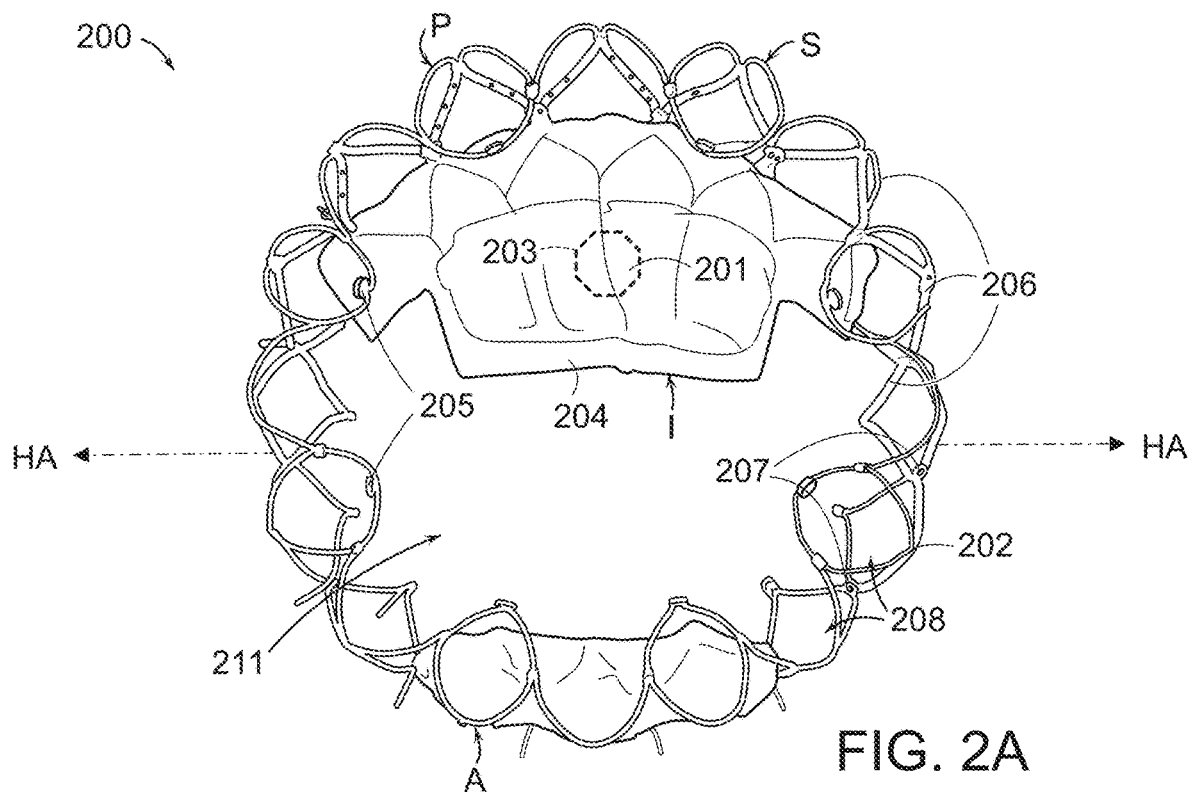
FIGS. 2A and 2B are a top view and a side view, respectively, of an implantable device that may be delivered to a heart of a subject (e.g., a patient) using a delivery system in accordance with embodiments of the present technology.
Figure 2B:
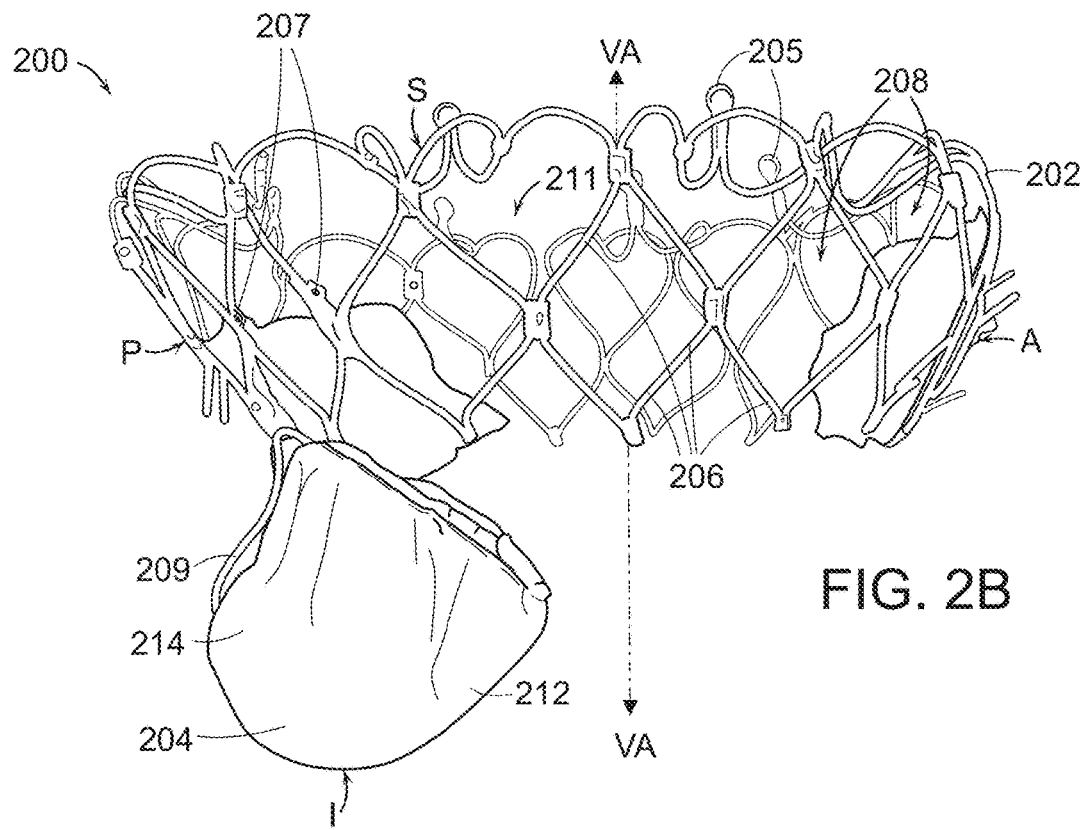

FIGS. 2A and 2B are a top view and a side view, respectively, of an implantable device 200 that may be delivered to a heart of a subject (e.g., a human patient) using a delivery system in accordance with embodiments of the present technology. Referring to FIGS. 2A and 2B together, in the illustrated embodiment the implantable device 200 is a valve repair device having an atrial-fixation member 202 (also referred to as an "anchoring member" or a "brim") and a coaptation member 204 (also referred to as a "baffle") extending from the atrial-fixation member 202 in a downstream direction. The atrial-fixation member 202 is configured to anchor the implantable device 200 to cardiac tissue proximate to a native mitral valve annulus and position the coaptation member 204 at a desired location with respect to the native valve anatomy of the heart. The coaptation member 204 is configured to displace at least a portion of one or more native leaflets of a cardiac valve and create a prosthetic coaptation surface for at least a portion of one or more of the other native leaflets of the cardiac valve. For example, when the implantable device 200 is deployed across the mitral valve annulus, the coaptation member 204 may extend in front of a central portion of the posterior leaflet (i.e., P2 of the posterior leaflet), pushing the posterior leaflet back toward the ventricular wall, such that the coaptation member 204 is positioned to coapt with the anterior leaflet during systole. The implantable device 200 is configured relative to a flow axis VA (FIG. 2B) in the direction of blood flow from the atrium to the ventricle and a transverse axis HA (FIG. 2A) at an angle (e.g., orthogonal) to the flow axis VA. The implantable device 200 has a posterior side portion P (e.g., a first side portion), an anterior side portion A (e.g., a second side portion), a superior end portion S (e.g., a first end portion), and an inferior end portion I (e.g., a second end portion).

In some embodiments, the implantable device 200 can include some features generally similar or identical to the implantable devices described in (i) U.S. patent application Ser. No. 16/044,447, titled "PROSTHETIC LEAFLET DEVICE," and filed Jul. 24, 2018, (ii) International Patent Application No. PCT/US2018/061126, titled "LEAFLET EXTENSION FOR CARDIAC VALVE LEAFLET," and filed Nov. 14, 2018, (iii) U.S. patent application Ser. No. 16/745,246, titled "IMPLANTABLE COAPTATION ASSIST DEVICES WITH SENSORS AND ASSOCIATED SYSTEMS AND METHODS," and filed Jan. 16, 2020, and/or (iv) U.S. patent application Ser. No. 16/817,464, titled "CARDIAC VALVE REPAIR DEVICES WITH ANNULOPLASTY FEATURES AND ASSOCIATED SYSTEMS AND METHODS," and filed Mar. 12, 2020, each of which are incorporated herein by reference in their entirety. Any of several prosthetic valve repair or replacement devices could similarly be used with delivery systems in accordance with the present technology, including complete mitral valve replacement devices. And, in addition to mitral valve devices, other valve repair or replacement devices could be delivered to the tricuspid, aortic, and pulmonic valves using delivery systems in accordance with the present invention.

The atrial-fixation member 202 can be formed of a mesh, such as a braid or laser-cut stent-like structure, including a plurality of interconnected wires or struts 206 which together define a plurality of openings or cells 208 (e.g., diamond-shaped openings) arranged in one or more rows. The struts 206 can be configured to self-expand from a collapsed delivery state (not shown) to an expanded deployed state shown in FIGS. 2A and 2B. The struts 206 can be formed of any biocompatible material such as, for example, stainless steel, nickel-titanium alloys (e.g., nitinol), and/or other suitable stent materials. The atrial-fixation member 202 can have a generally circular, oval, or D-like shape in the deployed state and define an open central lumen 211 (also referred to as an "opening") that allows blood to pass therethrough along the flow axis VA. When the implantable device 200 is configured to repair a native mitral valve, the atrial-fixation member 202 can be shaped to conform to the walls of the left atrium just above the mitral annulus to secure the implantable device 200 to the supra-annular tissue. After a period of time post-implantation (e.g., 3 days, 2 weeks, 1 month, 2 months, the atrial-fixation member 202 or portions thereof become covered by a layer of tissue, and this tissue ingrowth adheres the implantable device 200 permanently to the atrial wall. In some embodiments, the atrial-fixation member 202 has a semi-circular or other shape that does not extend fully around the circumference of the native valve. In some embodiments, the atrial-fixation member 202 may also or alternatively include one or more portions that press against sub-annular tissue to provide sub-annular device fixation.

In some embodiments, the atrial-fixation member 202 can include connectors 205 that are configured (e.g., sized, shaped, and/or positioned) to engage with a mating feature on the delivery system, as described in detail below with reference to FIGS. 5A-5F. As shown in FIG. 2B, for example, the connectors 205 may be extend from the struts 206 such that the connectors 205 are positioned near or at the superior end portion S of the implantable device 200. In some embodiments, the atrial-fixation member 202 includes one or more eyelets 207 configured to receive one or more tendons (e.g., a cinch tendon 439 illustrated in FIG. 4) that aids in packing (e.g., compressing), delivering, orienting, and/or retrieving the implantable device 200. For example, the tendons can help facilitate cinching (e.g., radially compressing) of the atrial-fixation member 202. The eyelets 207 can be metal portions of the atrial-fixation member 202, or can be separate filaments/wires forming loops and attached to the atrial-fixation member 202.

As shown in FIGS. 2A and 2B, the coaptation structure 204 extends away from a downstream end portion of the atrial-fixation member 202 along the flow axis VA and at least a portion of the coaptation member 204 extends radially inward from the atrial-fixation member 202 into the central lumen 211 to approximate a closed position of a native leaflet. The coaptation member 204 can be substantially stationary (e.g., little to no movement) during cardiac cycles such that the position of the coaptation member 204 relative to the atrial-fixation member 202 is at least substantially fixed in the deployed state. Thus, unlike native leaflets that move back and forth to open and close the native valve, the coaptation member 204 remains stationary during diastole and systole.

The coaptation member 204 can have an anterior portion 212 (FIG. 2B) with a smooth, atraumatic surface for coapting with at least a portion of one or more native leaflets and a posterior portion 214 (FIG. 2B) configured to displace and, optionally, engage at least a portion of another native leaflet. The coaptation member 204 can be made from a plurality of struts that form a basket-like or frame-like structure (e.g., a mesh structure, a laser cut stent frame) with an at least partially hollow interior and a covering (e.g., a fabric) extending over at least a portion of the struts to provide a smooth suitable surface for coaptation at the anterior portion 212. The covering may also extend over the struts along the posterior portion 214 and between the anterior and posterior portions 212, 214 in a manner that forms lateral sidewalls. The baffle 204 or portions thereof can be integral with the atrial-fixation member 202 such that, for example, the coaptation member 204 is manufactured from the same frame including the struts 206. In other embodiments, the baffle 204 can be a separate structure that is connected to a portion of the atrial-fixation member 202 during manufacturing. In some embodiments, the baffle 204 can include a biocompatible foam which is attached to the structure of the baffle 204 and/or to the atrial-fixation member 202.

In the illustrated embodiment, the baffle 204 further includes a normally-closed clip 209 (obscured in FIG. 2A) depending from its posterior surface which can be opened to extend behind the native leaflet the coaptation member 204 displaces. The clip 209 may grasp the native leaflet and/or engage sub-annular cardiac tissue for sub-annular stabilization of the implantable device 200. In some embodiments, for example, the clip 209 reaches under the central portion (i.e., P2) of the posterior leaflet up to the sub-annular space. A tendon (made of suture or nitinol wire) can actuate the clip 209 by way of a lever attached to the clip 209. The lever may be a nitinol wire or laser cut nitinol or Co—Cr sheet.

As shown in FIG. 2A, the baffle 204 can further include a delivery attachment member 203 (shown in broken lines) positioned within the hollow interior of the baffle 204. The delivery attachment member 203 can be a threaded nut or other type of connector configured to mate with a corresponding portion (e.g., a screw) of the delivery system, as described in greater detail below with reference to FIGS. 4, 7A, and 7B. In some embodiments, the delivery attachment member 203 is accessible via a flap or opening 201 (FIG. 2A) formed in the baffle 204 (e.g., in portion of the baffle facing the superior end portion S of the implantable device 200).

The implantable device 200 may be inserted via a femoral vein sheath to traverse the inferior vena cava to the right atrium. The implantable device 200 is then inserted into the left atrium via a puncture of the interatrial septum. In several applications, the implantable device 200 is delivered to a target location within the mitral valve to function properly. This means appropriate positioning along the flow axis VA, correct radial positioning relative to the central axis of the valve, correct rotational orientation to specific landmarks such as the middle (P2) portion of the native posterior leaflet, and correct angular positioning relative to the flow axis and the transverse axis. In some embodiments, the implantable device 200 may also be repositioned during the delivery process to, for example, correct for misalignment or inappropriate positioning. During deployment and release of the implantable device 200, the delivery system can retain the implantable device 200 in a stationary position at the desired location and in the desired orientation relative to the native valve. Furthermore, the delivery system may be configured to allow the implantable device 200 to be re-sheathed, repositioned, and/or removed before being released from the delivery system. Delivery systems of the present technology can achieve all the above-mentioned advantages in a user-friendly system. Additionally, several embodiments of delivery systems in accordance with the present technology have a small overall diameter, such as approximately 15 to 30 French.

II. Selected Embodiments of Delivery Systems

Figure 3:
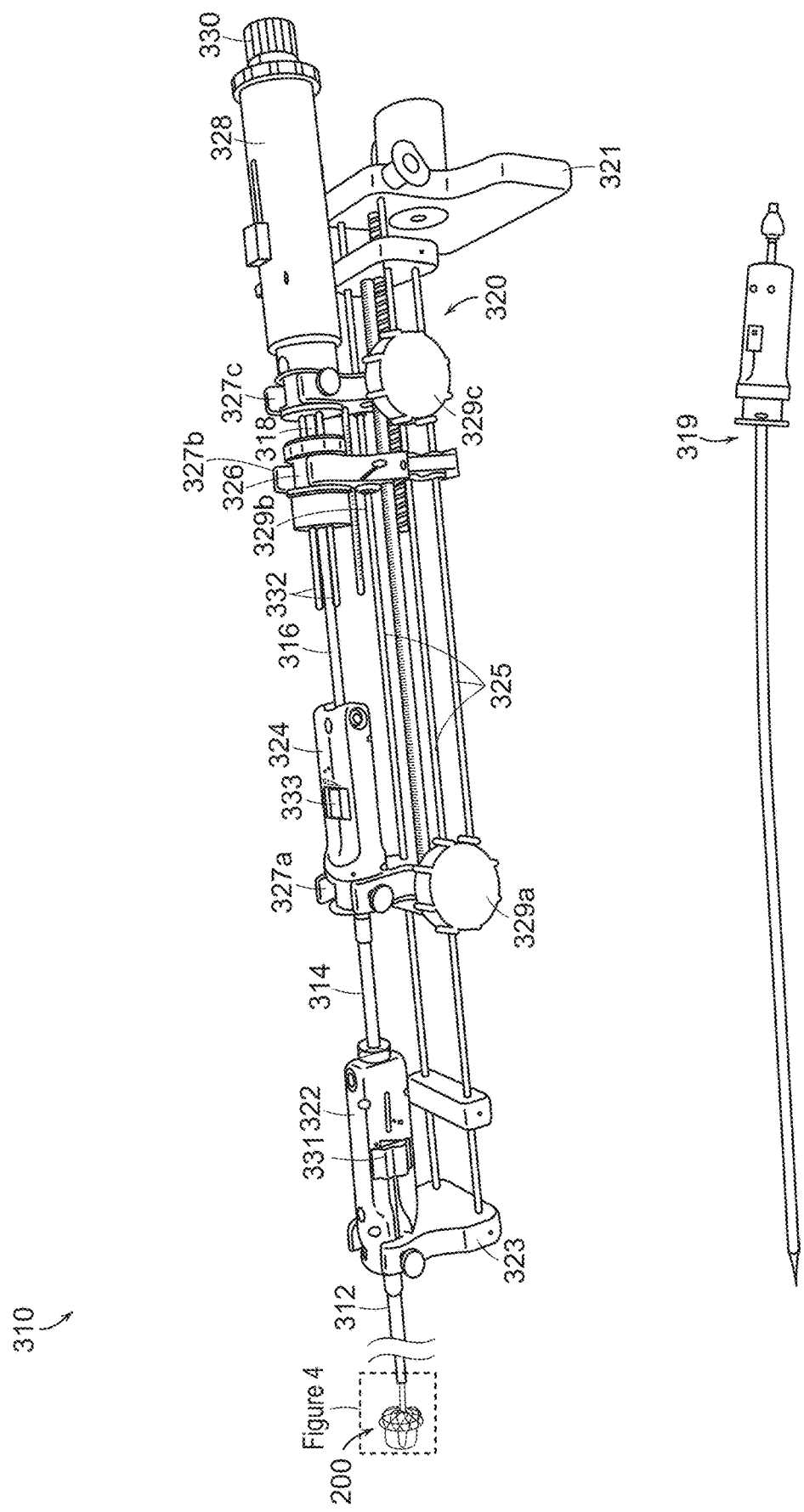
FIG. 3 is a perspective side view of a delivery system configured in accordance with embodiments of the present technology.

FIG. 3 is a perspective side view of a delivery system 310 configured in accordance with embodiments of the present technology. The delivery system 310 can be used to deliver an implantable device, such as the implantable valve repair device 200 of FIGS. 2A and 2B, to a heart of a subject (e.g., a human patient). In the illustrated embodiment, the delivery system 310 includes four nested/coaxial catheter/shaft structures: (i) an outer guide catheter 312, (ii) a delivery catheter 314 (also referred to as a "sleeve") configured to extend at least partially through the guide catheter 312, (iii) a hub shaft 316 configured to extend at least partially through the delivery catheter 314, and (iv) a core shaft 318 configured to extend at least partially through the hub shaft 316 (collectively "catheters 312-318" or "shafts 312-318"). The catheters 312-318 can be individually manipulated and/or moved relative to one another to facilitate deployment of the implantable device 200. More specifically, in the illustrated embodiment (i) the guide catheter 312 is coupled to a guide catheter handle 322, (ii) the delivery catheter 314 is coupled to a delivery catheter handle 324, (iii) the hub shaft 316 is coupled to a hub shaft handle 326, and (iv) the core shaft 318 is coupled to a core shaft handle 328 (collectively "handles 322-328" or "handle assembly"). In some embodiments, the delivery system 310 further includes a dilator assembly 319 configured to be advanced/retracted through the guide catheter 312 prior to introduction of the delivery catheter 314, the hub shaft 316, and/or the core shaft 318.

In some embodiments, the handles 322-328 and/or portions of the catheters 312-318 are coupled/mounted to a common handle support assembly 320 (also referred to as a "rack assembly" or "control rack") that facilitates relative movement between the individual catheters 312-318, while maintaining the handles 322-328 in a stable, supported position and inhibiting unwanted movement therebetween. The support assembly 320 can include a proximal fixed portion 321 (e.g., a first stand), a distal fixed portion 323 (e.g., a second stand), and one or more tracks 325 extending at least partially between the proximal and distal fixed portions 321, 323. In the illustrated embodiment, the guide catheter handle 322 is removably mounted to the distal fixed portion 323.

As shown in FIG. 3, the support assembly 320 can further include a plurality of mounts 327 (identified individually as first through third mounts 327a-327c, respectively) slidably coupled to one or more of the tracks 325. The first mount 327a is configured to receive and secure the delivery catheter handle 324, and includes a first actuation member 329a (e.g., a wheel, slider, knob, button) for individually moving the first mount 327a—and the delivery catheter handle 324 and the delivery catheter 314 coupled thereto—linearly along the tracks 325 relative to the other ones of the handles 322-328. The second mount 327b is positioned proximal of the first mount 327a and is configured to receive and secure the hub shaft handle 326. Similarly, the second mount 327b includes a second actuation member 329b for individually moving the second mount 327b and the hub shaft handle 326. Likewise, the third mount 327c is positioned proximal of the second mount 327b, is configured to receive and secure the core shaft handle 328, and includes a third actuation member 329c for individually moving the third mount 327c and the core shaft handle 328. In the illustrated embodiment, the support assembly 320 further includes a linear drive mechanism 330 (e.g., a screw drive, a rack and pinion) configured to jointly advance/retract the delivery catheter handle 324, the hub shaft handle 326, and the core shaft handle 328 without moving the handles relative to one another. In some embodiments, the linear drive mechanism 330 is coupled to only a subset of the handles 322-328 and/or the system 310 can include more than one linear drive mechanism to linearly advance one or more of the handles 322-328.

The guide catheter 312 and the delivery catheter 314 can each have varying stiffnesses along a length thereof and/or can be steerable catheters that allow the catheters 312, 314 to deflect along one or more axes. In some embodiments, for example, the guide catheter handle 322 includes a guide actuation member 331 (e.g., a wheel, lever, knob, slider) that is actuatable to deflect a distal portion of the guide catheter 312. More specifically, the guide actuation member 331 can be coupled to a pull wire that is attached to a pull ring fixed at a distal portion of the guide catheter 312. Similarly, the delivery catheter handle 324 can include a delivery actuation member 333 that is actuatable to deflect a distal portion of the delivery catheter 314. In some embodiments, the guide catheter 312 has a diameter of less than about 30 French (e.g., about 29.5 French or less) and the delivery catheter 314 has a diameter of about 26 French or less.

Figure 13A:
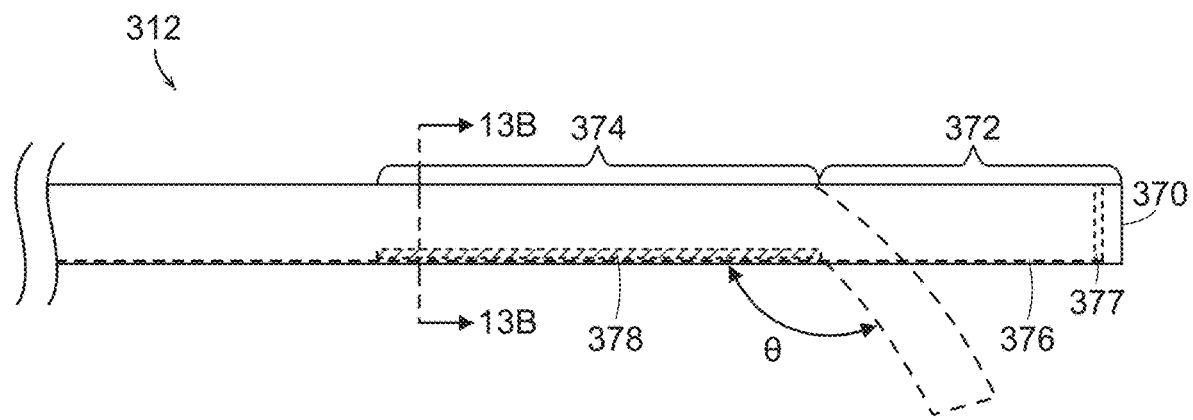
FIG. 13A is a side view of a distal portion of a delivery catheter of FIG. 3 configured in accordance with embodiments of the present technology.
Figure 13B:
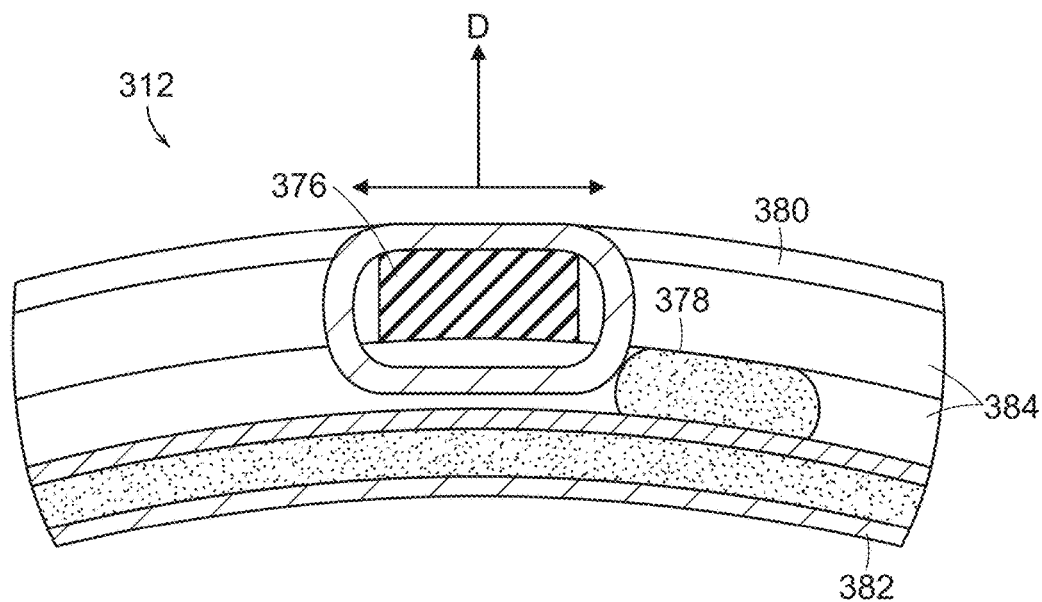
FIG. 13B is an enlarged cross-sectional view of a portion of the delivery catheter of FIG. 3 taken along the line 13B-13B in FIG. 13A.

More specifically, FIG. 13A is a side view of a distal portion of the delivery catheter 314 configured in accordance with embodiments of the present technology. In the illustrated embodiment, the delivery catheter 314 includes a distal terminus 370, a first region 372 (e.g., a distal region) adjacent the distal terminus 370, and a second region 374 (e.g., a proximal region) adjacent to and proximal of the first region 372. FIG. 13B is an enlarged cross-sectional view of a portion of the delivery catheter 314 (e.g., a portion of a wall of the delivery catheter 314) taken along the line 13B-13B in FIG. 13A. In the illustrated embodiment, the delivery catheter 314 includes an outer jacket layer 380, an inner liner layer 382, and one or more layers of braided and/or coiled reinforcement material 384 between the inner liner and outer jacket layers 382, 380 (collectively "layers 380-384"). The inner liner and outer jacket layers 382, 380 can be formed of polytetrafluoroethylene (PTFE), plastic, elastomer, thermoplastic elastomer (TPE) (e.g., a TPE manufactured by Arkema S.A., of Colombes, France, such as the TPEs manufactured under the trademark "Pebax"), nylon, and/or other suitable materials, and the layers of braided and/or coiled material 384 can be formed from metal wires and/or stiffer polymers.

Referring to FIGS. 13A and 13B together, the delivery catheter 314 can further include a pull wire 376 (obscured by the outer jacket layer 380 in FIG. 13A and shown schematically) extending through a lumen between some of the layers 380-384 and having (i) a distal end or portion coupled to a pull ring 377 (obscured by the outer jacket layer 380 in FIG. 13A and shown schematically) positioned in the first region 372 near the distal terminus 370 and (ii) a proximal end or portion coupled to the delivery actuation member 333 in the delivery catheter handle 324 (FIG. 3). Actuation of the delivery actuation member 333 can pull the pull wire 376 to cause the first region 372 and/or the second region 374 to deflect (e.g., in the direction indicated by arrow D in FIG. 13B).

In some embodiments, the delivery catheter 314 can further include a spine 378 (also referred to as an "elongate member") extending at least partially through/along one or more of the layers 380-384. In the illustrated embodiment, the spine 378 extends along the second region 374 but not the first region 372. In some embodiments, the first region 372 can have a length of between about 10-50 millimeters (e.g., about 20 millimeters), and the second region 374 and the spine 378 can have a length of between about 20-80 millimeters (e.g., about 50 millimeters). The spine 378 can be formed of metal or other suitably rigid materials and is positioned adjacent to (e.g., parallel to) the pull wire 376 along the second region 374. In some embodiments, the spine 378 is a metal wire welded (e.g., tack-welded) to the coil reinforcement wire 384 along the second region 374. In some embodiments, when the pull wire 376 is pulled to deflect the delivery catheter 314, the spine 378 inhibits or even prevents the second region 374 of the delivery catheter 376 from flexing in the direction indicated by the arrow D. That is, the spine 378 can inhibit the second region 374 from deflecting while still permitting the first region 372 to deflect in the direction of arrow D. Accordingly, as shown in phantom in FIG. 13A, an angle θ between the first and second regions 372, 374 after actuation of the pull wire 376 can be greater than the angle θ would be without the spine 378. At the same time, the spine 378 can still permit the second region 374 to bend in directions other than the direction of arrow D, such as along an axis O orthogonal to the direction of arrow D. In some aspects of the present technology, this selective flexibility can facilitate advancement of the delivery catheter 314 through the guide catheter 312 (FIG. 3) and/or permit the guide catheter 312 to bend the delivery catheter 314 along the axis O. That is, the spine 378 can provide the delivery catheter 314 with selective flexibility—allowing the delivery catheter 314 to bend along the axis O while remaining stiff and inhibiting bending in the direction of arrow D when the pull wire 376 is pulled.

During a delivery procedure using the delivery system 310, the distal portion of the delivery catheter 314 retains the implantable device 200 in the compressed delivery state and, upon reaching a target region (e.g., in the left atrium), begins to deploy (e.g., unsheathe) the implantable device 200 by retracting the delivery catheter 314 and/or advancing the implantable device 200 beyond the distal terminus of the delivery catheter 314. This allows the implantable device 200 to partially expand toward the deployed state, while still being releasably secured to a distal portion of the hub shaft 316 and a distal portion of the core shaft 318. In FIG. 3, for example, the implantable device 200 is shown in a partially-deployed position (also referred to as a "partially-deployed state") in which the implantable device 200 (i) has been advanced out of the distal portion of the delivery catheter 314, but (ii) is still secured to the hub shaft 316 and the core shaft 318 to allow for controlled movement (e.g., linear, rotational) and further deployment of the partially-deployed implantable device 200.

Figure 4:
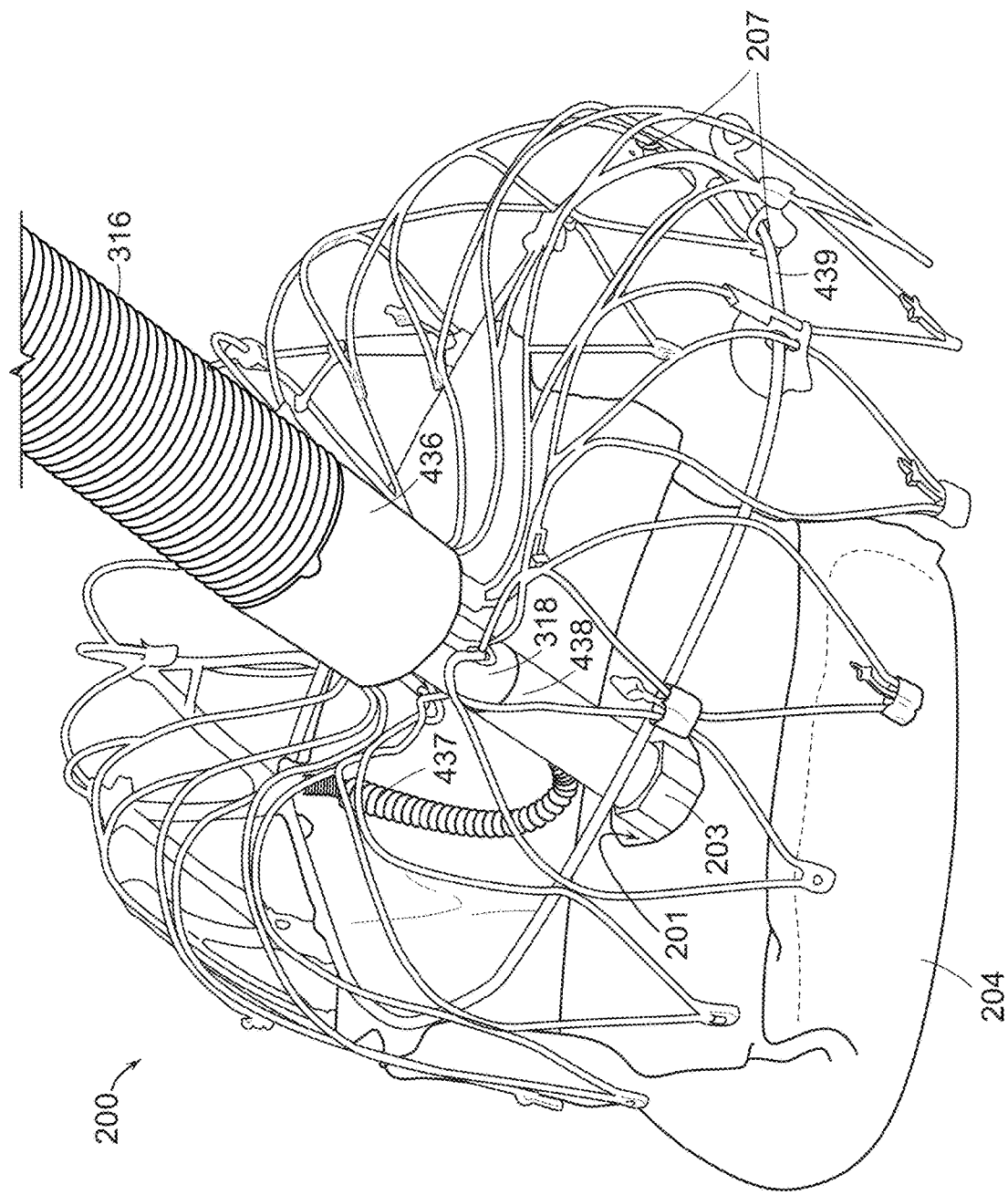
FIG. 4 is an enlarged isometric view of a distal portion of the delivery system of FIG. 3 and the implantable device of FIGS. 2A and 2B in a partially-deployed position in accordance with embodiments of the present technology.

More specifically, FIG. 4 is an enlarged isometric view of a distal portion of the delivery system 310 and the implantable device 200 in the partially-deployed position in accordance with embodiments of the present technology. In the illustrated embodiment, the hub shaft 316 includes a distal hub assembly 436 (described in further detail below with reference to FIGS. 5A-5F) that releasably engages a portion (e.g., the connectors 205 (FIG. 2)) of the implantable device 200. The core shaft 318 includes a distal plug assembly 438 (also referred to as a "core plug" or "plug,"; described in further detail below with reference to FIGS. 7A and 7B) extending through the opening 201 in the baffle 204 and that is releasably coupled to the delivery attachment member 203. Accordingly, relative linear translation between the hub shaft 316 and the core shaft 318 can elongate and/or shorten (e.g., axially, longitudinally, etc.) the implantable device 200 and, more particularly, the atrial-fixation member 202. In the illustrated embodiment, the plug assembly 438 further includes a flexible tube 437 (e.g., a coiled tube) extending therefrom to route a cinch tendon 439 (e.g., a suture) from the proximal portion of the delivery system 310 (e.g., near or at the handles 322-328) to the eyelets 207 of the atrial-fixation member 202.

Referring to FIGS. 3 and 4 together, in some embodiments one or more of the handles 322-328 can be coupled together using means that inhibit relative rotational motion of the handles 322-328. In the illustrated embodiment, for example, the hub shaft handle 326 is slidably coupled to the core shaft handle 328 via a pair of rails 332 (e.g., rigid members, such as rods) that inhibit or even prevent the hub shaft handle 326 and the core shaft handle 328 from rotating relative to one another. Thus, the hub shaft 316 and the core shaft 318 extending from the corresponding hub shaft and core shaft handles 326 and 328 can be rotationally fixed relative to each other (or at least substantially so) during implant procedures. Accordingly, the rails 332 can inhibit or even prevent twisting of the implantable device 200, which has portions coupled to both the hub shaft 316 and the core shaft 318, during an implant procedure that could otherwise arise from rotation of the hub shaft 316 relative to the core shaft 318. In the illustrated embodiment, the hub shaft handle 326 is coupled to the core shaft handle 328 via two rails, whereas in further embodiments the two handles 326, 328 may be coupled together with a single rail, more than two rails (e.g., three, four, five, or more rails), and/or other coupling mechanisms that maintain the rotational alignment of the handles 326, 328 and the catheters and shafts coupled thereto. In other embodiments, the handles 326, 328 can be integrated into a single handle including the various components and functionality described in detail below with reference to FIGS. 8A-8H and/or 14A-14D. In some embodiments, other handles or subsets of handles 322-328 are coupled together in a similar manner to avoid relative motion between the handles 322-328.

Figure 5A:
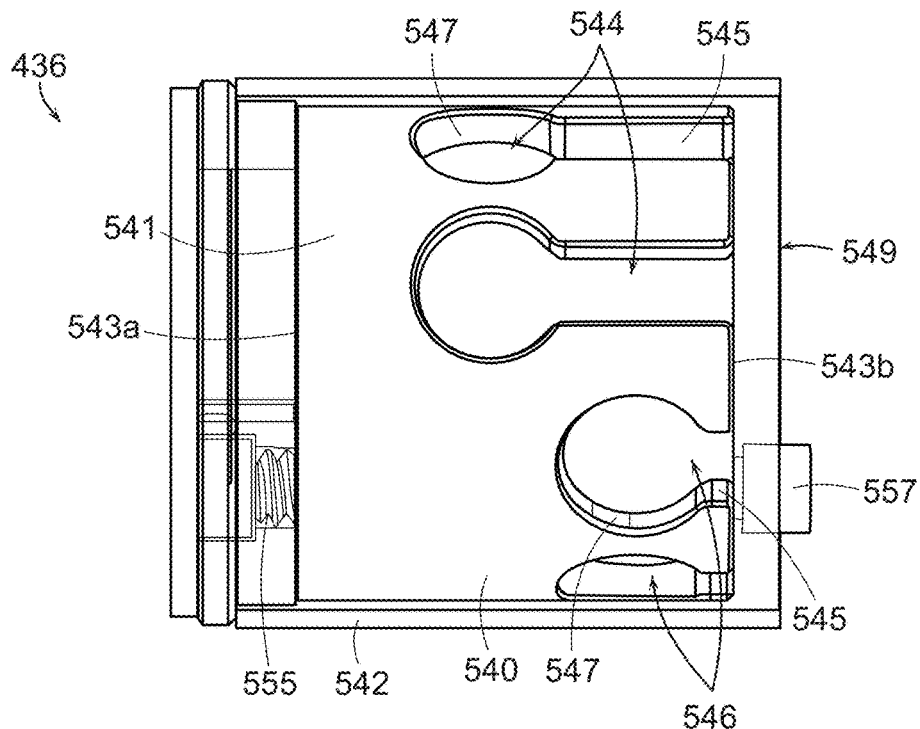
FIGS. 5A-5C are enlarged side views of a hub attachment mechanism of the delivery system of FIG. 3 in a first position, a second position, and a third position, respectively, in accordance with embodiments of the present technology.
Figure 5D:
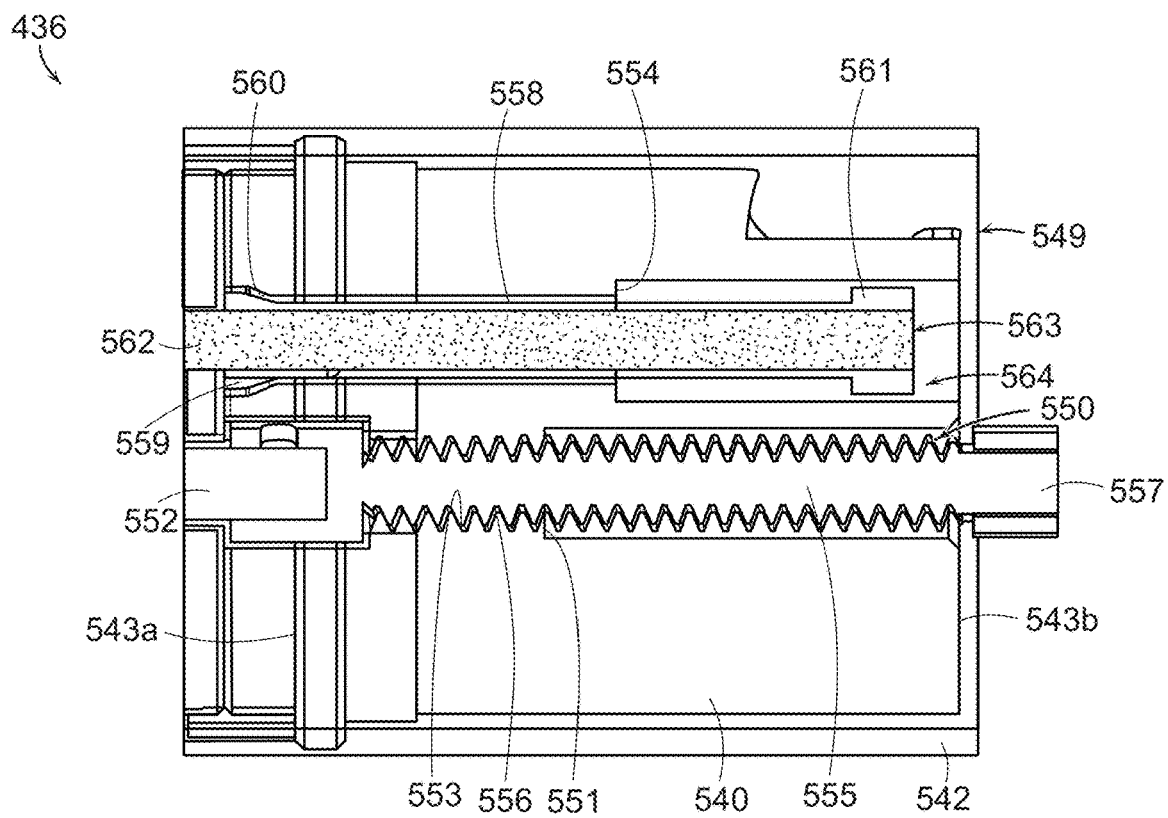
FIGS. 5D-5F are cross-sectional side views of the hub attachment mechanism of FIGS. 5A-5C in the first position, the second position, and the third position, respectively, in accordance with embodiments of the present technology.
Figure 5B:
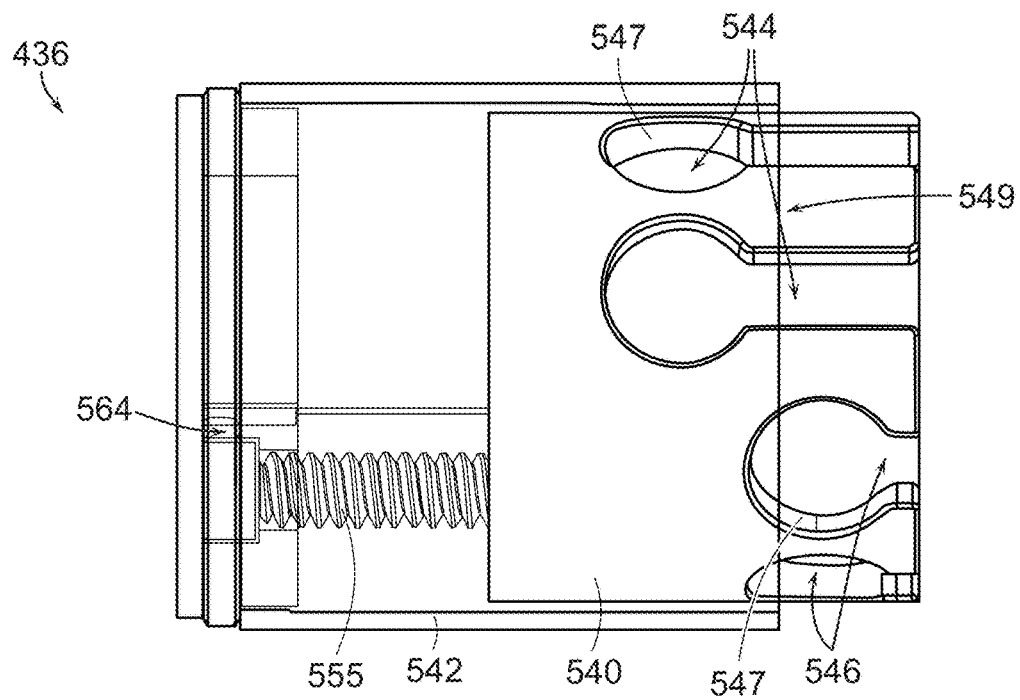
Figure 5E:
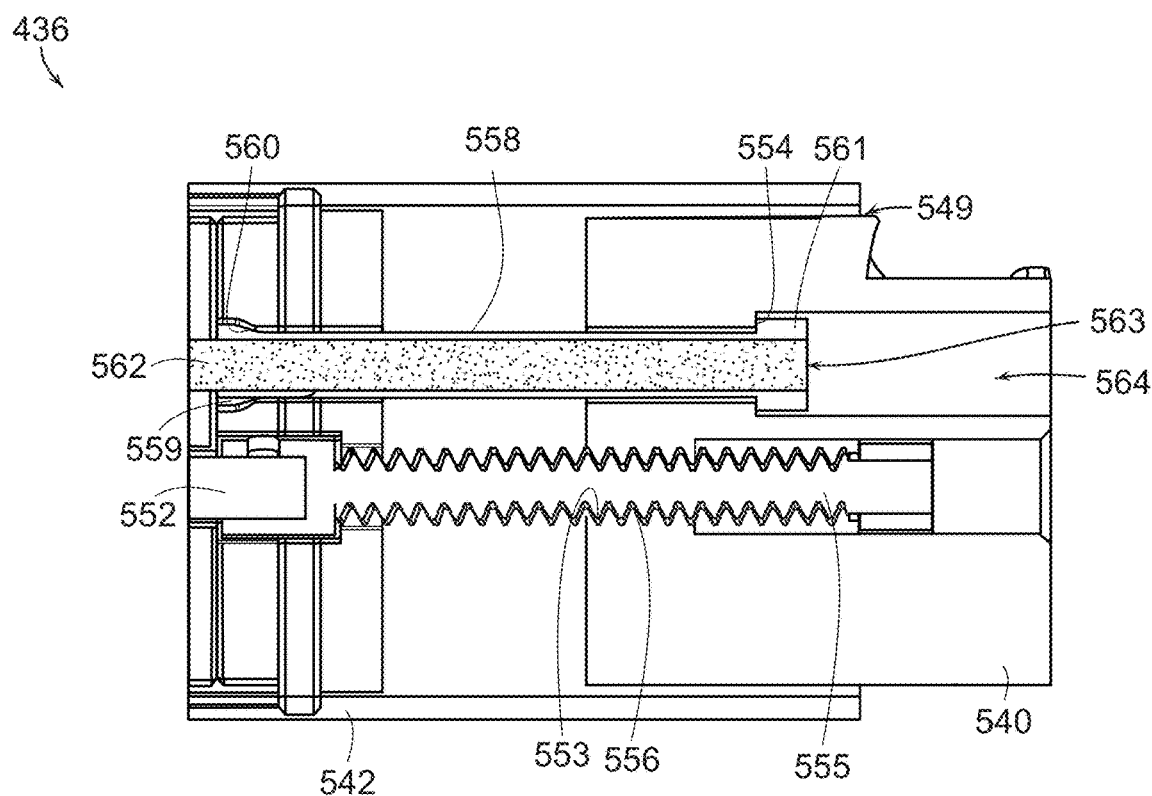
Figure 5C:
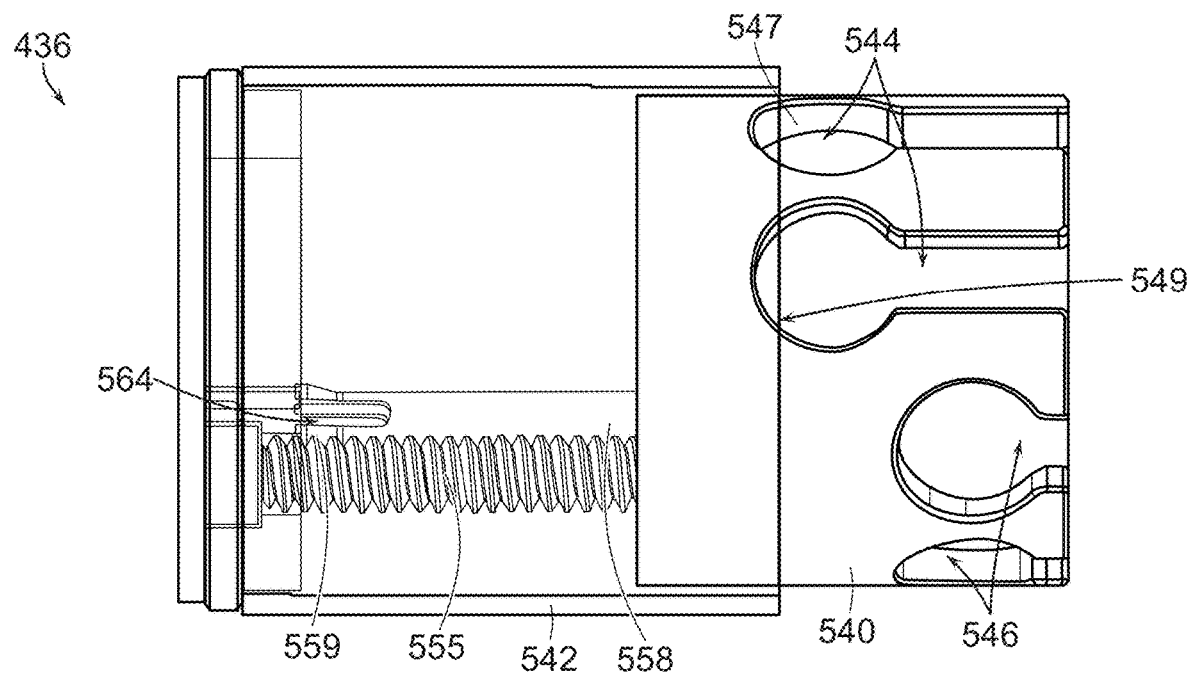
Figure 5F:
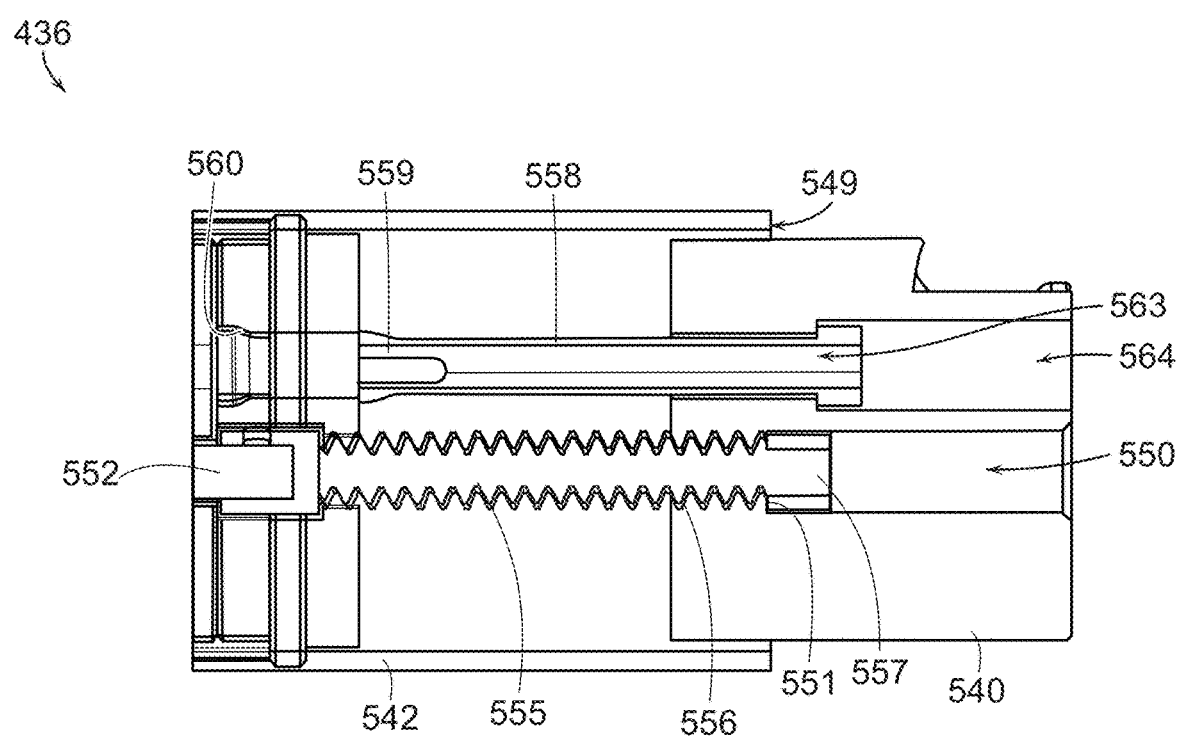

FIGS. 5A-5C are enlarged side views of the hub assembly 436 of FIG. 4 in a first position, a second position, and a third position, respectively, in accordance with embodiments of the present technology. FIGS. 5D-5F are side cross-sectional views of the hub assembly 436 in the first position, the second position, and the third position, respectively, in accordance with embodiments of the present technology. Referring first to FIGS. 5A and 5D together, the hub assembly 436 includes an inner hub component 540 and an outer hub component 542 (also referred to as a "capsule"). The outer hub component 542 is shown as partially transparent in FIGS. 5A-5F for the sake of clarity. The inner hub component 540 includes an outer surface 541, a proximal side or edge 543a, and a distal side or edge 543b. In the illustrated embodiment, the outer surface 541 of the inner hub component 540 includes a plurality/group of first recesses 544 and a plurality/group of second recesses 546 that extend from the distal edge 543b toward the proximal edge 543a. The first and second recesses 544, 546 are configured (e.g., shaped, sized, and/or positioned) to receive and secure corresponding ones of the connectors 205 of the implantable device 200 (FIGS. 2A and 2B). In some embodiments, the first and second recesses 544, 546 can have a generally similar shape including (i) a first portion 545 having a generally elongate (e.g., rectangular) shape for receiving a portion of a corresponding one of the struts 206 (FIGS. 2A and 2B) and (ii) a second portion 547 having a generally circular shape for receiving a corresponding one of the connectors 205 (FIGS. 2A and 2B). In other embodiments, the first and second recesses 544, 546 can have other suitable shapes for receiving and securing the connectors 205 and/or other features at the superior end portion S of the implantable device 200.

In the illustrated embodiment, the first recesses 544 are circumferentially spaced apart from the second recesses 546. That is, the first recesses 544 are positioned along/in a first circumferential portion of the outer surface 541, while the second recesses 546 are positioned along a second circumferential portion of the outer surface 541. In some embodiments, the first portions 545 of the second recesses 546 are shorter than the first portions 545 of the first recesses 544 (e.g., in a direction extending between the proximal and distal edges 543a, b). Accordingly, the second portions 547 of the second recesses 546 can be positioned closer to the distal edge 543b than the second portions 547 of the first recesses 544. In some embodiments, the first recesses 544 are configured to receive corresponding ones of the connectors 205 positioned at the anterior side portion A of the implantable device 200 (FIGS. 2A and 2B), while the second recesses 546 are configured to receive corresponding ones of the connectors 205 positioned at the posterior side portion P of the implantable device 200. As described in greater detail below with reference to FIGS. 5B, 5C, 5E, 5F and 11-12D, this arrangement can facilitate a two-stage release of the implantable device 200 in which the connectors 205 positioned at the posterior side portion P of the implantable device 200 are released from the hub assembly 436 before the connectors 205 positioned at the anterior side portion A of the implantable device 200. In some embodiments, the inner hub component 540 can include recesses that are aligned for a single-stage deployment, or recesses that are arranged around the outer surface 541 to facilitate deployment in three or more stages.

In the illustrated embodiment, the outer hub component 542 includes a distal opening 549 and, in the first position illustrated in FIGS. 5A and 5D, each of the first and second recesses 544, 546 are positioned proximal of the distal opening 549. Accordingly, in the first position, the connectors 205 of the implantable device 200 are secured/restrained in the first and second recesses 544, 546 by the outer hub component 542.

As best seen in FIG. 5D, the inner hub component 540 includes/defines a drive lumen 550 and a lock lumen 564 both extending at least partially from the proximal edge 543a toward the distal edge 543b. The drive lumen 550 includes a stepped stop surface 551 such that the drive lumen 550 has a larger dimension (e.g., diameter) distal of the stop surface 551. The drive lumen 550 further includes a threaded portion 553 proximal of the stop surface 551. Likewise, the lock lumen 564 includes a stepped or tapered stop surface 554 such that the lock lumen 564 has a larger dimension distal of the stop surface 554.

The hub assembly 436 can further include a lead screw 555 extending at least partially through the drive lumen 550 and operably coupling the inner hub component 540 to a drive shaft 552. More specifically, the lead screw 555 can include a threaded outer surface 556 configured to engage/mate with the threaded portion 553 of the drive lumen 550. In the illustrated embodiment, the lead screw 555 includes a stop member 557 configured (e.g., sized and/or shaped) to engage the stop surface 551 in the third position shown in FIGS. 5C and 5F. The drive shaft 552 can be coupled to the lead screw 555 via welding, adhesives, fasteners, and/or other suitable types of connections, or the drive shaft 552 and the lead screw 555 can be manufactured from a single piece of wire or rod.

As shown in FIGS. 5D-5F, the hub assembly 436 can further include a lock pin 558 extending at least partially through the lock lumen 564 and operably coupling the inner hub component 540 to the outer hub component 542. For example, the lock pin 558 can include a flared portion 559 configured to engage a corresponding stop surface 560 of the outer hub component 542 or another component coupled to the outer hub component 542. The lock pin 558 further includes a stop member 561 configured to engage the stop surface 554 of the lock lumen 564 in the second position shown in FIGS. 5B and 5E. In the illustrated embodiment, the lock pin 558 defines a release lumen 563 configured to receive a release shaft 562. A dimension (e.g., diameter) of the release lumen 563 can be slightly greater than a corresponding dimension of the release shaft 562 such that an outer surface of the release shaft 562 engages an inner surface of the lock pin 558 when the release shaft 562 is positioned within the release lumen 563. In some embodiments, (i) the release shaft 562 is formed from a rigid material, such as a nickel-titanium alloy, that does not compress easily while (ii) the flared portion 559 of the lock pin 558 is biased radially inward and/or formed of a relatively compressible material. Accordingly, when the release shaft 562 is positioned in the release lumen 563, the release shaft 562 can bias/force the flared portion 559 of the lock pin 558 radially outward such that the flared portion 559 remains in engagement with the stop surface 560 of the outer hub component 542 even when the lock pin 558 is urged distally. In other embodiments, the hub assembly 436 can include other locking mechanisms for inhibiting movement of the inner hub component 540.

Figure 6A:
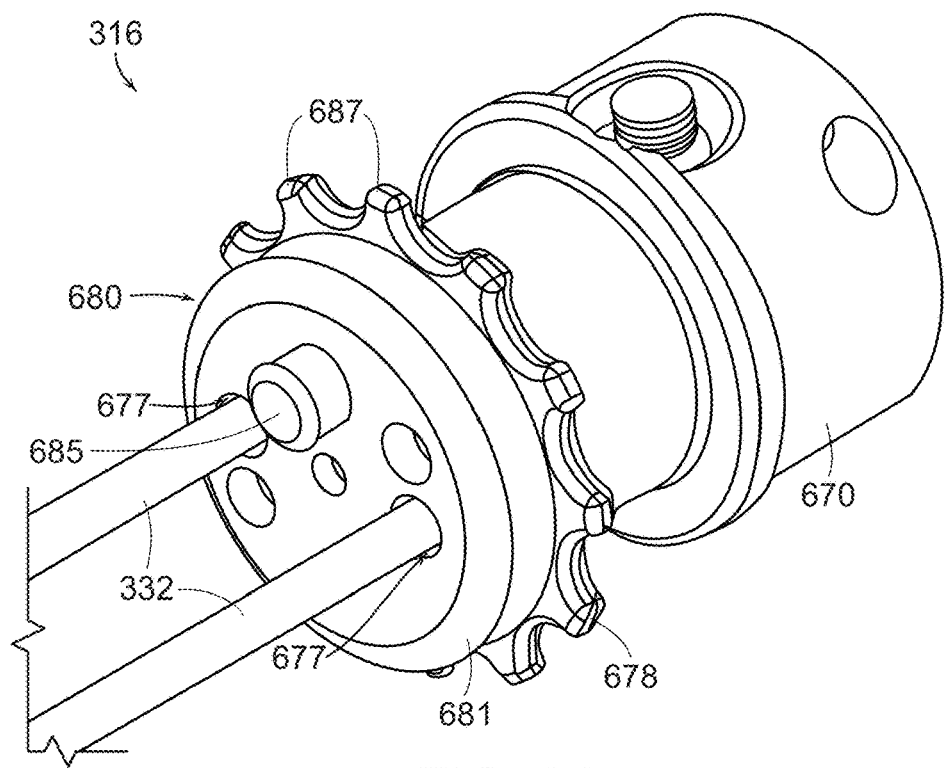
FIGS. 6A-6C are an isometric view, a partial cross-sectional proximally-facing isometric view, and a partially cross-sectional distally-facing isometric view, respectively, of a hub shaft handle of the delivery system of FIG. 3 in accordance with embodiments of the present technology.
Figure 6B:
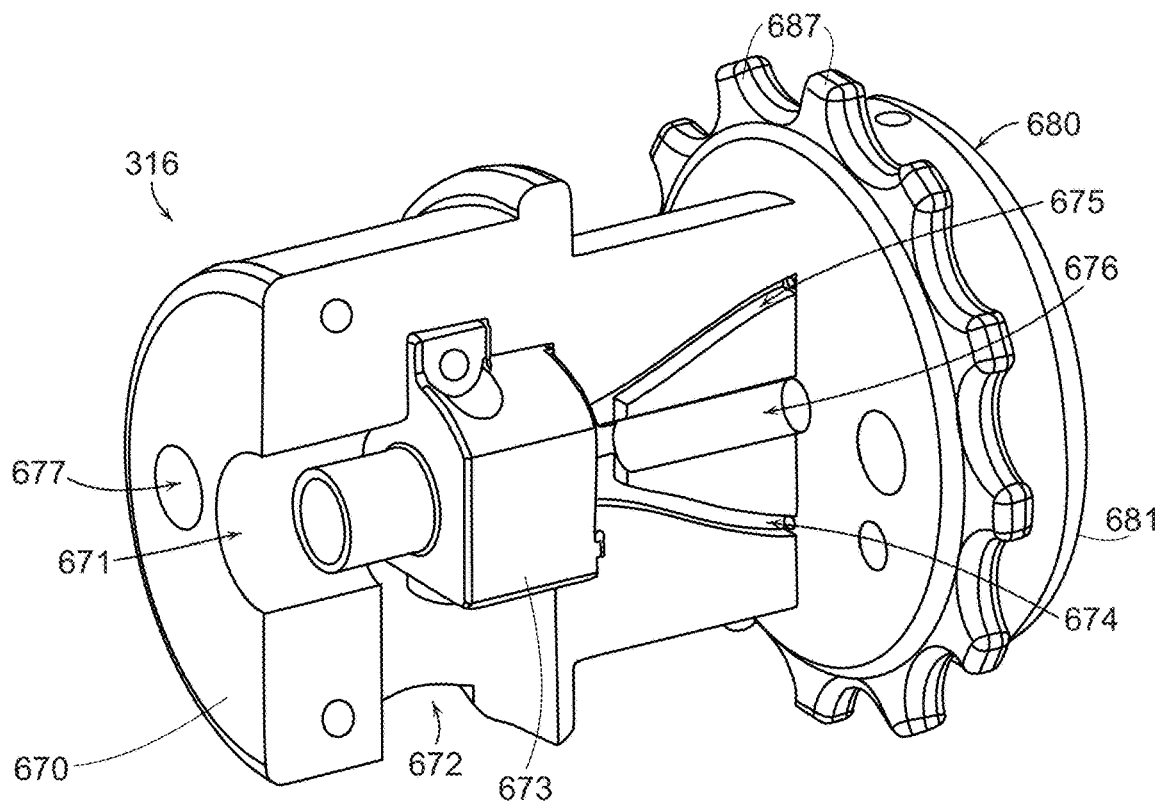
Figure 6C:
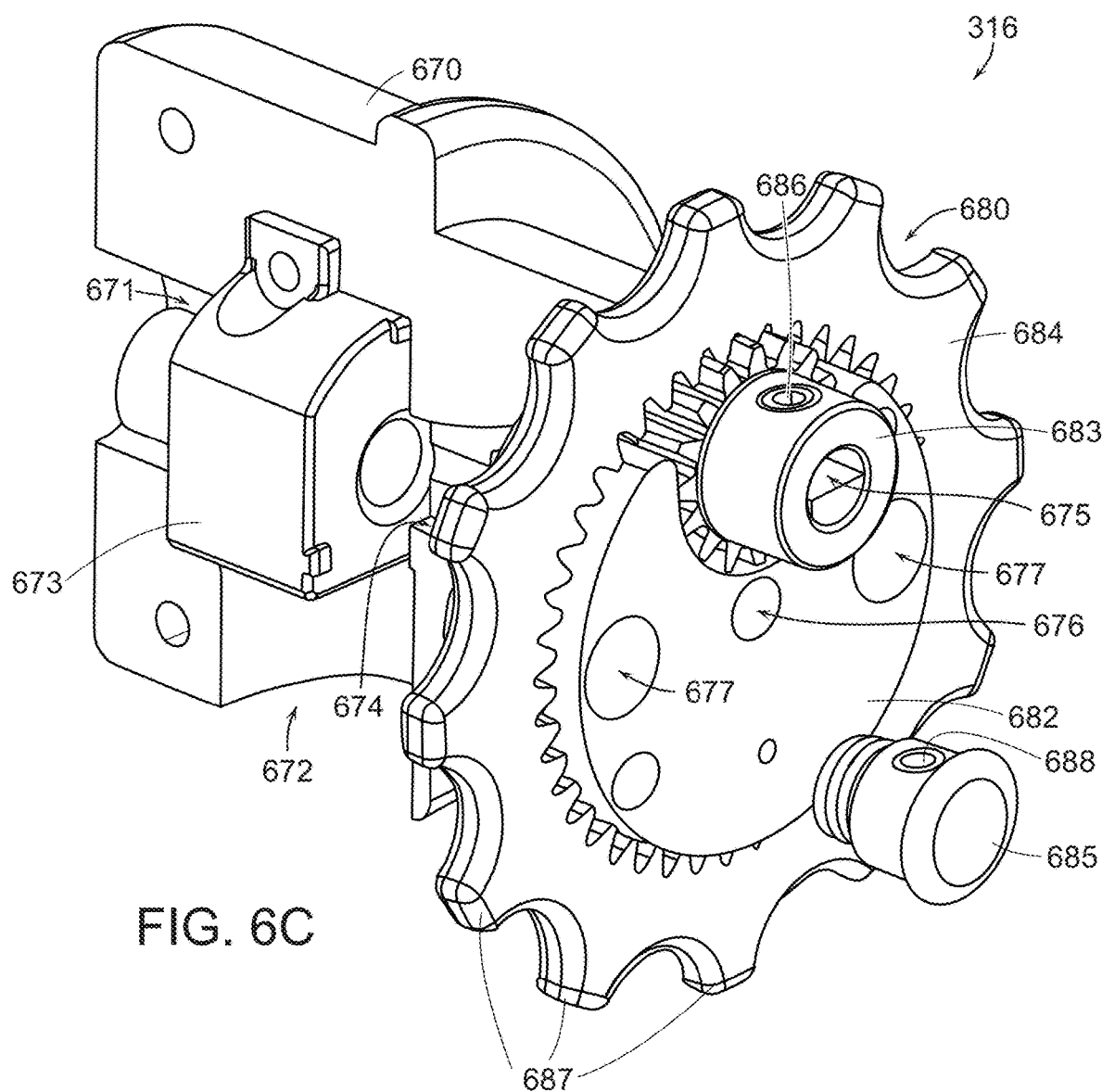

The drive shaft 552 and the release shaft 562 extend from the hub assembly 436, through the hub shaft 316 (FIG. 4), and to the hub shaft handle 326. FIGS. 6A-6C are an isometric view, a partially cross-sectional proximally-facing isometric view, and a partially cross-sectional distally-facing isometric view, respectively, of the hub shaft handle 326 in accordance with embodiments of the present technology. In general, the hub shaft handle 326 can be manipulated/actuated by a user to actuate the drive shaft 552 and/or the release shaft 562 to drive movement of the hub assembly 436 and release the connectors 205 of the implantable device 200 (FIGS. 2A and 2B) during device deployment.

Referring to FIGS. 6A-6C together, the hub shaft handle 326 includes a body component 670 coupled to a gear assembly 680. The body component 670 is shown as cross-sectional in FIGS. 6B and 6C. The body component 670 includes/defines a series of interconnected lumens including a hub shaft lumen 671 and a valve lumen 672. The hub shaft handle 326 can further include a hub shaft connector 673 (FIGS. 6B and 6C) positioned within the body component 670. The hub shaft 316 (FIG. 4; not shown in FIGS. 6A-6C for clarity) is configured to extend through the hub shaft lumen 671 and be secured to the hub shaft connector 673. The valve lumen 672 can receive one or more adaptors, valves, sealing members, etc., (not shown) that are configured for maintaining hemostasis and/or facilitating the ingress/egress of fluids (e.g., blood, priming solution, etc.) into the hub shaft 316. In some embodiments, for example, a duckbill hemostasis valve (not shown) is positioned in the valve lumen 672.

The gear assembly 680 includes a housing 681 (FIGS. 6A and 6B; omitted in FIG. 6C for clarity) that can at least partially enclose the following components shown in FIG. 6C: a body portion 682, a pinion gear 683, a ring gear 684, and a release member 685. The body component 670 and the gear assembly 680 (e.g., the housing 681, the body portion 682, and/or other components of the gear assembly 680) together include/define an additional series of interconnected lumens extending from the hub shaft connector 673 including (i) a release shaft lumen 674, (ii) a drive shaft lumen 675, (iii) a core shaft lumen 676, and (iv) one or more rail lumens 677. The core shaft 318 (FIG. 3; not shown in FIGS. 6A-6C for clarity) extends through the hub shaft 316, the hub shaft connector 673, and the core shaft lumen 676 to the core shaft handle 328 (FIG. 3). Accordingly, the core shaft 318 passes entirely through the hub shaft handle 326 and is independently movable relative to the hub shaft handle 326 and the hub shaft 316. The rail lumens 677 are configured to slidably receive the rails 332 (FIG. 3; omitted in FIGS. 6B and 6C for clarity).

The drive shaft 552 (FIGS. 5D-5F; not shown in FIGS. 6A-6C for clarity) extends through the hub shaft 316, the hub shaft connector 673, and the drive shaft lumen 675, and is fixedly coupled to the pinion gear 683. Referring to FIG. 6C, in some embodiments, the drive shaft 552 is secured to the pinion gear 683 via a set screw 686 and/or other suitable connection. The pinion gear 683 can be operably coupled to the ring gear 684 via, for example, the mating engagement of a plurality of teeth of the pinion gear 683 and the ring gear 684. The ring gear 684 is rotatable to rotate the pinion gear 683 to rotate the drive shaft 552. In some embodiments, the ring gear 684 includes a plurality of gripping features 687 around a perimeter thereof and that are accessible outside the housing 681. A user (e.g., a physician, other clinician, robotic or other automated mechanism), can manipulate the gripping features 687 to rotate the ring gear 684, thereby driving rotation of the drive shaft 552 to, for example, move the hub assembly 436 (FIGS. 5A-5F), as described in greater detail below. In some aspects of the present technology, the gripping features 687 accessible about its circumference to facilitate easy gripping and rotation of the ring gear 684. In some embodiments, the gear assembly 680 is configured to have a selected/selectable amount of frictional drag that inhibits rotation of the ring gear 684 to avoid rotation caused by inadvertent contact. These friction inducing features (e.g., compressed O-rings) and/or gear locks (not shown) operably coupled to the gear assembly 680 can avoid accidental rotation and promote only purposeful actuation of the gear assembly 680.

The release shaft 562 (FIGS. 5D-5F; not shown in FIGS. 6A-6C for clarity) extends through the hub shaft 316, the hub shaft connector 673, and the release shaft lumen 674, and is fixed to the release member 685 shown in FIG. 6C. The release shaft 562 can be secured to the release member 685 via a set screw 688, other mechanical connector, adhesive, welding, or other suitable connection. The release member 685 can be releasably coupled the gear assembly 680 and configured to be moved (e.g., pulled proximally) away from the gear assembly 680 to move the release shaft 562 in a proximal direction through the hub shaft handle 326. In some embodiments, the release member 685 includes one or more locking features (e.g., one or more threaded connections, compressed O-rings, press-fittings) that must be disengaged to permit movement of the release member 685 to, for example, inhibit or even prevent accidental disengagement of the release member 685.

The operation of the hub shaft handle 326 and the hub assembly 436 for deploying/releasing the implantable device 200 is now described with reference to FIGS. 2A, 2B, and 4-6C. During device delivery to a target site, the hub assembly 436 is in the first position shown in FIGS. 5A and 5D such that all the connectors 205 of the implantable device 200 are secured/restrained in the first and second recesses 544, 546 by the outer hub component 542. When the implantable device 200 is at the desired target site (e.g., at or near the mitral valve), the user can initiate deployment by moving the hub assembly 436 to the second position shown in FIGS. 5B and 5E by actuating (e.g., rotating) the ring gear 684 of the hub shaft handle 326 and, thereby, rotating the drive shaft 552. Rotation of the drive shaft 552 rotates the lead screw 555, which drives (e.g., linearly translates) the inner hub component 540 toward and partially out of the distal opening 549 of the outer hub component 542 via the engagement of the threaded outer surface 556 of the lead screw 555 with the threaded portion 553 of the drive lumen 550. In the second position, at least a portion of each second recess 546 (e.g., the second portions 547 of the second recesses 546) is positioned sufficiently distal of the distal opening 549 of the outer hub component 542 that the connectors 205 positioned at the posterior side portion P of the implantable device 200 are no longer constrained by the outer hub component 542, and thus free to disengage from the hub assembly 436. While in the second position with the posteriorly-positioned connectors 205 released, the second portions 547 of the first recesses 544 remain covered by the outer hub component 542 such that the connectors 205 positioned at the anterior side portion A of the implantable device 200 remain constrained by the outer hub component 542. Accordingly, moving the hub assembly 436 to second position disengages the struts 206 at the posterior side portion P of the atrial-fixation member 202 from the hub assembly 436—allowing them to expand—while inhibiting the struts 206 at the anterior side portion A of the atrial-fixation member 202 from disengaging the hub assembly 436 and expanding. In some embodiments, the hub assembly 436 has other configurations that allow for selective disengagement of the connectors 205 in a different manner or order, such as the anteriorly-positioned connectors 205 releasing before the posteriorly-positioned connectors 205.

In some embodiments, in the second position, the lock pin 558 inhibits further distal movement of the inner hub component 540 (e.g., to the third position shown in FIGS. 5C and 5F). For example, the release shaft 562 can bias the flared portion 559 of the lock pin 558 radially outward and into engagement with the stop surface 560 of the outer hub component 542, while the stop member 561 engages the stop surface 554 of the lock lumen 564. In some aspects of the present technology, the lock pin 558 and the release shaft 562 inhibit or even prevent inadvertent deployment of the struts 206 at the anterior side portion A of the atrial-fixation member 202 by inhibiting the first recesses 544 from being moved distally past the distal opening 549 of the outer hub component 542 (e.g., to the third position shown in FIGS. 5C and 5F).

To move the move the hub assembly 436 to the third position shown in FIGS. 5C and 5F, the user can first remove the release shaft 562 from the release lumen 563 of the lock pin 558 by moving (e.g., pulling) the release member 685 proximally away from the gear assembly 680 of the hub shaft handle 326. The user can then further actuate the ring gear 684 of the hub shaft handle 326 to drive the drive shaft 552 to rotate. Removing the release shaft 562 removes the outward biasing force provided by the release shaft 562 when the flared portion 559 is urged inward, and thereby permits the flared portion 559 of the lock pin 558 to move (e.g., flex) radially inward and past the stop surface 560 of the outer hub component 542 when the drive shaft 552 and the lead screw 555 drive the inner hub component 540 distally. In the third position, the first recesses 544 (e.g., the second portions 547 of the first recesses 544) are positioned sufficiently distal of the distal opening 549 of the outer hub component 542 that the connectors 205 positioned at the anterior side portion A of the implantable device 200 are no longer constrained by the outer hub component 542, and are thus free to disengage the hub assembly 436. Accordingly, moving the hub assembly 436 to third position disengages the struts 206 at the anterior side portion A of the atrial-fixation member 202 from the hub assembly 436, allowing them to expand. Therefore, in some aspects of the present technology the hub assembly 436 is configured to provide for a controlled, two-stage release of the atrial-fixation member 202 in which the struts 206 at the posterior side portion P are released from the hub assembly 436 and allowed to expand before the struts 206 at the anterior side portion A. In additional aspects of the present technology, the hub assembly 436 allows for the controlled and staged release of the atrial-fixation member 202 from the distal end of the delivery system 310 (FIG. 3) and is not affected or minimally affected by factors such as catheter shaft compression, curving, and the like that could make it difficult to control the release of the atrial-fixation member 202 with the same precision via control from the proximal end of the delivery system 310.

Figure 7A:
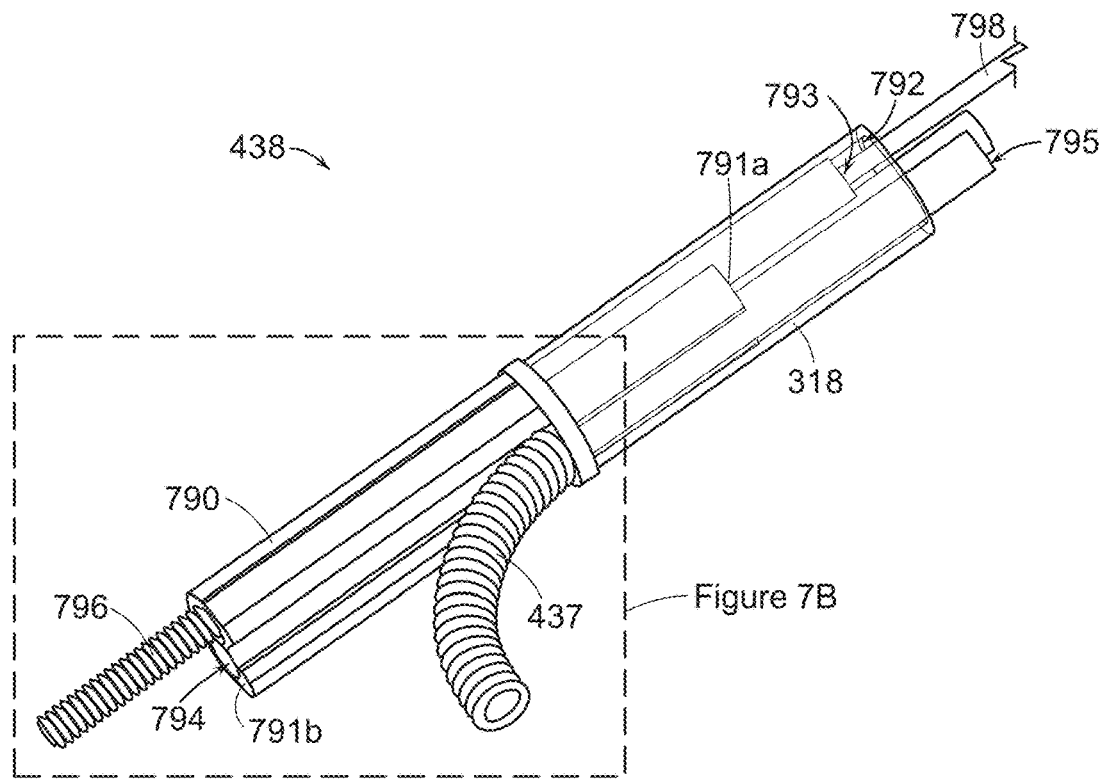
FIGS. 7A and 7B are an isometric side view and an enlarged partial cross-sectional side view, respectively, of a distal plug on a core shaft of the delivery system of FIG. 3 in accordance with embodiments of the present technology.
Figure 7B:
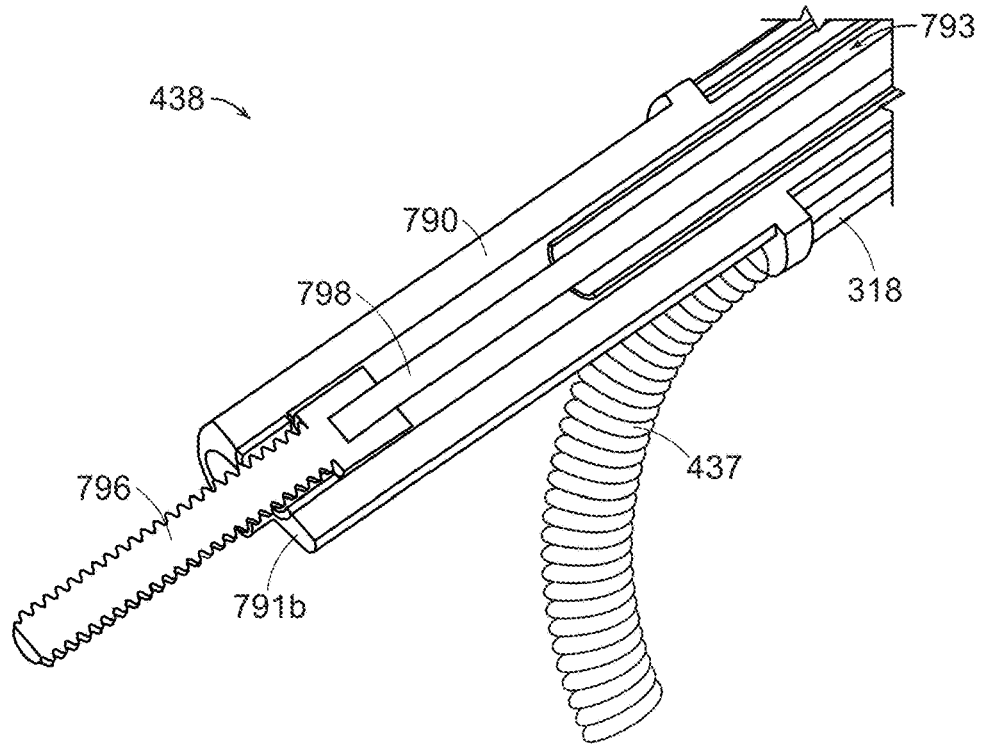

FIGS. 7A and 7B are a partially-transparent isometric side view and an enlarged partially cross-sectional side view, respectively, of the plug assembly 438 at the distal end portion of the delivery system 310 of FIGS. 3 and 4 in accordance with embodiments of the present technology. Referring to FIGS. 7A and 7B together, the plug assembly 438 includes a plug housing 790 configured to be secured to/at a distal terminus of the core shaft 318. The plug housing 790 includes a proximal end portion 791*a* and a distal end portion 791*b*. In some embodiments, a section of the plug housing 790 extends at least partially into a lumen 792 defined by the core shaft 318 and can be secured thereto via a friction-fit arrangement, adhesive, laser-weld, fasteners, and/or other suitable attachment mechanisms.

The plug assembly 438 further includes/defines a plurality of lumens including a drive lumen 793, a clip tendon lumen 794, and a cinch tendon lumen 795 (collectively "lumens 793-795"). In the illustrated embodiment, the lumens 793-795 are defined by tubes coupled to the plug housing 790 and that extend distally into the lumen 792 of the core shaft 318. In some embodiments, the tubes are short, flexible tubes while, in other embodiments the tubes can be rigid or semi-rigid and/or can extend through the entire length of the core shaft 318. In other embodiments, the lumens 793-795 can be defined solely within the plug housing 790 and/or can extend through a wall of the core shaft 318. For example, the plug housing 790 can be a single-piece, such as a plastic extrusion, that defines each of the lumens 793-795.

The clip tendon lumen 794 is configured to receive a first elongated flexible element, such as a suture, string, and/or a wire (e.g., a clip tendon 821 shown in FIG. 8C) for actuating the clip 209 of the baffle 204 (FIGS. 2A and 2B), as described in further detail below. The cinch tendon lumen 795 extends distally to the flexible tube 437 and is configured to receive a second elongated flexible element, such as a cinch tendon 439 (FIG. 4) for controlling expansion and contraction of the atrial-fixation member 202. In some embodiments, one or both of the first and second elongated flexible elements (e.g., the clip and cinch tendons) can extend from the proximal portion of the delivery system 310 (FIG. 3) to the distal end portion, where they form a loop around an element (e.g., connection features on the clip 209 (FIG. 2A) and/or the atrial-fixation member 202 (FIGS. 2A and 2B)), and then extend back up through the delivery system 310 to the proximal end (e.g., referred to as "double-length suture loops"). In these embodiments, the clip tendon lumen 794 and/or the cinch tendon lumen 795 carry two sections of the elongated flexible elements, and in certain embodiments the tubes carrying the flexible elements divide the lumens 794, 795 into separate channels that carry the individual sections of the elongated flexible members to avoid entanglement or excessive friction.

In the illustrated embodiment, the plug assembly 438 includes a baffle connection member 796, such as a threaded shaft (e.g., a screw), secured to the plug housing 790 in a distal portion of the drive lumen 793 and extending out of the drive lumen 793 beyond the distal end portion 791*b* of the plug housing 790. In some embodiments, the baffle connection member 796 is rotatably coupled within the drive lumen 793. With additional reference to FIG. 4, the baffle connection member 796 is configured to extend through the opening 201 in the baffle 204 to releasably engage the delivery attachment member 203 (e.g., via a threaded connection) to secure the core shaft 318 to the baffle 204 of the implantable device 200. A drive shaft 798 can extend through the drive lumen 793 to operably couple the baffle connection member 796 to an actuation means (e.g., a wheel, knob, button) at the proximal portion of the delivery system 310 (FIG. 3), which can be actuated to impart rotation on the baffle connection member 796, thereby disengaging the baffle connection member 796 from the delivery attachment member 203. The drive shaft 798 can be coupled to the baffle connection member 796 via welding, adhesives, fasteners, and/or other suitable types of connections, or be manufactured from a single piece of wire.

The clip tendon, the cinch tendon 439, and the drive shaft 798 extend from the plug assembly 438, through the core shaft 318, and to the core shaft handle 328. FIGS. 8A-8D are a distally-facing isometric view, a partially transparent side view, a partially transparent top view, and a partially transparent proximally-facing isometric view, respectively, of the core shaft handle 328 configured in accordance with embodiments of the present technology. In general, the core shaft handle 328 is configured to be manipulated/actuated by a user to individually actuate (i) the clip tendon to open/close the clip 209 (FIGS. 2A and 2B), (ii) the drive shaft 798 to unscrew the baffle connection member 796 (FIGS. 7A and 7B) from the baffle 204 (FIGS. 2A and 2B), and (iii) the cinch tendon 439 to cinch/uncinch the atrial-fixation member 202 (FIGS. 2A and 2B).

Referring to FIGS. 8A-8D together, the core shaft handle 328 includes a core shaft housing 802 and a plurality of actuators coupled to the core shaft housing 802, including, for example, a baffle actuator 804, a clip actuator 806, and a cinch actuator 808. The housing 802 is shown as partially transparent in FIGS. 8B-8D. The housing 802 and/or other components of the core shaft handle 328 define a series of interconnected lumens including a core shaft lumen 812, a valve lumen 814, and an actuation lumen 816 (collectively "lumens 812-816"). The core shaft handle 328 further includes a core shaft connector 818 positioned between the lumens 812-816. The core shaft 318 is configured to extend through the core shaft lumen 812 and be secured to the core shaft connector 818. The valve lumen 814 is configured to receive a valve 819 and/or one or more additional adaptors, valves, sealing members, and/or other fluid control components for, for example, maintaining hemostasis, facilitating the ingress/egress of fluids (e.g., blood, priming solution, saline) into the core shaft 318, etc. The rails 332 can be secured to the housing 802 and/or other components of the core shaft handle 328 to slidably couple the core shaft handle 328 to the hub shaft handle 326 (FIG. 3).

The drive shaft 798 can extend through the core shaft 318, the core shaft connector 818, and into the actuation lumen 816 where it is secured to the baffle actuator 804. The baffle actuator 804 is accessible to a user via the housing 802 at a proximal portion of the core shaft handle 328 and is actuatable to drive the drive shaft 798. In the illustrated embodiment, for example, the baffle actuator 804 can be rotated to rotate the drive shaft 798. Accordingly, with additional reference to FIGS. 4, 7A, and 7B, a user (e.g., a physician) can grip and rotate the baffle actuator 804 to impart rotation onto the drive shaft 798, which in turn rotates the baffle connection member 796 to disengage the baffle connection member 796 from the delivery attachment member 203 and, thereby, disengages/detaches the baffle 204 from the core shaft 318.

In the illustrated embodiment, the core shaft handle 328 includes a clip mount assembly 820 and a cinch mount assembly 830 slidably positioned within the actuation lumen 816. The clip mount assembly 820 is operably coupled to the clip actuator 806 and the cinch mount assembly 830 is operably coupled to the cinch actuator 808. FIGS. 8E-8H are a partially transparent side view, a proximally-facing front view, a distally-facing isometric view, and another distally-facing isometric view, respectively, of the clip mount assembly 820 and the cinch mount assembly 830 configured in accordance with embodiments of the present technology. The cinch mount assembly 830 is in (i) a relaxed (e.g., first, non-tensioned, minimally-tensioned) configuration in FIGS. 8E and 8G and (ii) a tensioned (e.g., second) configuration in FIGS. 8F and 8H.

Figure 8A:
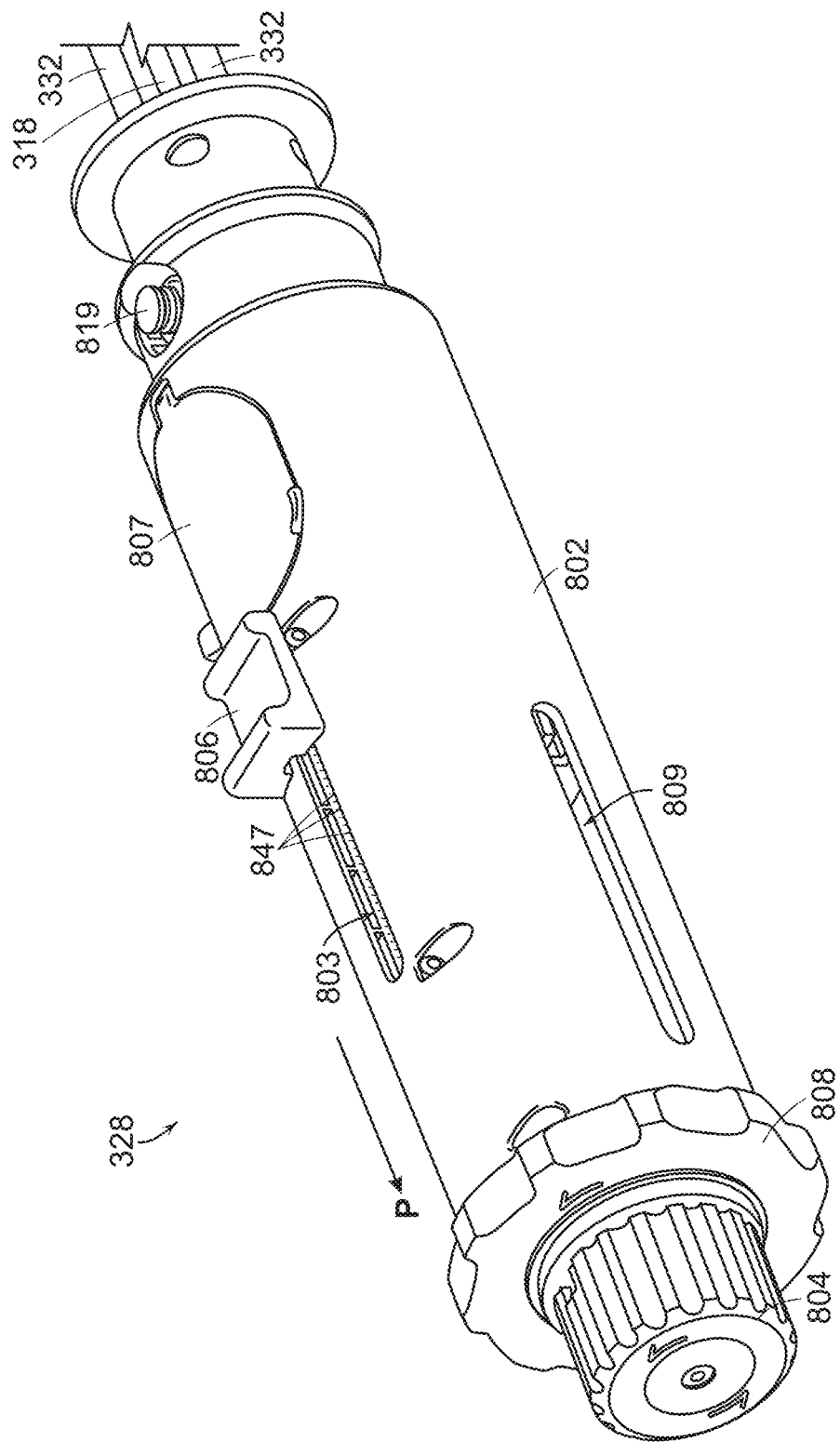
FIGS. 8A-8D are a distally-facing isometric view, a partially transparent side view, a partially transparent enlarged top view, and a partially transparent proximally-facing isometric view, respectively, of a core shaft handle of the delivery system of FIG. 3 in accordance with embodiments of the present technology.
Figure 8B:
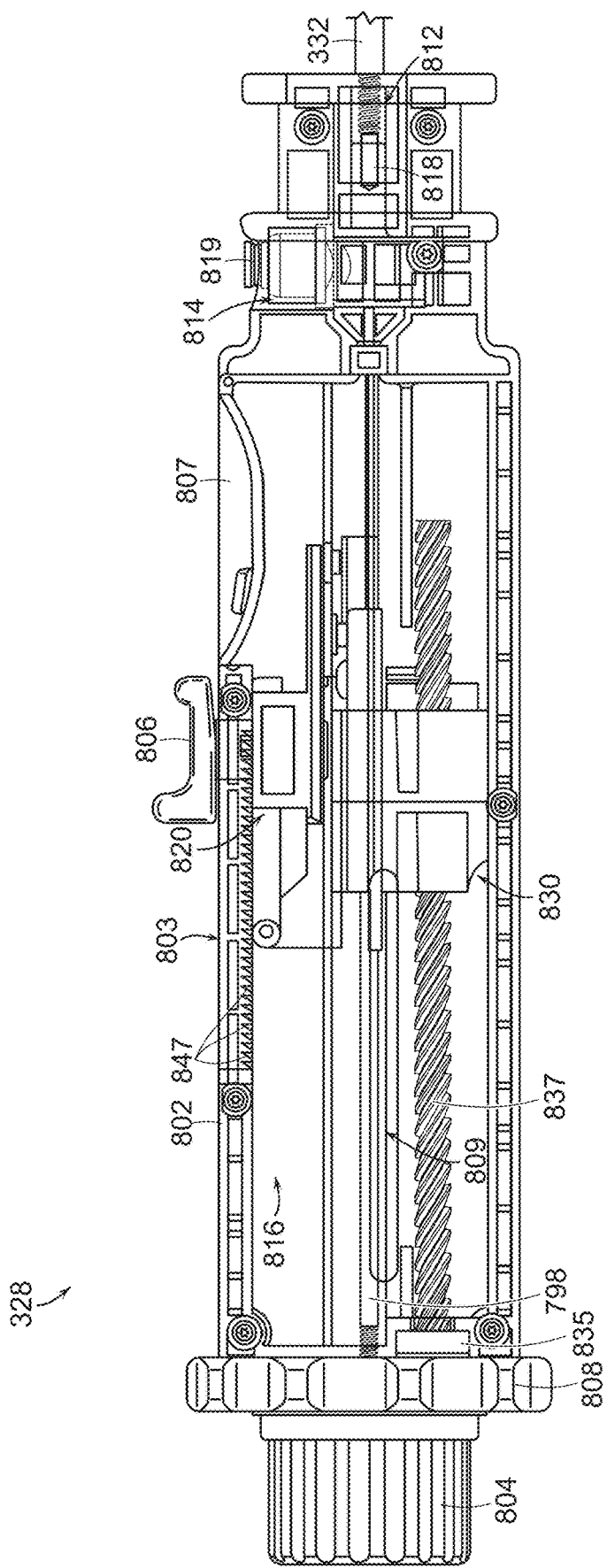
Figure 8C:
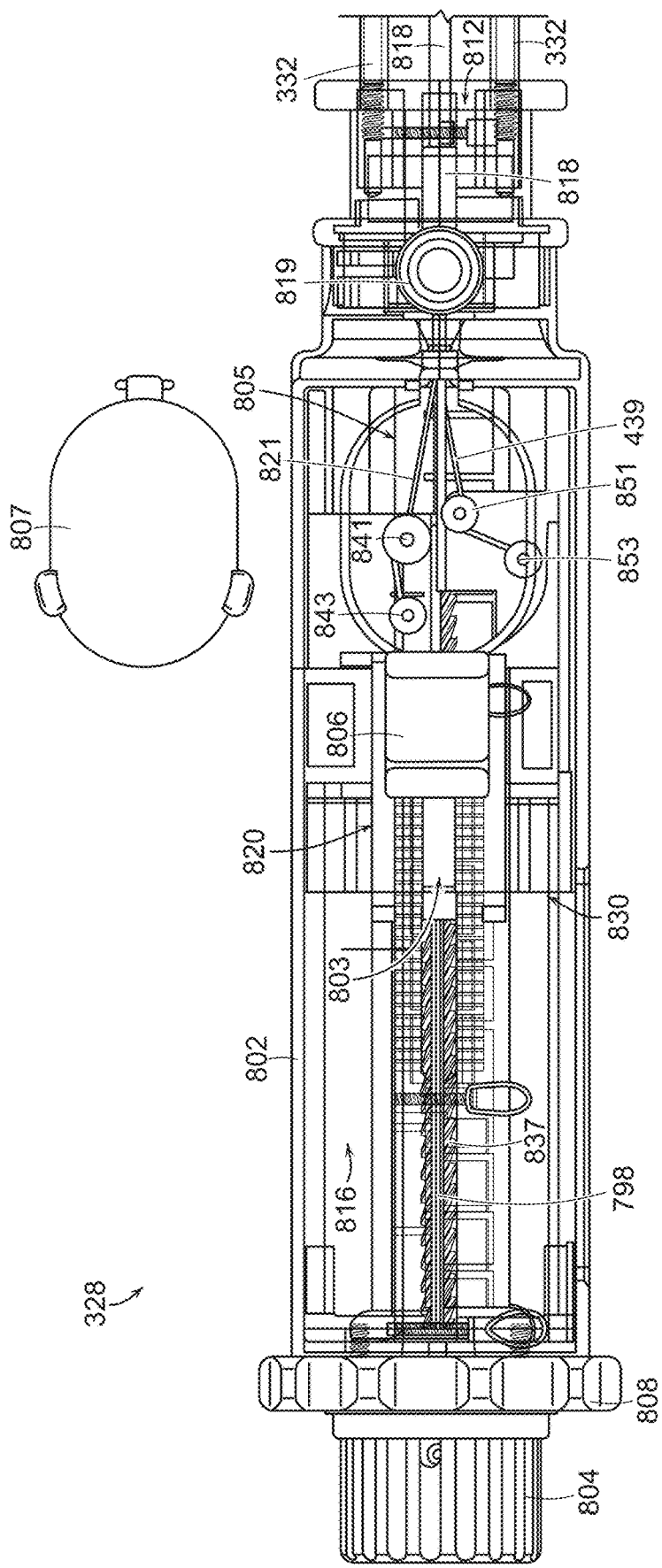
Figure 8D:
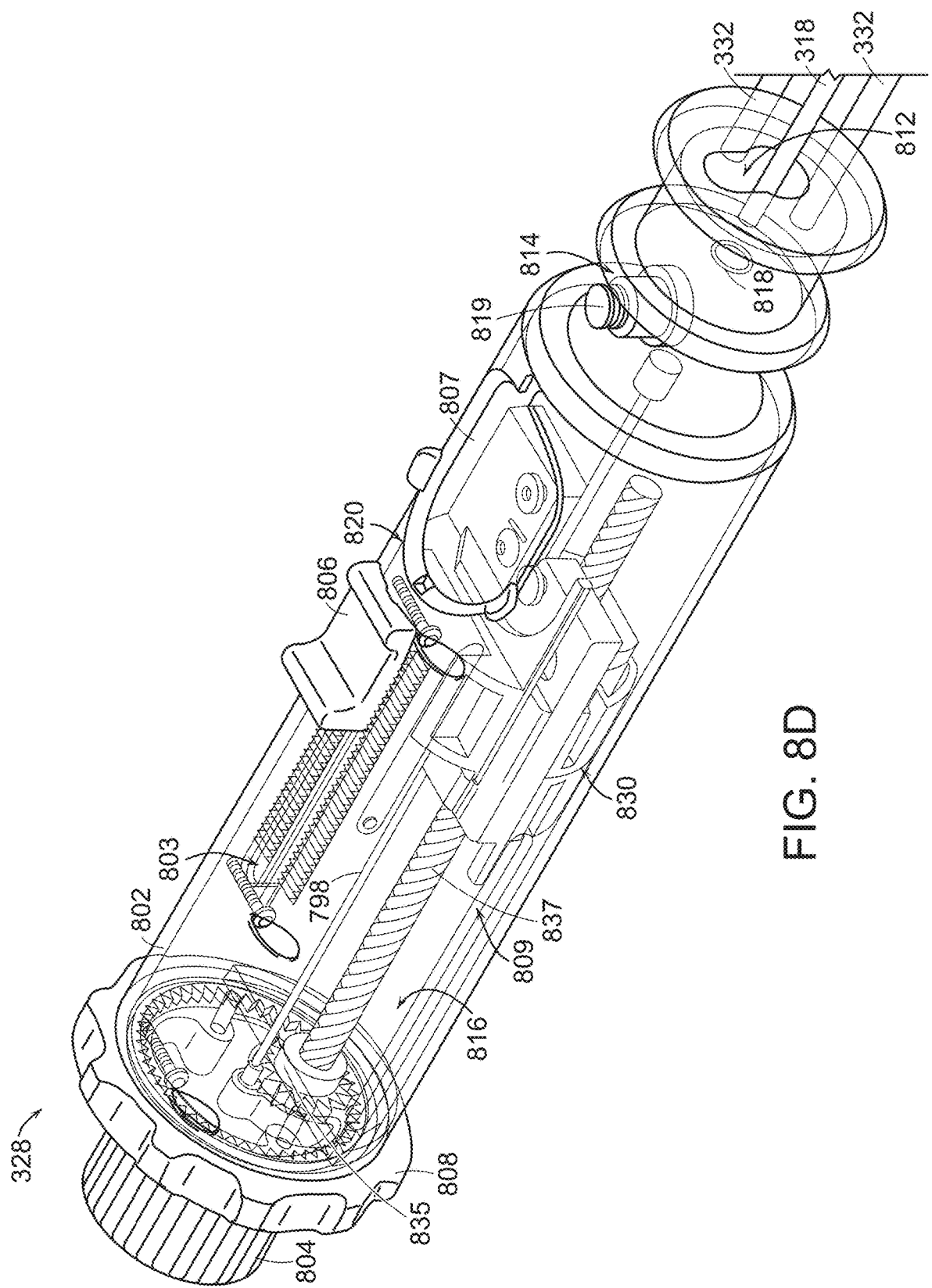
Figure 8E:
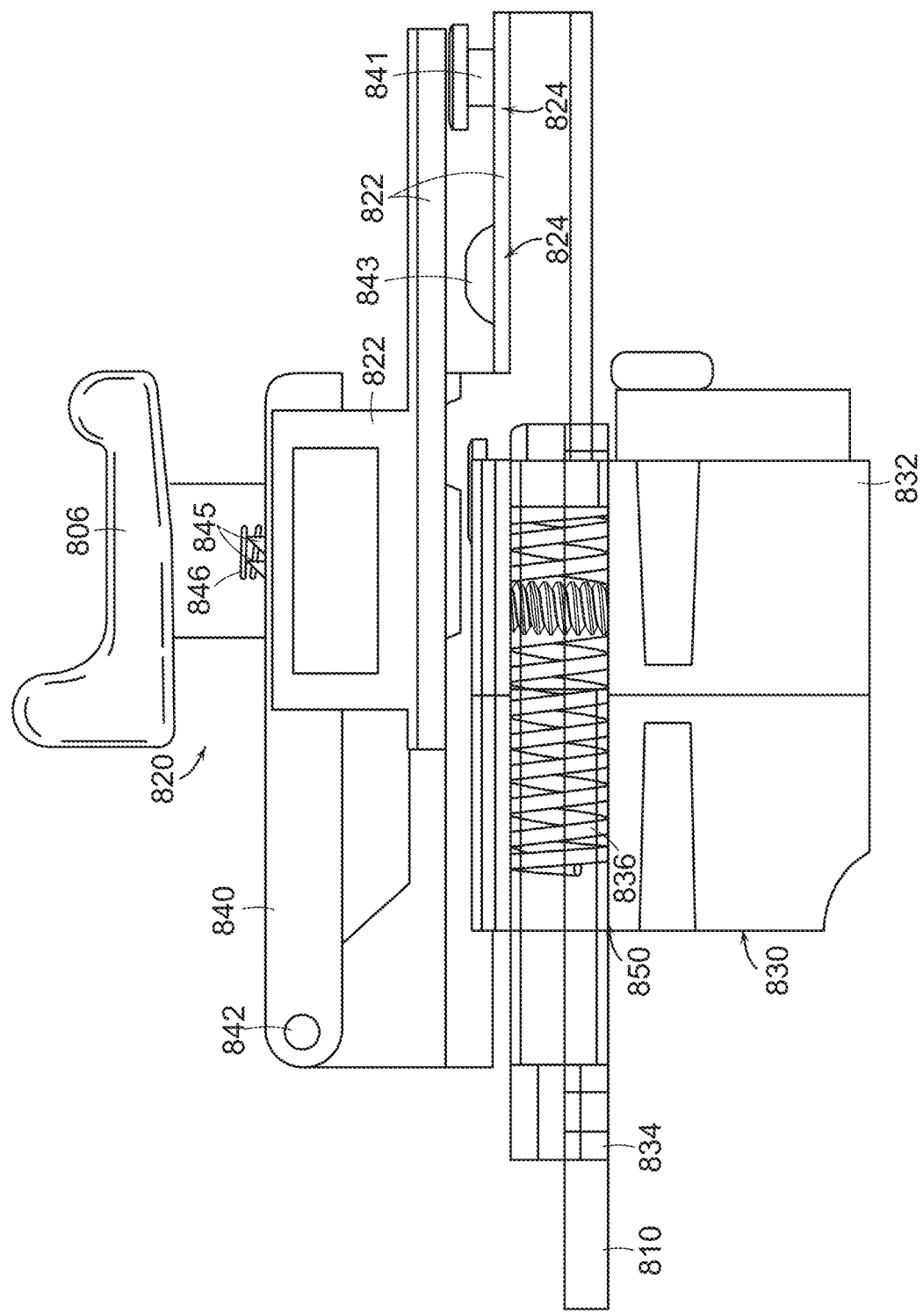
FIGS. 8E-8H are a partially transparent side view, a proximally-facing front view, a distally-facing isometric view, and another distally-facing isometric view, respectively, of a clip mount assembly and a cinch mount assembly of the core shaft handle of FIGS. 8A-8D configured in accordance with embodiments of the present technology.
Figure 8F:
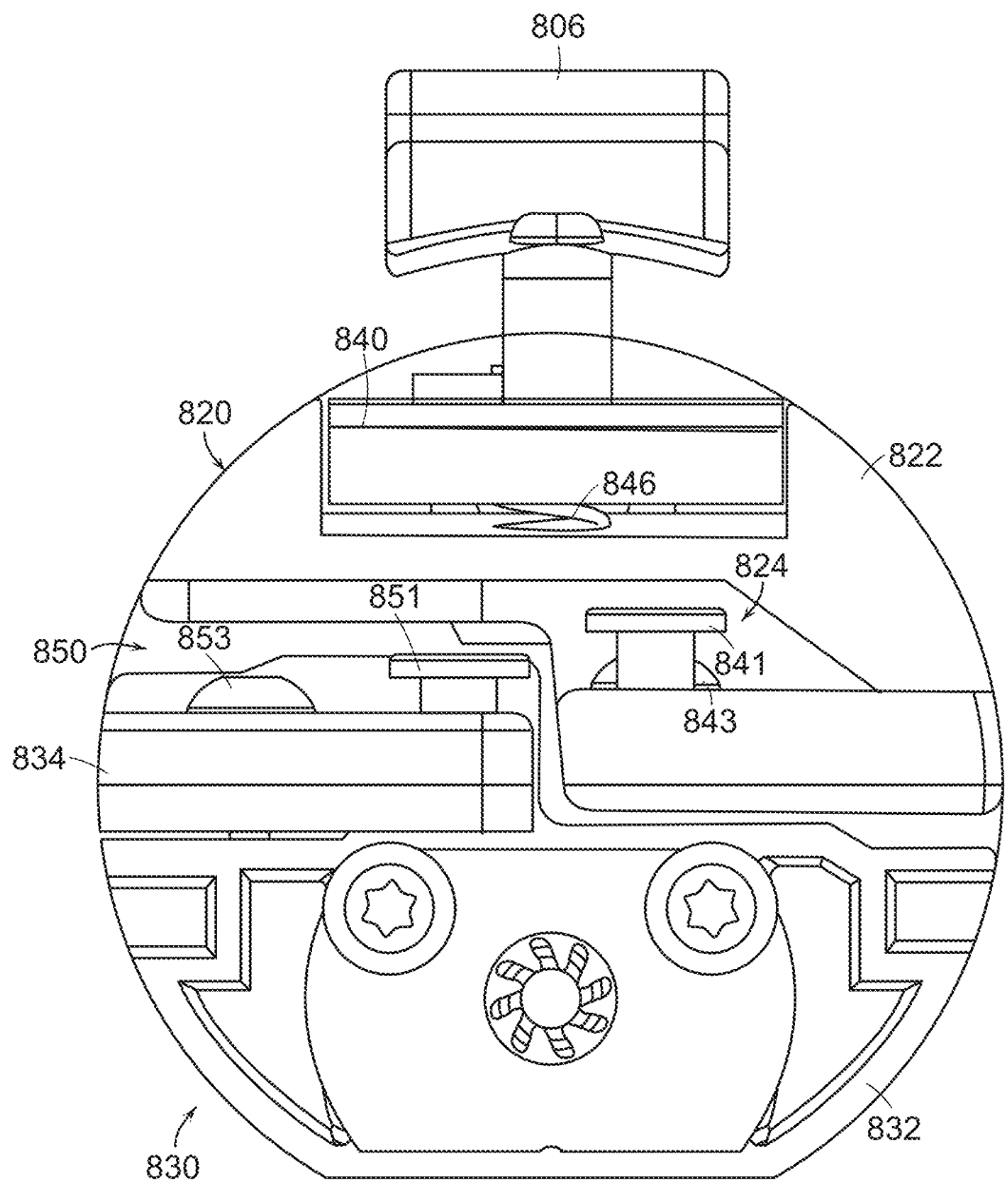
Figure 8G:
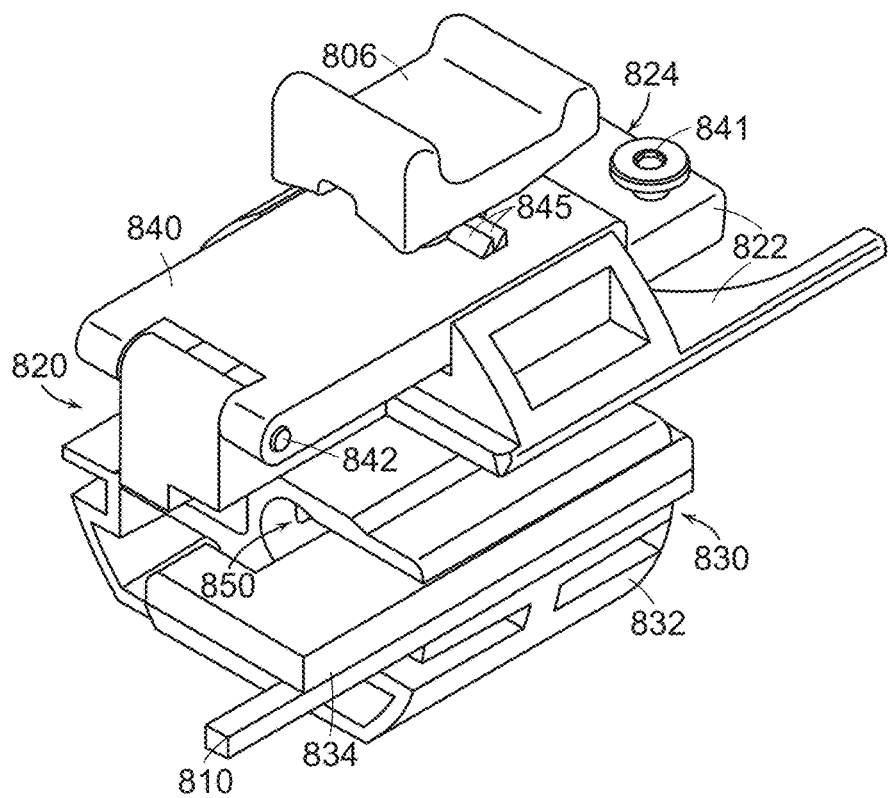
Figure 8H:
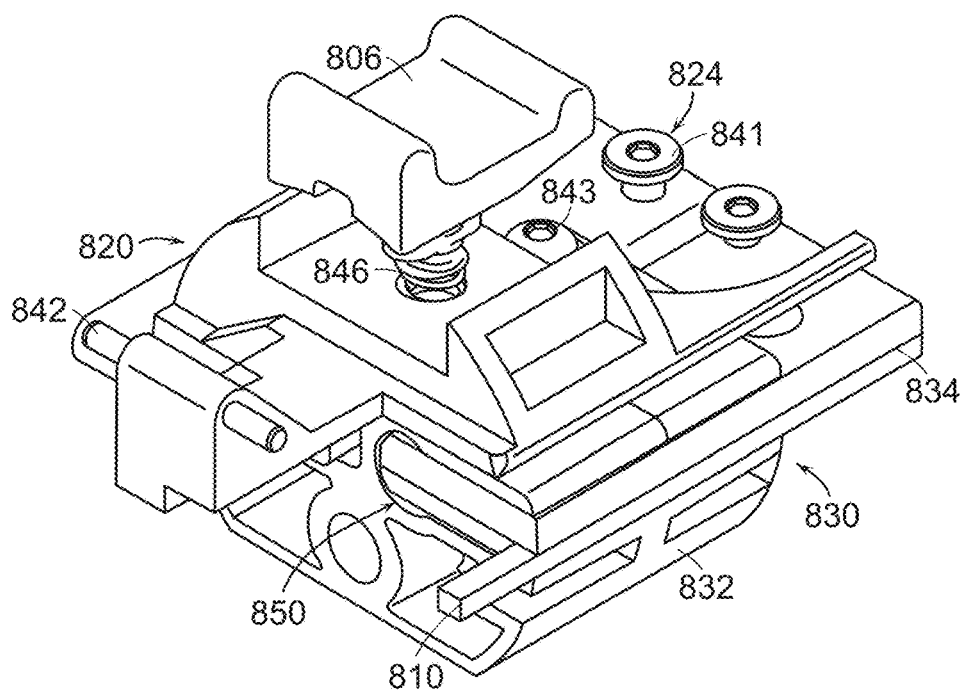

Referring to FIGS. 8E-8H together, the clip mount assembly 820 can include a body 822, a clip tendon mount 824 fixed to the body 822, and a latch 840 movably (e.g., pivotally) coupled to the body 822 via, for example, a shaft 842. The latch 840 is omitted in FIG. 8H for clarity. The clip actuator 806 can be coupled to the latch 840 and slidably mounted to a first slot 803 (FIGS. 8A-8D) extending through/along the housing 802. With additional reference to FIG. 8C, the clip tendon (e.g., a clip tendon 821 shown in FIG. 8C) extends through the core shaft 318, the core shaft connector 818, and into the actuation lumen 816 where it is releasably coupled to the clip tendon mount 824. In the illustrated embodiment, for example, the clip tendon mount 824 comprises a post 841 and a screw 843. The clip tendon 821 can be a double-length suture loop that is wound around the post 841 (e.g., one time, two times, ten times, more than ten times) and then secured to the body 822 via the screw 843. As best seen in FIGS. 8E and 8H, the latch 840 can include a plurality of first engagement features 845 (e.g., teeth, grooves) and can be operably coupled to the body 822 via a biasing member 846, such as a compression spring. As best seen in FIGS. 8A and 8B, the housing 802 can include a plurality of second engagement features 847 (e.g., teeth, grooves) positioned adjacent to the first slot 803 within the actuation lumen 816. Referring to FIGS. 8A, 8B, 8E, and 8H together, the biasing member 846 can normally bias the first engagement features 845 into engagement with the second engagement features 847 to inhibit movement of the clip actuator 806 and the clip mount assembly 820 along the first slot 803. To move the clip mount assembly 820 through the actuation lumen 816, a user can depress the clip actuator 806 against the biasing force of the biasing member 846 to disengage the first engagement features 845 from the second engagement features 847 and then slide the clip actuator 806 along the first slot 803.

Referring again to FIGS. 8A-8D together, during a delivery procedure, actuation of the clip actuator 806 can drive the clip mount assembly 820 within the actuation lumen 816 to drive/tension the clip tendon 821 to open/close the clip 209 (FIG. 2B). More specifically, FIGS. 8A-8D illustrate the clip actuator 806 in a first position in which the clip actuator 806 is positioned proximate a distal end portion of the first slot 803. In operation, the user can depress the clip actuator 806 and slide the clip actuator 806 along the first slot 803 toward a second position proximate a proximal end portion of the first slot 803 (e.g., in a direction indicated by arrow P in FIG. 8A). This proximal movement of the clip actuator 806 can pull the clip tendon 821 to open the clip 209. Likewise, distal movement of the clip actuator 806 can release the force/tension on the clip tendon 821, thereby allowing the normally-closed clip 209 to close. In some embodiments, the first slot 803 can have a length selected to correspond to a specific opening/closing stroke of the clip 209. For example, a position of the distal end portion of the first slot 803 can be selected to correspond to a fully-closed position of the clip 209 and/or a position of the proximal end portion of the first slot 803 can be selected to correspond to a fully-open position of the clip 209. In other embodiments, the core shaft handle 328 can include other features for actuating the clip tendon 821 to open/close the clip 209, such as one or more buttons, levers, knobs, sliders, and/or other actuation members.

Referring again to FIGS. 8E-8H together, the cinch mount assembly 830 can include a body 832, a cinch tendon mount 834 (shown partially transparent in FIG. 8E for clarity), and a biasing member 836 (FIG. 8E) operably coupling the cinch tendon mount 834 to the body 832. In the illustrated embodiment, the body defines a channel 850 and the cinch tendon mount 834 is slidably mounted within the channel 850. With additional reference to FIG. 8C, the cinch tendon 439 (FIG. 8C) extends through the core shaft 318, the core shaft connector 818, and into the actuation lumen 816 where it is coupled to the cinch tendon mount 834. In the illustrated embodiment, for example, the clip tendon mount 824 includes a post 851 and a screw 853 (both obscured in FIGS. 8E and 8H), and the cinch tendon 439 can be wound around the post 851 and further secured (e.g., clamped) via the screw 853.

Referring again to FIGS. 8A-8D together, the cinch actuator 808 can be a ring gear that is accessible from the housing 802 for actuation by a user. The cinch actuator 808 can be operably coupled to the cinch mount assembly 830 via a pinion gear 835 and a lead screw 837. More specifically, the pinion gear 835 can be coupled to the cinch actuator 808 via, for example, the mating engagement of a plurality of teeth of the pinion gear 835 and the cinch actuator 808. The pinion gear 835 can be fixedly mounted to the lead screw 837, which can threadedly engage the cinch mount assembly 830 (e.g., the body 832). Accordingly, with additional reference to FIG. 4, the user can grip and rotate the cinch actuator 808 to (i) drive the lead screw 837 to rotate, (ii) drive the cinch mount assembly 830 to move (e.g., translate) within the actuation lumen 816, and (iii) drive/tension the cinch tendon 439 to cinch/uncinch the atrial-fixation member 202 of the implantable device 200 (FIGS. 2A and 2B). For example, the cinch mount assembly 830 is in a first position in FIGS. 8A-8D in which the cinch mount assembly 830 is positioned proximate a distal portion of the actuation lumen 816. In operation, rotation of the cinch actuator 808 in a first direction can drive the cinch mount assembly 830 proximally through the actuation lumen 816 to pull the cinch tendon 439 proximally to radially compress the atrial-fixation member 202. Conversely, rotation of the cinch actuator 808 in a second direction can drive the cinch mount assembly 830 distally through the actuation lumen 816 to relax the cinch tendon 439 to permit the atrial-fixation member 202 to radially expand.

Referring to FIGS. 8A-8H together, in some embodiments the biasing member 836 stores energy (e.g., becomes "loaded") as the cinch mount assembly 830 is driven proximally through the actuation lumen 816. In some embodiments, the biasing member 836 can be a compression spring that compresses due to the opposing forces between the body 832 (e.g., via the lead screw 837) and the cinch tendon mount 834 (e.g., via the cinch tendon 439). In the illustrated embodiment, the cinch tendon mount 834 includes a cinch indicator portion 810 that can be viewed through, for example, a second slot 809 extending through/along the housing 802. A distance between the cinch indicator portion 810 of the cinch tendon mount 834 and the body 832 can indicate a relative amount of cinching. For example, in the relaxed position shown in FIGS. 8E and 8G, the biasing member 836 can bias the cinch tendon mount 834 away from the body 832—increasing the distance between the cinch indicator portion 810 and the body 832. Conversely, in the tensioned position shown in FIGS. 8F and 8H, the cinching forces can compress the biasing member 836—decreasing the distance between the cinch indicator portion 810 and the body 832. Accordingly, the user can view the positioning of the cinch indicator portion 810 along the second slot 809 to determine an amount of cinching.

In additional aspects of the present technology, the biasing member 836 of the cinch mount assembly 830 is configured to spring-load the cinch tendon 439 such that tension is maintained on the cinch tendon 439 during manipulation of the delivery system 310. With additional reference to FIGS. 2A and 2B, this can inhibit or even prevent unwanted cinching/uncinching of the atrial-fixation member 202. In some embodiments, for example, actuating the cinch actuator 808 to cinch the implantable device 200 can load the biasing member 836 such that the biasing member 836 can take up any slack in the cinch tendon 439 during manipulation of the delivery system 310. In other embodiments, the core shaft handle 328 can include other features for actuating the cinch tendon 439 to cinch/uncinch the implantable device 200, such as one or more buttons, levers, knobs, sliders, and/or other actuators. For example, in some embodiments the cinch tendon 439 can be actuated via the same or a similar arrangement as the clip tendon 821 (e.g., via sliding movement of the cinch actuator 808 along the housing 802).

In some embodiments, the clip tendon mount 824 of the clip mount assembly 820 and the cinch tendon mount 834 of the cinch mount assembly 830 are each nearly aligned with a longitudinal axis/centerline of the core shaft handle 328. This arrangement can help ensure that the tension/drive forces on the cinch tendon 439 and the clip tendon 821 (collectively "tendons 439, 821") are relatively aligned along the axes of the tendons 439, 821 and help inhibit shear or other forces that could prematurely break the tendons 439, 821. In some aspects of the present technology, the clip mount assembly 820 and the cinch mount assembly 830 are independently movable through the actuation lumen 816. For example, in the illustrated embodiment the body 822 of the clip mount assembly 820 and the body 832 of the cinch mount assembly 830 each have complementary shapes (e.g., generally L-shapes) that allow the clip and cinch mount assemblies 820, 830 to move through the actuation lumen 816 without interfering with one another. In other embodiments, the clip and cinch mount assemblies 820, 830 can be operably coupled to move together.

Referring to FIG. 8C, the housing 802 can further include an opening 805 configured (e.g., shaped, sized, and/or positioned) to provide access to the tendons 439, 821. In operation, for example, the user can remove the tendons 439, 821 by (i) cutting the tendons 439, 821 by inserting a cutting tool through the opening 805 and (ii) pulling the tendons 439, 821 out of the opening 805. In other embodiments, the core shaft handle 328 can have other features for cutting and/or removing the tendons 439, 821. In some embodiments, the housing 802 further includes a removable cover 807 that can be releasably secured over the opening 805 (e.g., via a snap-fit arrangement) to conceal the tendons 439, 821 and enclose the internal features the core shaft handle 328.

Figure 14A:
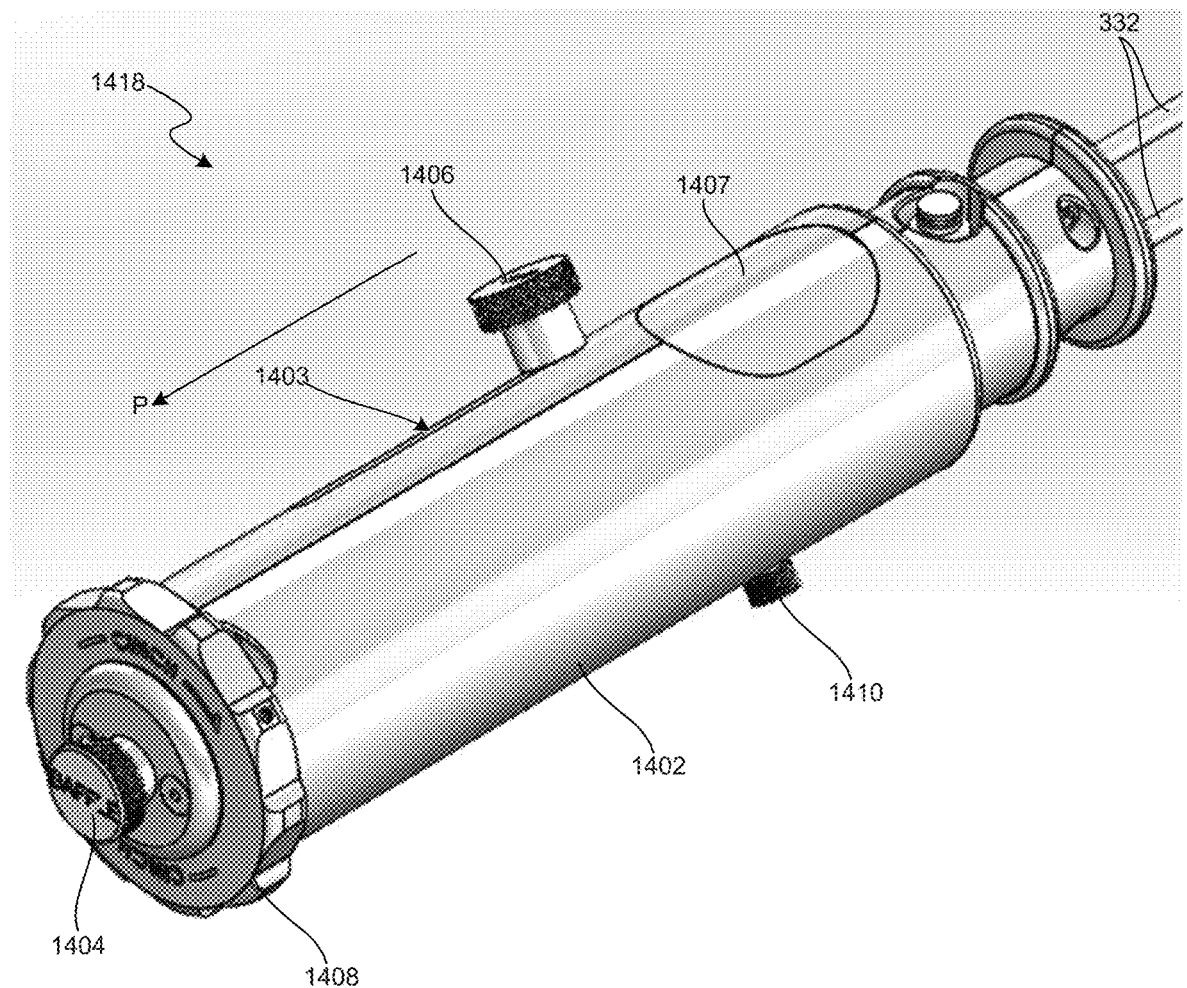

FIGS. 14A-14D are a distally-facing isometric view, a partially transparent side view, a partially transparent enlarged side view, and a partially transparent proximally-facing isometric view, respectively, of a core shaft handle 1428 configured in accordance with additional embodiments of the present technology. The core shaft handle 1428 can (i) include several features generally similar or identical to the core shaft handle 328 described in detail above with reference to FIGS. 8A-8H, (ii) operate generally similarly or identically to the core shaft handle 328, and/or (iii) can be integrated into the system 310 in a generally similar or identical manner. Referring to FIGS. 14A-14D together, the core shaft handle 1428 includes a core shaft housing 1402 and a plurality of actuators coupled to the core shaft housing 1402, including, for example, a baffle actuator 1404, a clip actuator 1406, and a cinch actuator 1408. The housing 1402 and/or other components of the core shaft handle 1428 define a series of interconnected lumens including a core shaft lumen 1412, a valve lumen 1414, and an actuation lumen 1416 (collectively "lumens 1412-1416"). As best seen in FIG. 14B, the core shaft handle 1428 further includes a core shaft connector 1418 positioned between the lumens 1412-1416. The core shaft 318 (FIG. 3; not shown in FIGS. 14A-8D for the sake of clarity) is configured to extend through the core shaft lumen 1412 and be secured to the core shaft connector 1418. The valve lumen 1414 is configured to receive one or more adaptors, valves, sealing members, and/or other fluid control components (not shown) for, for example, maintaining hemostasis, facilitating the ingress/egress of fluids (e.g., blood, priming solution, saline) into the core shaft 318, and the like. As best seen in FIGS. 14A and 14B, the rails 332 can be secured to the housing 1402 and/or other components of the core shaft handle 1428 to slidably couple the core shaft handle 1428 to the hub shaft handle 326.

The drive shaft 798 can extend through the core shaft 318, the core shaft connector 1418, and into the actuation lumen 1416 where it is secured to the baffle actuator 1404. The baffle actuator 1404 is accessible to a user via the housing 1402 at a proximal portion of the core shaft handle 1428 and is actuatable to drive the drive shaft 798. In the illustrated embodiment, for example, the baffle actuator 1404 can be rotated to rotate the drive shaft 798. Accordingly, with additional reference to FIGS. 4, 7A, and 7B, a user (e.g., a physician) can grip and rotate the baffle actuator 1404 to impart rotation onto the drive shaft 798, which in turn rotates the baffle connection member 796 to disengage the baffle connection member 796 from the delivery attachment member 203 and, thereby, disengages/detaches the baffle 204 from the core shaft 318.

In the illustrated embodiment, the core shaft handle 1428 includes a clip mount assembly 1420 slidably positioned within the actuation lumen 1416. The clip tendon (e.g., a clip tendon 1421 shown in FIG. 14C) extends through the core shaft 318, the core shaft connector 1418, and into the actuation lumen 1416 where it is releasably coupled to the clip mount assembly 1420. In some embodiments, the clip mount assembly 1420 includes a body 1422, a clip tendon mount 1424, and a biasing member 1426 operably coupling the clip tendon mount 1424 to the body 1422. The body 1422 is shown as partially transparent in FIGS. 14B and 14D for clarity. The clip actuator 1406 can be slidably mounted to a first slot 1403 extending through/along the housing 1402, and is operably coupled to the clip mount assembly 1420 through the first slot 1403. In the illustrated embodiment, the clip tendon 1421 is a double-length suture loop that extends through an eyelet 1423 in the clip tendon mount 1424.

During a delivery procedure, actuation of the clip actuator 1406 can drive the clip mount assembly 1420 within the actuation lumen 1416 to drive/tension the clip tendon 1421 to open/close the clip 209 (FIG. 2B). More specifically, FIGS. 14A-14D illustrate the clip actuator 1406 in a first position in which the clip actuator 1406 is positioned proximate a distal end portion of the first slot 1403. In operation, the user can grip the clip actuator 1406 and slide the clip actuator 1406 along the first slot 1403 toward a second position proximate a proximal end portion of the first slot 1403 (e.g., in a direction indicated by arrow P in FIG. 14A). This proximal movement of the clip actuator 1406 can pull the clip tendon 1421 to open the clip 209. Likewise, distal movement of the clip actuator 1406 can release the force/tension on the clip tendon 1421, thereby allowing the normally-closed clip 209 to close. In some embodiments, the first slot 1403 can have a length selected to correspond to a specific opening/closing stroke of the clip 209. For example, a position of the distal end portion of the first slot 1403 can be selected to correspond to a fully-closed position of the clip 209 and/or a position of the proximal end portion of the first slot 1403 can be selected to correspond to a fully-open position of the clip 209. In some embodiments, the biasing member 1426 stores energy (e.g., becomes "loaded") as the clip mount assembly 1420 is driven proximally through the actuation lumen 1416. In various embodiments, the core shaft handle 1428 can include other features for actuating the clip tendon 1421 to open/close the clip 209, such as one or more buttons, levers, knobs, sliders, and/or other actuation members.

Figure 14D:
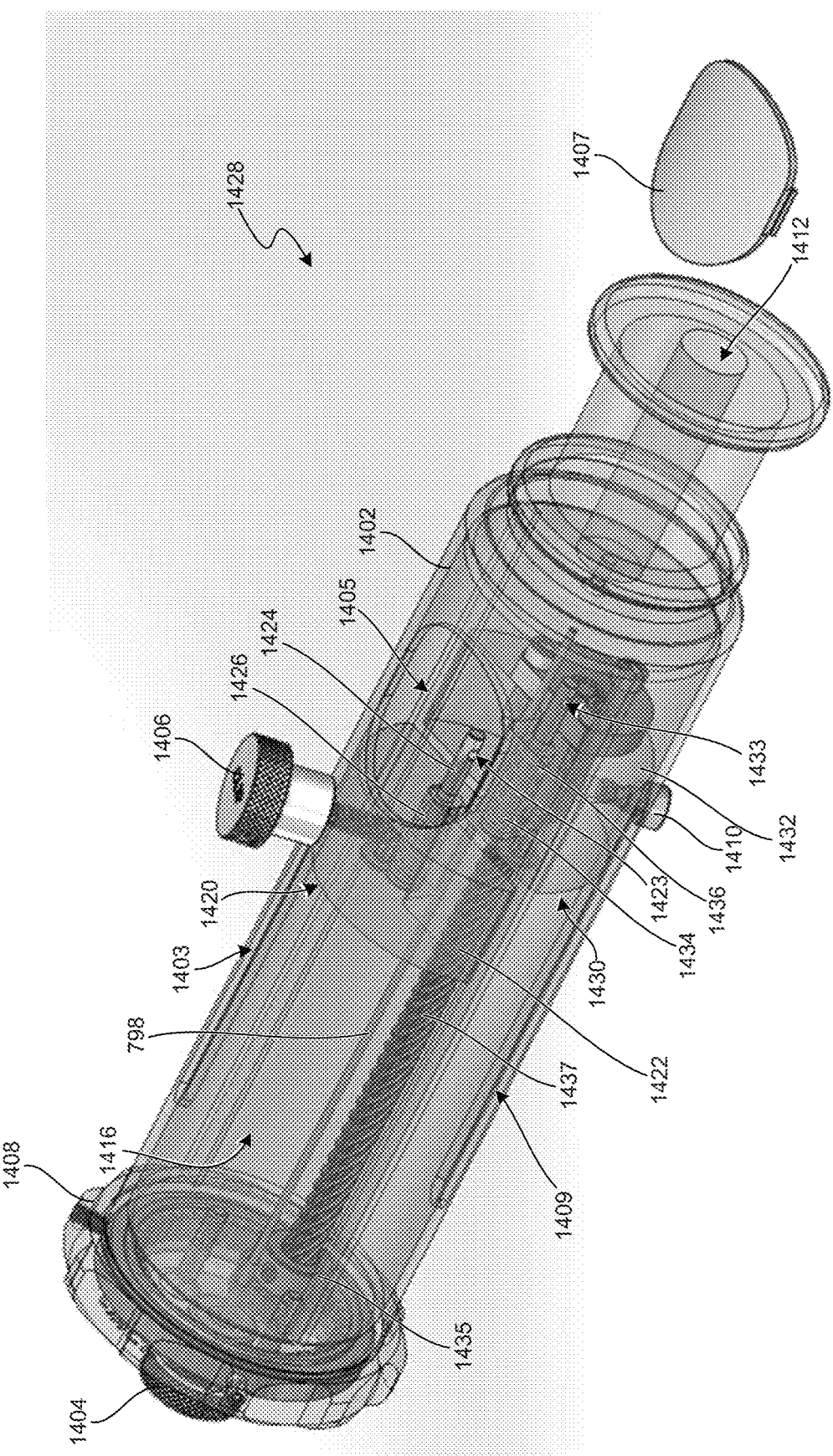

As further shown in FIGS. 14B-14D, the core shaft handle 1428 can also include a cinch mount assembly 1430 slidably positioned within the actuation lumen 1416. The cinch mount assembly 1430 can include features generally similar or identical to those of the clip mount assembly 1420. In the illustrated embodiment, for example, the cinch mount assembly 1430 includes a body 1432 (shown partially transparent in FIGS. 14B and 14D for clarity), a cinch tendon mount 1434, and a biasing member 1436 operably coupling the cinch tendon mount 1434 to the body 1432. The cinch tendon 439 extends through the core shaft 318, the core shaft connector 1418, and into the actuation lumen 1416 where it is coupled to the cinch tendon mount 1434 via an eyelet 1433 formed therein.

In some embodiments, as best seen in FIG. 14D, the cinch actuator 1408 is a ring gear that is accessible from the housing 1402 for actuation by a user. The cinch actuator 1408 can be operably coupled to the cinch mount assembly 1430 via a pinion gear 1435 and a lead screw 1437. More specifically, the pinion gear 1435 can be coupled to the cinch actuator 1408 via, for example, the mating engagement of a plurality of teeth of the pinion gear 1435 and the cinch actuator 1408. The pinion gear 1435 can be fixedly mounted to the lead screw 1437, which can threadedly engage the cinch mount assembly 1430 (e.g., the body 1432). Accordingly, with additional reference to FIG. 4, the user can grip and rotate the cinch actuator 1408 to (i) drive the lead screw 1437 to rotate, (ii) drive the cinch mount assembly 1430 to move (e.g., translate) within the actuation lumen 1416, and (iii) drive/tension the cinch tendon 439 to cinch/uncinch the atrial-fixation member 202 of the implantable device 200. For example, the cinch mount assembly 1430 is in a first position in FIGS. 14A-14D in which the cinch mount assembly 1430 is positioned proximate a distal portion of the actuation lumen 1416. In operation, rotation of the cinch actuator 1408 in a first direction can drive the cinch mount assembly 1430 proximally through the actuation lumen 1416 to pull the cinch tendon 439 proximally to radially compress the atrial-fixation member 202 (FIGS. 2A and 2B). Conversely, rotation of the cinch actuator 1408 in a second direction can drive the cinch mount assembly 1430 distally through the actuation lumen 1416 to relax the cinch tendon 439 to permit the atrial-fixation member 202 to radially expand. In some embodiments, the biasing member 1436 stores energy (e.g., becomes "loaded") as the cinch mount assembly 1430 is driven proximally through the actuation lumen 1416.

In various embodiments, the core shaft handle 1428 can include other features for actuating the cinch tendon 439 to cinch/uncinch the implantable device 200, such as one or more buttons, levers, knobs, sliders, and/or other actuators. For example, in some embodiments the cinch tendon 439 can be actuated via the same or a similar arrangement as the clip tendon 1421 (e.g., via sliding movement of the cinch actuator 1408 along the housing 1402).

In some aspects of the present technology, the clip mount assembly 1420 and the cinch mount assembly 1430 are independently movable through the actuation lumen 1416. For example, in the illustrated embodiment the body 1422 of the clip mount assembly 1420 and the body 1432 of the cinch mount assembly 1430 each have complementary shapes (e.g., semi-circular cross-sectional shapes) that allow the clip and cinch mount assemblies 1420, 1430 to move through the actuation lumen 1416 without interfering with one another. In other embodiments, the clip and cinch mount assemblies 1420, 1430 can be operably coupled to move together.

In another aspect of the present technology, the biasing member 1426 of the clip mount assembly 1420 and the biasing member 1436 of the cinch mount assembly 1430 are configured to spring-load the clip tendon 1421 and the cinch tendon 439 (collectively "tendons 439, 1421"), respectively, such that tension is maintained on the tendons during manipulation of the delivery system 310. With additional reference to FIGS. 2A and 2B, this can inhibit or even prevent unwanted actuation of the clip 209 or cinching/uncinching of the atrial-fixation member 202. In some embodiments, for example, actuating the cinch actuator 1408 to cinch the implantable device 200 can load the biasing member 1436 such that the biasing member 1436 can take up any slack in the cinch tendon 439 during manipulation of the delivery system 310. In another aspect of the present technology, the clip tendon mount 1424 of the clip mount assembly 1420 and the cinch tendon mount 1434 of the cinch mount assembly 1430 are each nearly aligned with a longitudinal axis/centerline of the core shaft handle 1428. This arrangement can help ensure that the tension/drive forces on the tendons 439, 1421 are relatively aligned along the axes of the tendons 439, 1421 and help inhibit shear or other forces that could prematurely break the tendons 439, 1421.

Referring to FIGS. 14B and 14D together, the housing 1402 can further include an opening 1405 configured (e.g., shaped, sized, and/or positioned) to provide access to the tendons 439, 1421. In operation, for example, the user can remove the tendons 439, 1421 by (i) cutting the tendons 439, 1421 by inserting a cutting tool through the opening 1405 and (ii) pulling the tendons 439, 1421 out of the opening 1405. In other embodiments, the core shaft handle 1428 can have other features for cutting/removing the tendons 439, 1421. In some embodiments, the housing 1402 further includes a removable cover 1407 (FIGS. 14A, 14C, and 14D) that can be releasably secured over the opening 1405 (e.g., via a snap-fit arrangement) to conceal the tendons 439, 1421 and enclose the internal features the core shaft handle 1428.

In the illustrated embodiment, a cinch indicator 1410 is coupled to the cinch mount assembly 1430 and extends at least partially out of a second slot 1409 extending through/along the housing 1402. For example, the cinch indicator 1410 can be coupled to the body 1432 of the cinch mount assembly 1430 via a threaded fastener or other suitable fastener. In operation, the cinch indicator 1410 moves along the second slot 1409 as the cinch actuator 1408 drives movement of the cinch mount assembly 1430 through the actuation lumen 1416. The user can view the position of the cinch indicator 1410 along the second slot 1409 to determine an amount of cinching. In some embodiments, the second slot 1409 can have a length selected to provide a maximum/minimum amount of cinching of the atrial-fixation member 202. For example, a position of a distal end portion of the second slot 1409 can be selected to correspond to a minimum amount of cinching and/or a position of a proximal end portion of the second slot 1409 can be selected to correspond to a maximum amount of cinching. In some embodiments, the cinch indicator 1410 can inhibit or even prevent rotation of the cinch mount assembly 1430 within the actuation lumen 1416.

Referring to FIGS. 3-8H and 13A-14D together, the various components of the delivery system 310 can be formed from metals (e.g., stainless steel, nickel-titanium alloys, etc.), plastics, and/or other suitable materials. The various components can be manufactured using three-dimensional printing, injection molding, machining, and/or other suitable processes known in the art. Moreover, the various means of actuation can be combined or changed without deviating from the scope of the present technology.

III. Selected Embodiments of Methods of Delivering Implantable Devices

Figure 9:
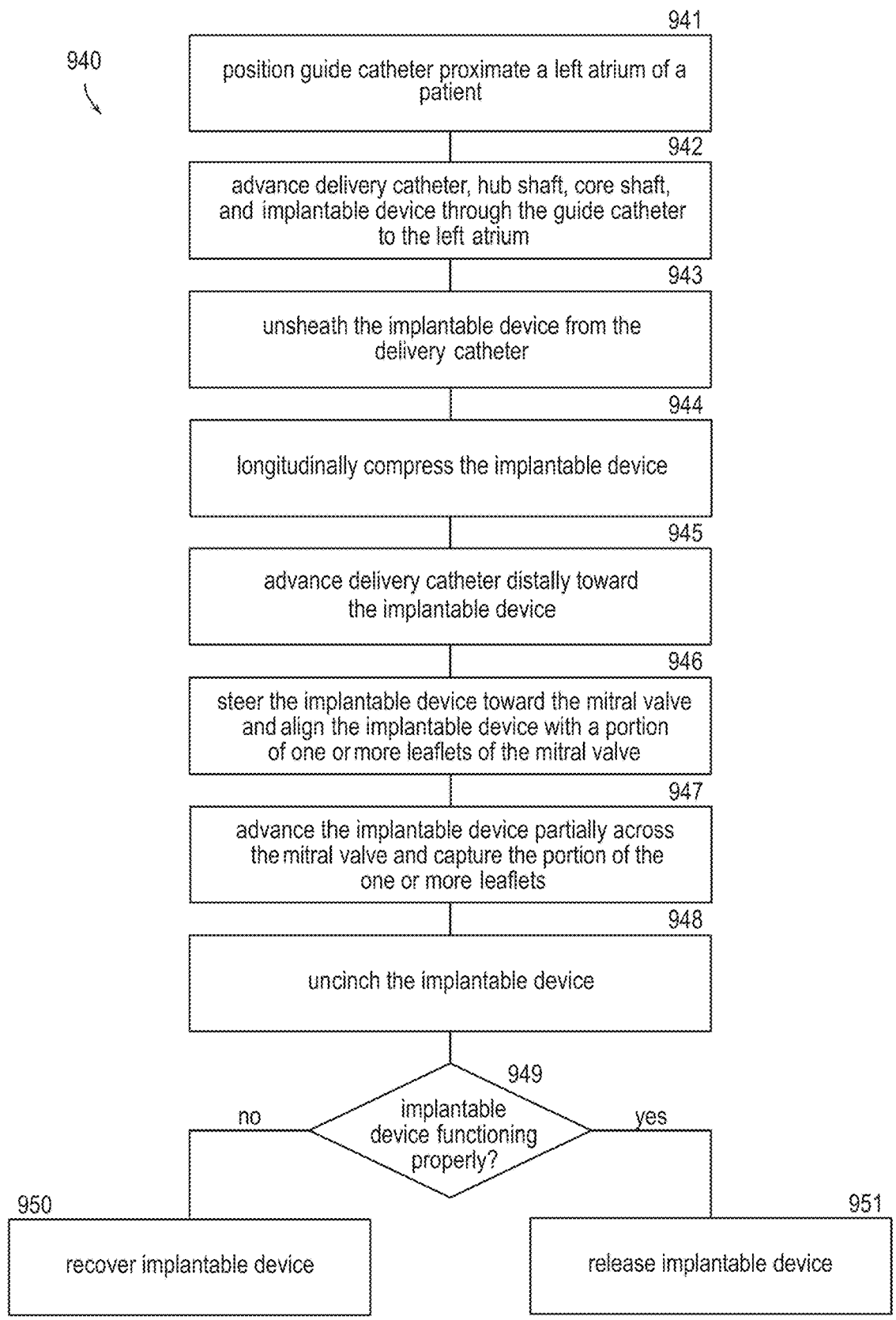
FIG. 9 is a flow diagram of a process or method for operating a delivery system to place the implantable device within a patient in accordance with embodiments of the present technology.

FIG. 9 is a flow diagram of a process or method 940 for operating the delivery system 310 (FIGS. 3A-8D, 13A, and 13B) to implant the implantable device 200 (FIGS. 2A, 2B and 4) at a target site within a patient (e.g., at a native mitral valve of a human patient) in accordance with embodiments of the present technology. FIGS. 10A-10I are side views illustrating the implantable device 200 and a distal portion of the delivery system 310 during various stages of the method 940 in accordance with embodiments of the present technology. Although some features of the method 940 are described in the context of the embodiments shown in FIGS. 2A-8H, 13A, and 13B for the sake of illustration, one skilled in the art will readily understand that the method 900 can be carried out using other suitable systems and/or devices described herein (e.g., including the core shaft handle 1428 described in detail with reference to FIGS. 14A-14D). Likewise, although the method 940 is described in the context of delivering the implantable device to a native mitral valve, the method 940 can be employed to deliver implantable devices to other locations (e.g., to other cardiac valves) of a patient.

Figure 10A:
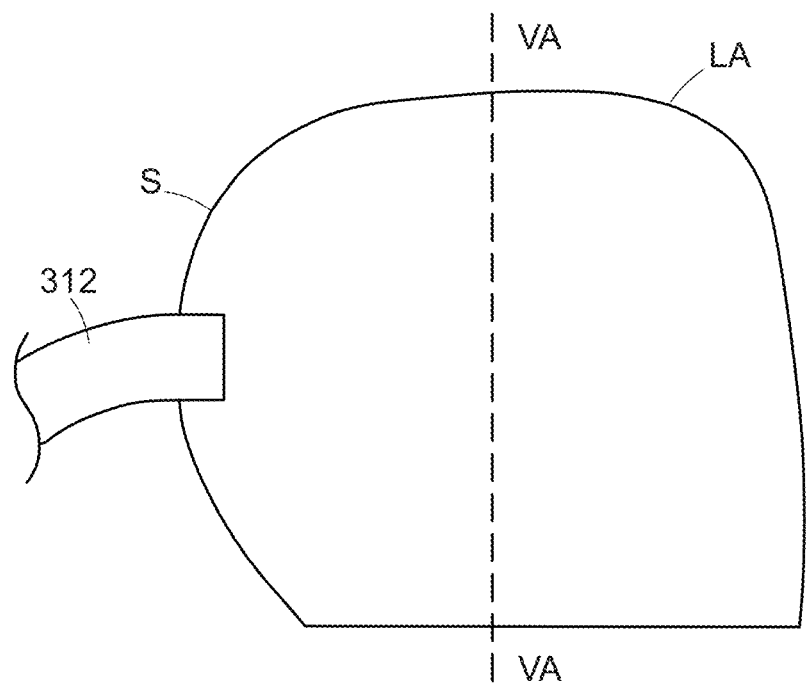
FIGS. 10A-10I are side views illustrating the implantable device and a distal portion of the delivery system during various stages of the method of FIG. 9 in accordance with embodiments of the present technology.

At block 941, the method 940 includes positioning the guide catheter 312 proximate a left atrium of a patient. For example, referring to FIG. 10A, the guide catheter 312 can be inserted to traverse the venous system (e.g., via femoral or axillary access) to the right atrium and then across the interatrial septum S into the left atrium LA via a trans-septal approach (or through the atrial roof in a trans-atrial approach). In some embodiments, a distal portion of the guide catheter 312 can be positioned so that its distal-most end (e.g., the end furthest from the user) is in the left atrium LA. For example, the guide catheter 312 can extend to a location as shown in FIG. 10A, or the guide catheter 312 can be positioned further in the left atrium LA to extend at least generally along the flow axis of the native cardiac valve (e.g., a generally vertical axis VA in FIG. 10A). This alignment can be achieved via a combination of torqueing/steering the guide catheter 312 using the guide catheter handle 322, pre-shaping the end of the guide catheter 312, and/or flexing the guide catheter 312. However, in some embodiments, the guide catheter 312 may not have such complete steerability and its distal tip positioning may be more approximate such that the delivery catheter 314, the hub shaft 316, and/or the core shaft 318 (positioned within the guide catheter 312) can provide additional positioning at the desired location across the septum S.

Figure 10B:
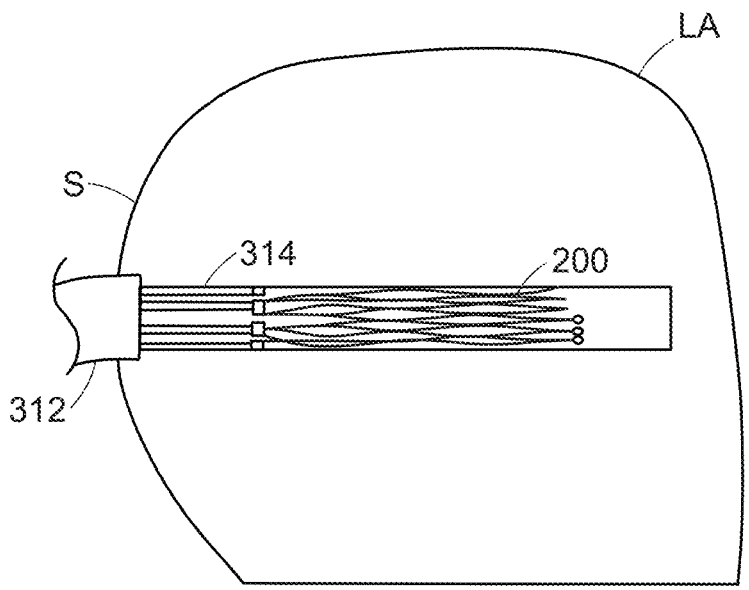
Figure 10D:
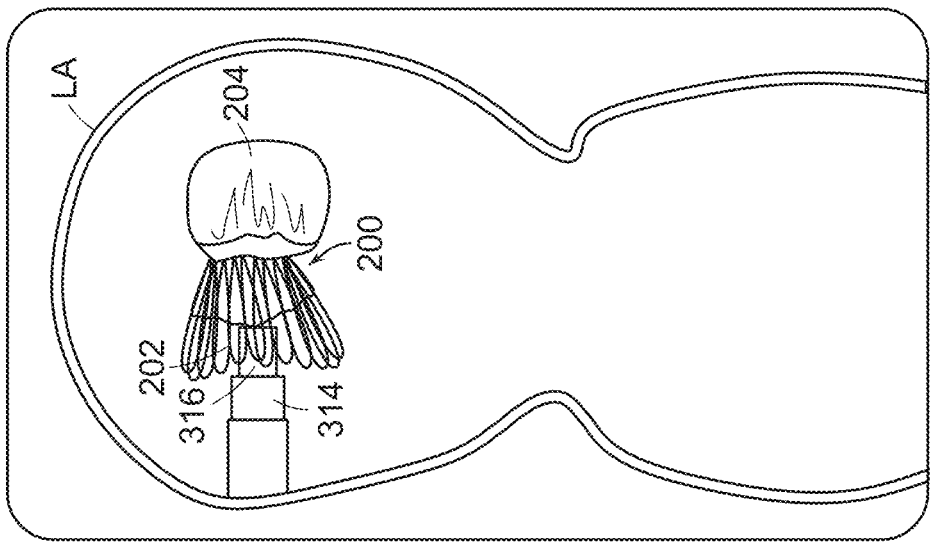
Figure 10C:
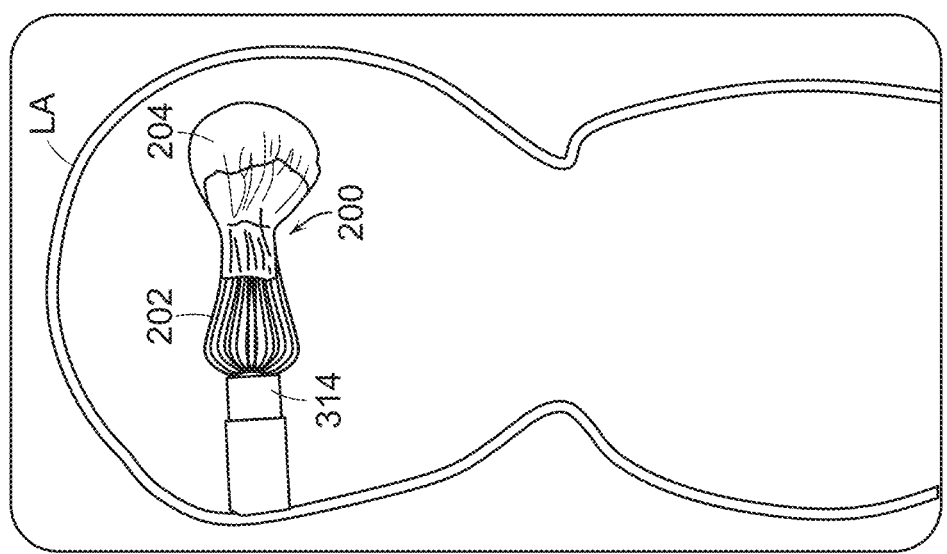

At block 942, the method 940 continues by advancing the delivery catheter 314 (including the implantable device 200 compressed therein), the hub shaft 316, and the core shaft 318 through the guide catheter 312 into the left atrium LA as shown in FIG. 10B. Once positioned within the left atrium LA, the method 940 includes unsheathing the implantable device 200 from the delivery catheter 314 (block 943). For example, FIG. 10C shows the implantable device 200 after being at least partially unsheathed, which allows the atrial-fixation member 202 and the baffle 204 to at least partially expand in the left atrium LA. The implantable device 200 can be unsheathed by proximally retracting the delivery catheter 314 relative to the implantable device 200. In other embodiments, the implantable device 200 can be unsheathed by distally advancing the implantable device 200 relative to the delivery catheter 314 (e.g., via advancement of the hub shaft 316 and the core shaft 318 relative to the delivery catheter 314) in addition to or alternatively to retracting the delivery catheter 314.

At block 944, the method 940 includes longitudinally/axially compressing (e.g., flattening, shortening) the implantable device 200. For example, FIG. 10D shows the implantable device 200 after being compressed. Longitudinally compressing the implantable device 200 includes decreasing a distance between (i) the superior end portion S and the inferior end portion I and (ii) the plug assembly 438 and the core shaft 318. To longitudinally compress the implantable device 200, the user can move the hub shaft 316 and/or the core shaft 318 relative to one another to shorten the distance between the hub assembly 436 of the hub shaft 316 and the plug assembly 438 of the core shaft 318. For example, the user can move the hub shaft handle 326 and/or the core shaft handle 328 toward one another along the support assembly 320. In one aspect of the present technology, longitudinally compressing the implantable device 200 makes the implantable device 200 easier to rotate, translate, and/or position within the space constraints of the left atrium LA. In some embodiments, the implantable device 200 can be axially compressed by more than about 20%, more than about 50%, or more than about 70% relative to its length while compressed in the delivery catheter (block 942) and/or after being unsheathed in the left atrium LA (block 943). In other embodiments, block 943 can be omitted and the implantable device 200 need not be compressed longitudinally.

At block 945 the method 940 can include advancing the delivery catheter 314 distally toward the implantable device 200 such that the delivery catheter 314 is positioned near/over the hub assembly 436 which constrains the struts 206 at the superior end portion S of the implantable device 200. More specifically, the distal end portion of the delivery catheter 314 can be positioned over the hub assembly 436 while the compressed atrial fixation member 202 can at least partially surround the distal end portion of the delivery catheter 314. In some aspects of the present technology, positioning the delivery catheter 314 at least partially over the implantable device 200 can aid in steering the implantable device 200 within the left atrium LA by providing additional rigidity, pushability, and/or torqueability to the implantable device 200.

Figure 10F:
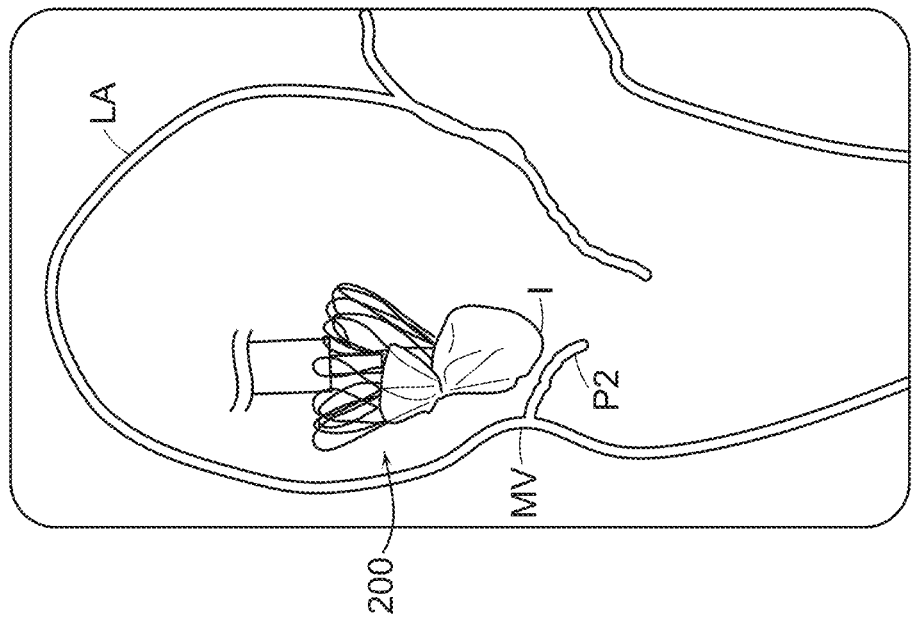
Figure 10E:
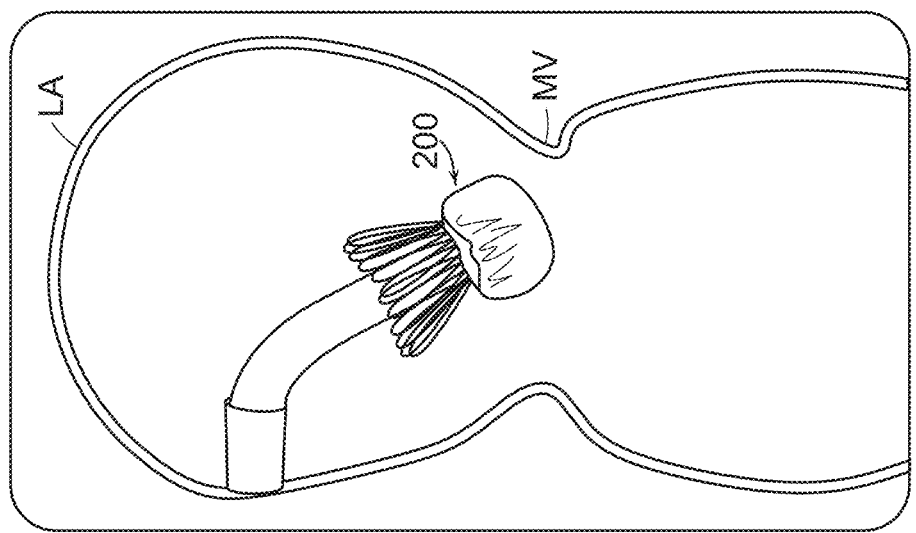

At block 946, the method 940 includes steering the implantable device 200 toward the mitral valve of the patient, such that the inferior end portion I of the implantable device 200 is directed toward the mitral valve annulus, and aligning the implantable device 200 with a portion of one or more desired native leaflets. For example, FIGS. 10E and 10F show the implantable device 200 during and after steering, respectively, the implantable device 200 toward a mitral valve MV and aligning the implantable device 200 with a native leaflet (e.g., the middle scallop P2 of the posterior leaflet) of the mitral valve MV. In some embodiments, the spine 378 of the delivery catheter 314 can help facilitate steering the implantable device 200 toward the mitral valve MV even within the relatively small space of the left atrium LA.

Figure 10H:
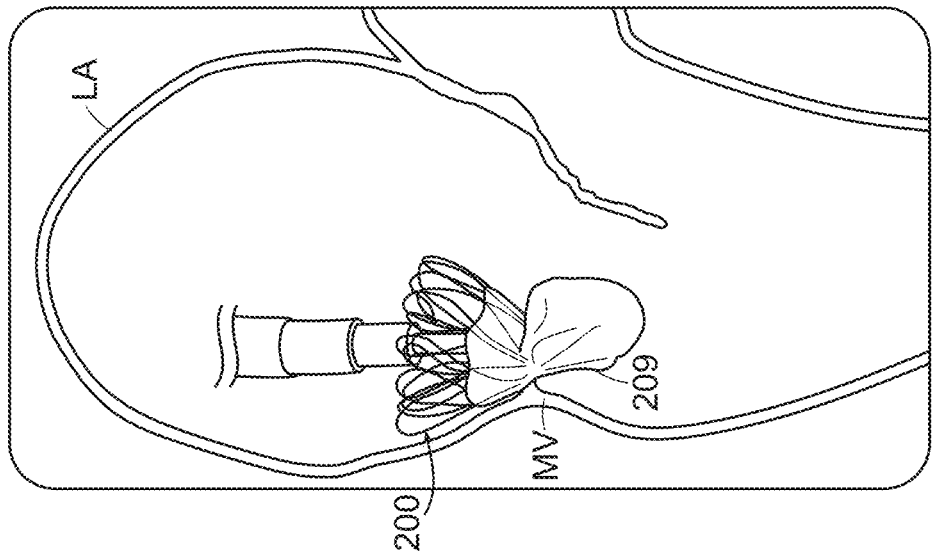
Figure 10G:
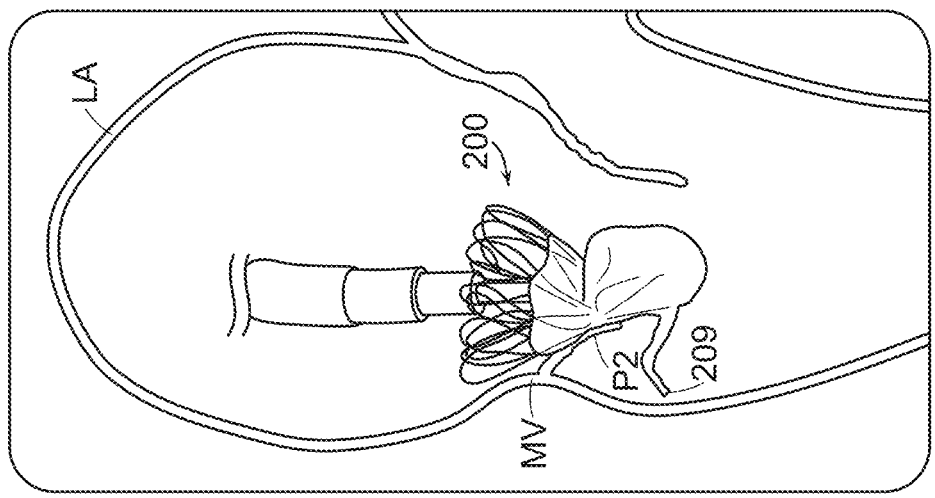
Figure 10I:
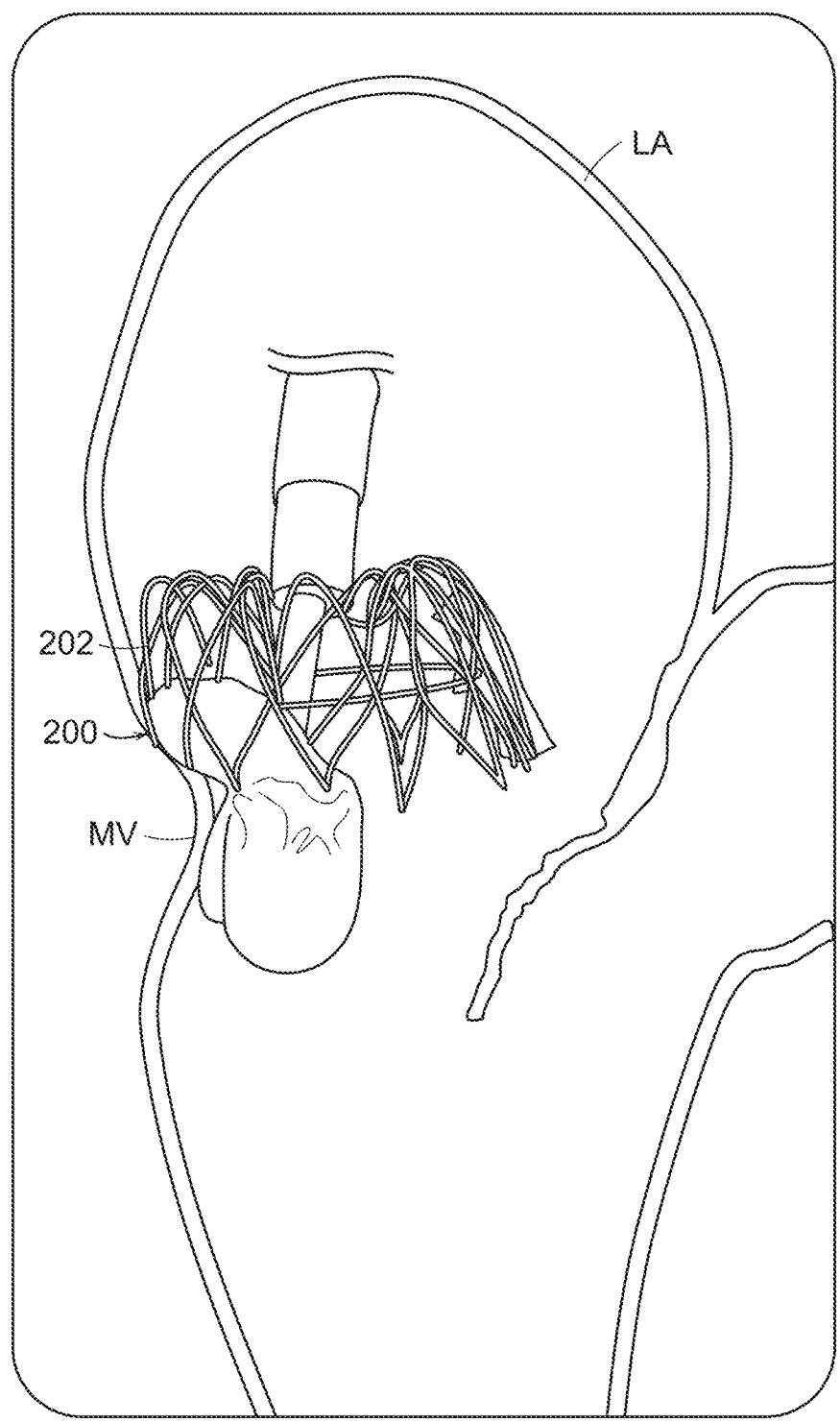

At block 947, after the implantable device 200 is rotationally and radially aligned with the portion of the desired leaflet, the method 940 includes advancing the implantable device 200 at least partially across the mitral valve MV and capturing the portion of the desired leaflet. For example, the implantable device 200 can be steered to the target site such that the implantable device 200 crosses the mitral valve annulus with the atrial-fixation member 202 positioned at least partially above the annulus in the left atrium LA and the coaptation member 204 positioned at or below the annulus in the left ventricle LV. FIGS. 10G and 10H show the implantable device 200 during and after capture of the middle scallop P2 of the posterior leaflet with the clip 209. In some embodiments, the clip 209 can be opened before or after crossing the mitral MV as shown in FIG. 10G, and then closed to capture the middle scallop P2 of the posterior leaflet between the clip 209 and the baffle 204. As described in detail above with reference to FIGS. 2A, 2B, and 8A-8D, the user can open and close the clip 209 by actuating (e.g., depressing and then sliding) the clip actuator 806 of the core shaft handle 328. In some embodiments, the clip 209 can be opened to help orient the implantable device 200 within the left atrium LA.

In general, to steer the implantable device 200 to capture the desired native leaflet (blocks 946 and 947), the user can manipulate one or more of the handles 322-328. For example, the user can manipulate the guide catheter handle 322 and/or the delivery catheter handle 324 to advance and/or deflect the guide catheter 312 and/or the delivery catheter 314 in one or more directions—such as in a direction toward the mitral valve MV—to facilitate positioning of the implantable device 200. In some embodiments, re-advancing the delivery catheter 314 toward the implantable device 200, as shown in FIG. 10E, facilitates positioning/steering of the implantable device via manipulation of the delivery catheter 314. Moreover, the implantable device 200 can be oriented as desired by rotating, for example, the hub shaft handle 326 and the core shaft handle 328 together relative to the delivery catheter 314. For example, with additional reference to FIG. 3, the hub shaft handle 326 and the core shaft handle 328 can be rotated together about the second mount 327b and the third mount 327c, respectively. In some embodiments, because the hub shaft handle 326 and the core shaft handle 328 are coupled together via the rails 332, rotating one of the handles also rotates the other one of the handles.

Once the implantable device 200 is correctly positioned across the mitral valve MV with the coaptation member 204 in place with respect to the native leaflets, the method 940 can continue at block 948 by allowing the atrial-fixation member 202 to expand within the left atrium LA above the mitral valve MV by uncinching the atrial-fixation member 202. For example, FIG. 10H shows the implantable device 200 after uncinching the atrial-fixation member 202. The user can uncinch the atrial-fixation member 202 by rotating the cinch actuator 808 to release tension from the cinch tendon 439. In some embodiments, the atrial-fixation member 202 does not contact the walls of the left atrium LA after being uncinched, or only a portion of the atrial-fixation member 202 contacts tissue within the left atrium LA (e.g., the posterior aspect of the left atrium LA).

At block 949, the method 940 includes determining/assessing whether the implantable device 200 is properly positioned and functioning properly. The performance of the implantable device 200, such as a reduction in an amount of mitral regurgitation, can be evaluated via transesophageal echocardiography ("TEE") imaging or another suitable technique.

At block 950, if the implantable device 200 is not functioning properly, the implantable device can be repositioned or recovered and removed from the patient. For example, the cinch actuator 808 can be actuated to radially compress the atrial-fixation member 202. Then, the clip 209 can be opened to release the native leaflet by actuating (e.g., sliding) the clip actuator 806 of the core shaft handle 328, and the implantable device 200 can be retracted into the left atrium LA. The implantable device 200 can then either be repositioned or removed. Prior to removal, in some embodiments the implantable device 200 can be elongated along its longitudinal axis by moving the hub shaft handle 326 and/or the core shaft handle 328 to move the hub shaft 316 and/or the core shaft 318 relative to one another to lengthen the distance between the hub assembly 436 of the hub shaft 316 and the plug assembly 438 of the core shaft 318. Elongating the implantable device 200 further radially compresses the implantable device 200. Finally, the implantable device 200 can be retracted into the guide catheter 312 and removed from the patient.

Figure 11:
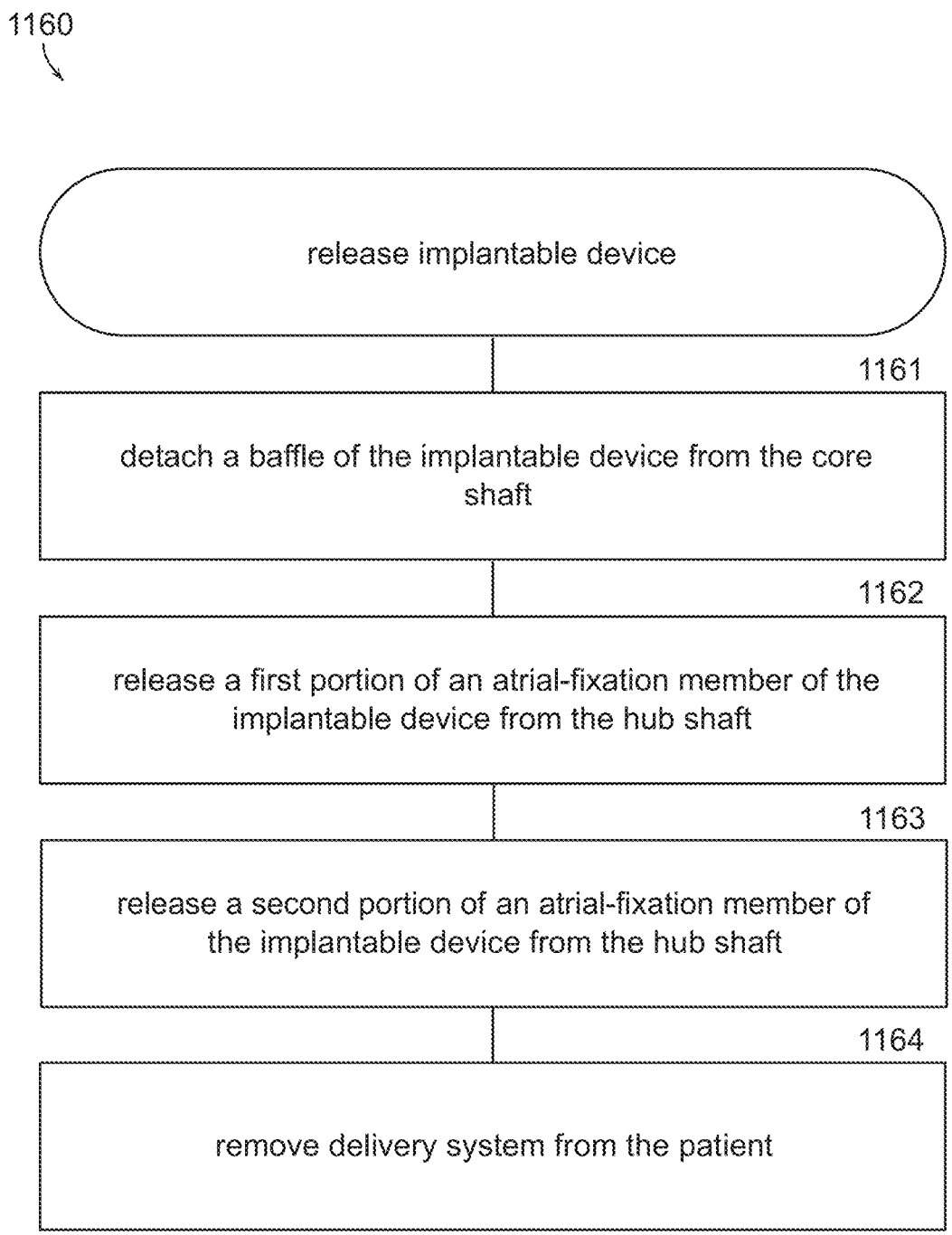
FIG. 11 is a flow diagram illustrating a process or method for releasing an implantable device from a delivery system in accordance with embodiments of the present technology.

If the clinician decides that the implantable device 200 is functioning properly, the method 940 can continue to block 951 in which the implantable device 200 is fully released/detached from the delivery system 310. More specifically, FIG. 11 is a flow diagram illustrating a process or method 1160 for releasing the implantable device at block 951 in accordance with embodiments of the present technology. FIGS. 12A-12D are side views illustrating the implantable device 200 and a distal portion of the delivery system 310 during various stages of the release method 1160 in accordance with embodiments of the present technology.

At block 1161, the release method 1160 includes detaching the baffle 204 from the delivery system 310, and more specifically from the core shaft 318. Detaching the baffle 204 can include actuating the baffle actuator 804 of the core shaft handle 328 to unscrew the baffle connection member 796 from the delivery attachment member 203 positioned within the hollow interior of the baffle 204. In some embodiments, the baffle 204 can be detached from the core shaft 318 prior to uncinching of the implantable device 200 (block 948 of FIG. 9). In some embodiments, the tendons 439, 821 can be released (e.g., cut through the opening 805 in the core shaft handle 328) before detaching the baffle 204.

Figure 12B:
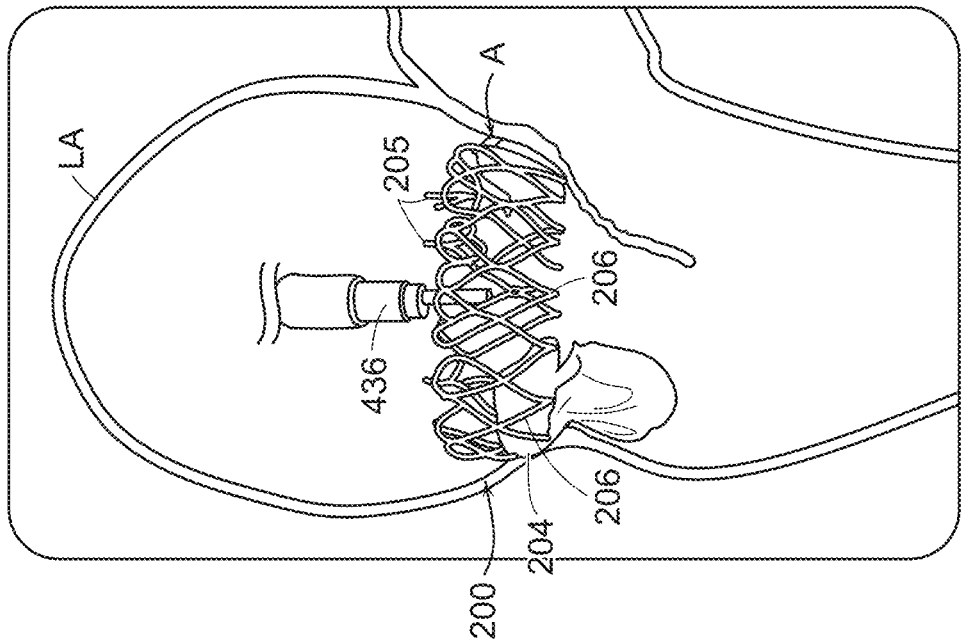
FIGS. 12A-12C are side views illustrating the implantable device and a distal portion of the delivery system during various stages of the method of FIG. 11 in accordance with embodiments of the present technology.
Figure 12A:
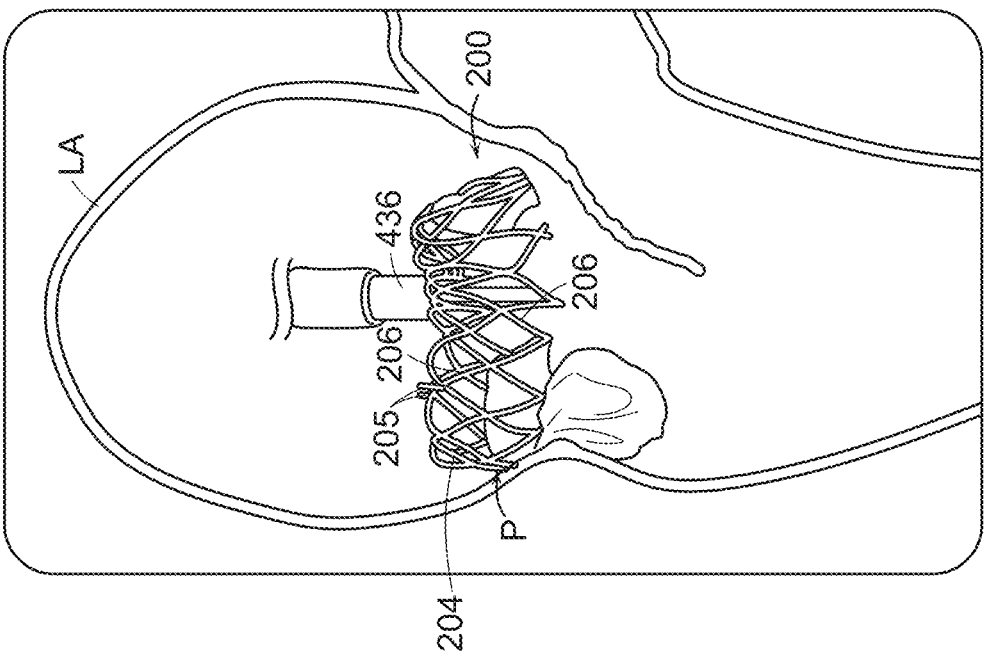

At block 1162, the release method 1160 includes releasing a first portion of the atrial-fixation member 202 from the hub assembly 436 of the hub shaft 316. For example, FIG. 12A illustrates the implantable device 200 after releasing the connectors 205 positioned at the posterior side portion P of the implantable device 200. As described in detail above, the connectors 205 positioned at the posterior side portion P of the implantable device 200 can be released by actuating the ring gear 684 of the hub shaft handle 326 to drive the hub assembly 436 to the second position. With the first set of connectors 205 released, the first portion of the atrial-fixation member 202 (e.g., the struts 206 near the posterior side portion P) can further expand radially outwardly to contact and fixedly engage a wall of the left atrium LA.

At block 1163, the release method 1160 includes releasing a second portion of the atrial-fixation member 202 from the hub assembly 436 of the hub shaft 316. For example, FIG. 12B illustrates the implantable device 200 after releasing the connectors 205 positioned at the anterior side portion A of the implantable device 200. As described in detail above, the connectors 205 positioned at the anterior side portion A of the implantable device 200 can be released by (i) pulling the release member 685 of the hub shaft handle 326 to disengage the release shaft 562 from the lock pin 558 and then (ii) actuating the ring gear 684 of the hub shaft handle 326 to drive the hub assembly 436 to the third position. After release, the second portion of the atrial-fixation member 202 (e.g., the struts 206 near the anterior side portion A) can contact and fixedly engage the wall of the left atrium LA. In some embodiments, the position and/or orientation of the implantable device 200 can be manipulated after releasing the first portion of the atrial-fixation member 202 and before releasing the second portion of the atrial-fixation member 202.

Figure 12C:
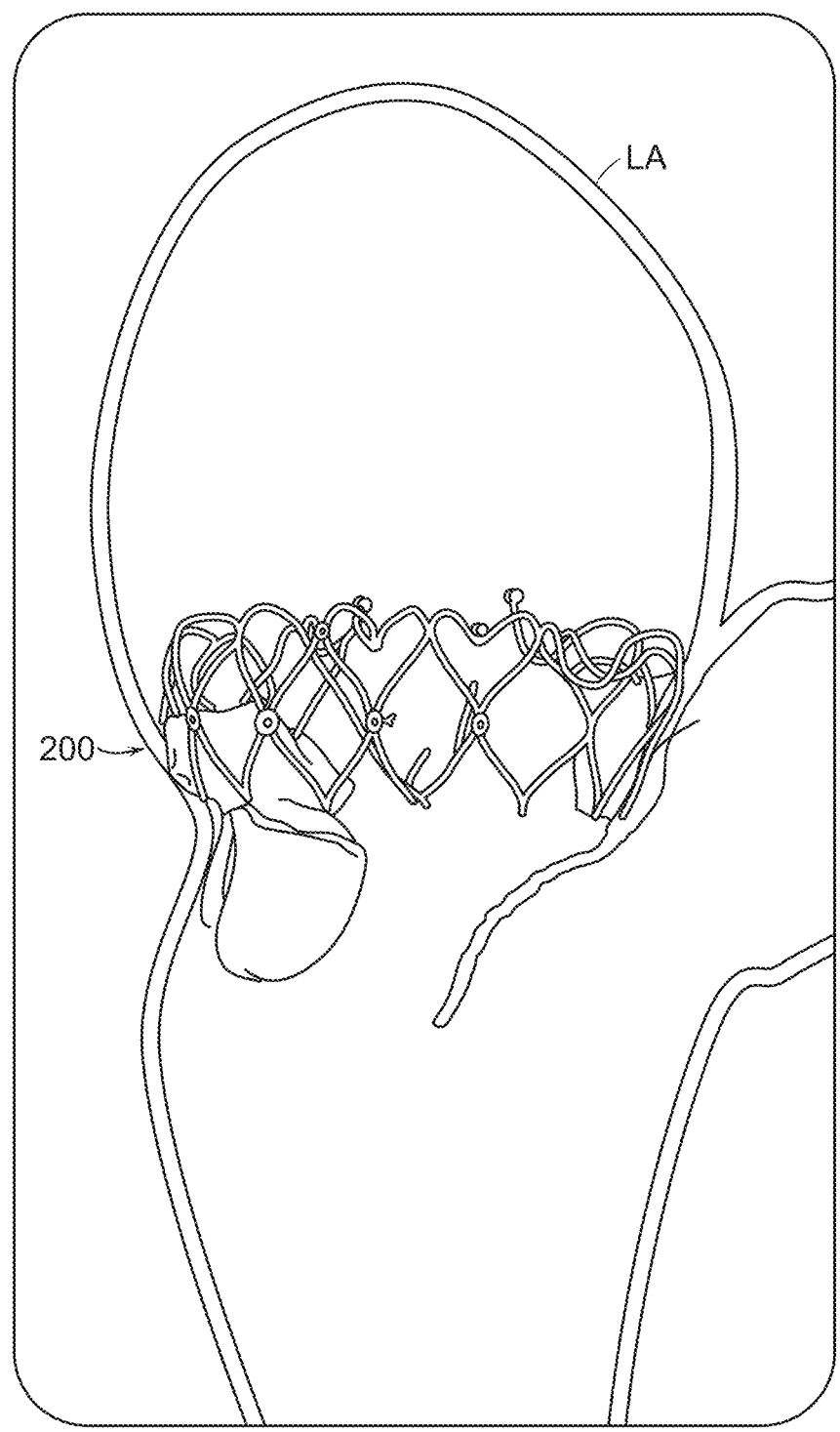

At block 1164, the release method 1160 includes removing the delivery system 310 from the patient. For example, the catheters 312-314 can be individually or collectively withdrawn from the patient such that only the implantable device 200 remains, as shown in FIG. 12C.

Referring to FIGS. 2A-12C together, the delivery system 310 has several advantages that enable the delivery system 310 to reliably implant the implantable device 200 at the mitral valve MV to have a proper position and orientation. For example, the delivery system 310 allows for the separate control of the atrial-fixation member 202 and the coaptation member 204, and allows these components to be separately released from the delivery system 310. Additionally, the delivery system 310 facilitates the longitudinal compression of the implantable device 200 that allows the implantable device 200 to be navigated through the tight anatomy of the left atrium LA. Moreover, the hub assembly 436 allows the atrial-fixation member 202 to be released in two stages to facilitate the proper engagement of the atrial-fixation member 202 with the wall of the left atrium LA. Other advantages are described in detail throughout.

IV. Further Examples

The following examples are illustrative of several embodiments of the present technology:

1. A delivery system for endovascularly implanting a valve repair device at a mitral valve, the delivery system comprising:
   - a delivery catheter having a distal portion configured to be endovascularly delivered to a left atrium, wherein the distal portion is configured to hold the valve repair device in a delivery state;
   - a hub shaft extending through the delivery catheter, the hub shaft having a proximal portion and a distal portion;
   - a hub assembly coupled to the distal portion of the hub shaft, wherein—
     - the hub assembly includes an inner hub component that is movable relative to an outer hub component between a first position, a second position, and a third position,
     - in the first position, the hub is configured to secure a first end portion of the valve repair device between the inner and outer hub components,
     - movement of the inner hub component from the first position to the second position is configured to release a first side portion of the first end portion of the valve repair device, and
     - movement of the inner hub component from the second position to the third position is configured to release a second side portion of the first end portion of the valve repair device to release the first end portion from the hub; and
   - a core shaft extending through and independently movable with respect to the hub shaft, the core shaft having a plug assembly configured to releasably engage a second end portion of the valve repair device.

2. The delivery system of example 1 wherein the inner hub component includes a plurality of recesses configured to receive corresponding ones of a plurality of connectors of the valve repair device.

3. The delivery system of example 2 wherein the recesses include a group of first recesses and a group of second recesses, wherein the second recesses each have a different shape than the first recesses.

4. The delivery system of example 3 wherein the inner hub component includes a distal edge and a proximal edge, wherein the first recesses extend from the distal edge partially toward the proximal edge, and wherein the second recesses extend from the distal edge toward the proximal edge farther than the first recesses.

5. The delivery system of example 3 or example 4 wherein—
   - in the first position, the first and second recesses are covered by the outer hub component;
   - in the second position, (a) the first recesses are positioned distal of the outer hub component to permit the first side portion of the valve repair device to release and (b) the second recesses are covered by the outer hub component; and
   - in the third position, the first and second recesses are positioned distal of the outer hub component to permit the second side portion of the valve repair device to release.

6. The delivery system of any one of examples 3-5 wherein the group of first recesses is circumferentially spaced apart from the group of second recesses about the inner hub component.

7. The delivery system of any one of examples 1-6 wherein the hub assembly further comprises a lock pin configured to engage the inner and outer hub components in the second position to inhibit movement of the inner hub component from the second position to the third position.

8. The delivery system of example 7, further comprising a release shaft operably coupled to the lock pin, wherein the release shaft is actuatable to permit the lock pin to disengage the outer hub component to permit movement of the inner hub component from the second position to the third position.

9. The delivery system of example 8 wherein the lock pin includes a release lumen configured to receive the release shaft therein, wherein the release shaft is configured to bias the lock pin radially outward to engage the outer hub component, and wherein the release shaft is removable from the release lumen to permit the lock pin to disengage the outer hub component.

10. The delivery system of any one of examples 1-9, further comprising a drive shaft, wherein the hub assembly includes a lead screw operably coupling the drive shaft to the inner hub component, and wherein rotation of the drive shaft rotates the lead screw to move the inner hub component between the first, second, and/or third positions.

11. The delivery system of example 10 wherein the inner hub component includes a stop surface, and wherein the lead screw includes a stop portion configured to engage the stop surface in the third position to inhibit further movement of the inner hub component from the third position in a direction away from the second position.

12. A delivery system for implanting a medical device having an atrial-fixation member and a coaptation member extending from the atrial-fixation member, the delivery system comprising:
  a hub shaft having a hub assembly configured to releasably engage the atrial-fixation member; and
  a core shaft extending through the hub shaft and having a plug configured to releasably engage the coaptation member,
    wherein the hub shaft and the core shaft are independently movable relative to one another to change an axial length of the medical device,
    wherein the hub is actuatable to release the atrial-fixation member, and
    wherein the core shaft is actuatable to release the coaptation member.

13. The delivery system of example 12 wherein the atrial-fixation member has a posterior side and an anterior side, wherein the hub assembly is movable between a first position, a second position, and a third position, and wherein—
  in the first position, the hub assembly is configured to secure the posterior side and the anterior side of the atrial-fixation member,
  movement of the hub assembly from the first position to the second position is configured to release the posterior side of the atrial-fixation member from the hub assembly, and
  movement of the hub assembly from the second position to the third position is configured to release the anterior side of the atrial-fixation member from the hub assembly.

14. The delivery system of example 13, further comprising:
  a hub shaft handle coupled to a proximal portion of the hub shaft; and
  a drive shaft extending through the hub shaft and operably coupling the hub assembly to the hub shaft handle, wherein the hub shaft handle includes a drive actuator configured to drive the drive shaft to move the hub assembly between the first, second, and/or third positions.

15. The delivery system of example 14 wherein the drive actuator includes a ring gear.

16. The delivery system of any one of examples 13-15 wherein the hub assembly further comprises a lock mechanism configured to inhibit movement of the hub assembly from the second position to the third position.

17. The delivery system of example 16, further comprising:
  a hub shaft handle coupled to a proximal portion of the hub shaft; and
  a release shaft extending through the hub shaft and operably coupling the lock mechanism to the hub shaft handle, wherein the hub shaft handle includes a release actuator configured to decouple the release shaft from the lock mechanism to permit movement of the hub assembly from the second position to the third position.

18. The delivery system of example 17 wherein the release actuator is a pull member configured to pull the release shaft proximally away from the hub assembly.

19. The delivery system of any one of examples 16-18, further comprising:
  a hub shaft handle coupled to a proximal portion of the hub shaft;
  a drive shaft extending through the hub shaft and operably coupling the hub assembly to the hub shaft handle, wherein the hub shaft handle includes a drive actuator configured to drive the drive shaft to move the hub assembly between the first, second, and/or third positions; and
  a release shaft extending through the hub shaft and operably coupling the lock mechanism to the hub shaft handle, wherein the hub shaft handle further includes a release actuator configured to decouple the release shaft from the lock mechanism to permit movement of the hub assembly from the second position to the third position.

20. The delivery system of any one of examples 12-19 wherein the plug includes a screw configured to releasably engage a delivery attachment member of the coaptation member.

21. The delivery system any one of examples 12-20, further comprising:
  a core shaft handle coupled to a proximal portion of the core shaft; and
  a drive shaft extending through the core shaft and operably coupling the plug to the core shaft handle, wherein the core shaft handle includes a drive actuator configured to drive the drive shaft to disengage the plug from the coaptation member.

22. The delivery system of example 21, further comprising a tendon extending through the core shaft and operably coupling the atrial-fixation member to the core shaft handle, wherein the core shaft handle includes a cinch actuator configured to tension the tendon to radially compress the atrial fixation member.

23. The delivery system of example 22 wherein the core shaft handle includes a mount assembly having a body, a mount configured to secure the tendon, and a biasing member operably coupling the mount to the body, and wherein the cinch actuator is coupled to the body and configured to move the mount assembly to tension the tendon.

24. The delivery system of example 23 wherein movement of the mount assembly in a first direction loads the biasing member.

25. A method of implanting a valve repair device at a cardiac valve, the method including: endovascularly delivering a distal portion of a delivery catheter to a chamber of a heart; unsheathing at least a portion of the valve repair device from the delivery catheter while in the chamber of the heart;
  longitudinally compressing the valve repair device by moving one or both of (a) a hub shaft secured to a first end portion of the valve repair device and (b) a core shaft secured to a second end portion of the valve repair device relative to one another;
  advancing the valve repair device to a target position extending across the cardiac valve such that the first end portion is positioned at a first side of the cardiac valve upstream of a native valve anulus of the cardiac valve and the second end portion is positioned at a second side of the cardiac valve proximate to native valve leaflets of the cardiac valve;
  releasing the second end portion of the valve repair device from the core shaft;
  releasing a first side of the first end portion of the valve repair device from the hub shaft; and after releasing the first side of the first end portion of the valve repair device, releasing a second side of the first end portion of the valve repair device from the hub shaft.

26. The method of example 25 wherein releasing the first side of the first end portion of the valve repair device includes actuating a handle operably coupled to a proximal end portion of the hub shaft to drive a hub assembly coupled to a distal end portion of the hub shaft to release a plurality of first connectors at the first side of the first end portion of the valve repair device.

27. The method of example 26 wherein releasing the second side of the first end portion of the valve repair device includes further actuating the handle to drive the hub assembly to release a plurality of second connectors at the second side of the first end portion of the valve repair device.

28. The method of any one of examples 25-27 wherein the cardiac valve is a mitral valve, and wherein the method further comprises capturing a portion of one or more of the native leaflets of the mitral valve with the valve repair device.

29. The method of any one of examples 25-28 wherein the cardiac valve is a mitral valve, and wherein longitudinally compressing the valve repair device includes longitudinally compressing the valve repair device in a left atrium above the mitral valve.

30. The method of any one of examples 25-29 wherein the valve repair device includes an atrial-fixation member and a coaptation member extending from the atrial-fixation member, wherein the first end portion is of the atrial-fixation member, wherein the second end portion is of the coaptation member, and wherein—
  releasing the first side of the first end portion of the valve repair device includes releasing a posterior side of the atrial-fixation member that is positioned above the coaptation member; and
  releasing the second side of the first end portion of the valve repair device includes releasing an anterior side of the atrial-fixation member opposite the posterior side.

31. The method of any one of examples 25-30 wherein releasing the second end portion of the valve repair device from the core shaft includes actuating a handle operably coupled to the core shaft to drive the core shaft to disengage a delivery attachment member fixedly attached to the second end portion of the valve repair device.

32. The method of any one of examples 25-32 wherein the delivery attachment member is a nut, and wherein actuating the handle to drive the core shaft to disengage the nut includes rotating a threaded member of the core shaft to disengage the nut.

33. A delivery system for implanting a medical device, comprising:
  a hub shaft having a proximal portion and a distal portion; and
  a hub assembly coupled to the distal portion of the hub shaft, wherein—
    the hub assembly includes an inner hub component that is movable relative to an outer hub component between a first position, a second position, and a third position,
    in the first position, the hub is configured to secure an end portion of the medical device between the inner and outer hub components,
    movement of the inner hub component from the first position to the second position is configured to release a first side portion of the end portion of the medical device, and
    movement of the inner hub component from the second position to the third position is configured to release a second side portion of the end portion of the medical device to release the medical device from the hub.

V. Conclusion

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A delivery system for endovascularly implanting a valve repair device at a mitral valve, the delivery system comprising:
  a delivery catheter having a distal portion configured to be endovascularly delivered to a left atrium, wherein the distal portion is configured to hold the valve repair device in a delivery state;
  a hub shaft extending through the delivery catheter, the hub shaft having a proximal portion and a distal portion;
  a hub assembly coupled to the distal portion of the hub shaft, wherein— the hub assembly includes an inner hub component that is movable relative to an outer hub component between a first position, a second position, and a third position, in the first position, the hub assembly is configured to secure a first end portion of the valve repair device between the inner and outer hub components, movement of the inner hub component from the first position to the second position is configured to release a first side portion of the first end portion of the valve repair device, and movement of the inner hub component from the second position to the third position is configured to release a second side portion of the first end portion of the valve repair device to release the first end portion from the hub assembly; and a core shaft extending through and independently movable with respect to the hub shaft, the core shaft having a plug assembly configured to releasably engage a second end portion of the valve repair device.

2. The delivery system of claim 1 wherein the inner hub component includes a plurality of recesses configured to receive corresponding ones of a plurality of connectors of the valve repair device.

3. The delivery system of claim 2 wherein the recesses include a group of first recesses and a group of second recesses, wherein the second recesses each have a different shape than the first recesses.

4. The delivery system of claim 3 wherein the inner hub component includes a distal edge and a proximal edge, wherein the first recesses extend from the distal edge partially toward the proximal edge, and wherein the second recesses extend from the distal edge toward the proximal edge farther than the first recesses.

5. The delivery system of claim 3 wherein—
in the first position, the first and second recesses are covered by the outer hub component;
in the second position, (a) the first recesses are positioned distal of the outer hub component to permit the first side portion of the valve repair device to release and (b) the second recesses are covered by the outer hub component; and
in the third position, the first and second recesses are positioned distal of the outer hub component to permit the second side portion of the valve repair device to release.

6. The delivery system of claim 3 wherein the group of first recesses is circumferentially spaced apart from the group of second recesses about the inner hub component.

7. The delivery system of claim 1 wherein the hub assembly further comprises a lock pin configured to engage the inner and outer hub components in the second position to inhibit movement of the inner hub component from the second position to the third position.

8. The delivery system of claim 7, further comprising a release shaft operably coupled to the lock pin, wherein the release shaft is actuatable to permit the lock pin to disengage the outer hub component to permit movement of the inner hub component from the second position to the third position.

9. The delivery system of claim 8 wherein the lock pin includes a release lumen configured to receive the release shaft therein, wherein the release shaft is configured to bias the lock pin radially outward to engage the outer hub component, and wherein the release shaft is removable from the release lumen to permit the lock pin to disengage the outer hub component.

10. The delivery system of claim 1, further comprising a drive shaft, wherein the hub assembly includes a lead screw operably coupling the drive shaft to the inner hub component, wherein rotation of the drive shaft rotates the lead screw to move the inner hub component between the first, second, and/or third positions, wherein the inner hub component includes a stop surface, and wherein the lead screw includes a stop portion configured to engage the stop surface in the third position to inhibit further movement of the inner hub component from the third position in a direction away from the second position.

11. A delivery system for delivering a medical device having first member and a second member extending from the first member, the first member having a posterior side and an anterior side, the delivery system comprising:
a hub shaft having a hub assembly configured to releasably engage the first member and movable between a first position, a second position, and a third position, wherein—
in the first position, the hub assembly is configured to secure the posterior side and the anterior side of the first member,
movement of the hub assembly from the first position to the second position is configured to release the posterior side of the first member from the hub assembly,
movement of the hub assembly from the second position to the third position is configured to release the anterior side of the first member from the hub assembly, and
the hub assembly comprises a lock mechanism configured to inhibit movement of the hub assembly from the second position to the third position; and
a core shaft extending through the hub shaft and having a plug configured to releasably engage the second member, wherein the hub shaft and the core shaft are independently movable relative to one another to change an axial length of the medical device, and wherein the core shaft is actuatable to release the second member.

12. The delivery system of claim 11, further comprising:
a hub shaft handle coupled to a proximal portion of the hub shaft; and
a release shaft extending through the hub shaft and operably coupling the lock mechanism to the hub shaft handle, wherein the hub shaft handle includes a release actuator configured to decouple the release shaft from the lock mechanism to permit movement of the hub assembly from the second position to the third position.

13. The delivery system of claim 11, further comprising:
a hub shaft handle coupled to a proximal portion of the hub shaft;
a drive shaft extending through the hub shaft and operably coupling the hub assembly to the hub shaft handle, wherein the hub shaft handle includes a drive actuator configured to drive the drive shaft to move the hub assembly between the first, second, and/or third positions; and
a release shaft extending through the hub shaft and operably coupling the lock mechanism to the hub shaft handle, wherein the hub shaft handle further includes a release actuator configured to decouple the release shaft from the lock mechanism to permit movement of the hub assembly from the second position to the third position.

14. A delivery system for delivering a medical device having a first member and a second member extending from the first member, the delivery system comprising:
- a delivery catheter configured to hold the medical device in a delivery state;
- a hub shaft extending at least partially through the delivery catheter and having a hub assembly configured to releasably engage the first member;
- a core shaft extending at least partially through the hub shaft and having a plug configured to releasably engage the second member,
  - wherein the hub shaft and the core shaft are independently movable relative to one another to change an axial length of the medical device when the medical device is moved outside the delivery catheter to a partially deployed state,
  - wherein the hub assembly is actuatable to release the first member, and
  - wherein the core shaft is actuatable to release the second member;
- a core shaft handle coupled to a proximal portion of the core shaft;
- a drive shaft extending through the core shaft and operably coupling the plug to the core shaft handle, wherein the core shaft handle includes a drive actuator configured to drive the drive shaft to disengage the plug from the second member; and
- a tendon extending through the core shaft and operably coupling the first member to the core shaft handle, wherein—
  - the core shaft handle includes a cinch actuator configured to tension the tendon to radially compress the first member,
  - the core shaft handle includes a mount assembly having a body, a mount configured to secure the tendon, and a biasing member operably coupling the mount to the body,
  - the cinch actuator is coupled to the body and configured to move the mount assembly to tension the tendon, and
  - movement of the mount assembly in a first direction loads the biasing member.

* * * * *